US010953003B2

(12) United States Patent
Ragan et al.

(10) Patent No.: US 10,953,003 B2
(45) Date of Patent: Mar. 23, 2021

(54) METHODS FOR TREATING CANCER

(71) Applicants: X4 Pharmaceuticals, Inc., Cambridge, MA (US); Genzyme Corp., Cambridge, MA (US)

(72) Inventors: Paula Marie Ragan, Belmont, MA (US); Robert D. Arbeit, West Newton, MA (US); Kieran James Crowley, Highland Park, NJ (US)

(73) Assignees: X4 PHARMACEUTICALS, INC., Cambridge, MA (US); GENZYME CORP., Cambridge, MA (US)

( * ) Notice: Subject to any disclaimer, the term of this patent is extended or adjusted under 35 U.S.C. 154(b) by 0 days.

(21) Appl. No.: 16/061,974

(22) PCT Filed: Dec. 14, 2016

(86) PCT No.: PCT/US2016/066634
§ 371 (c)(1),
(2) Date: Jun. 13, 2018

(87) PCT Pub. No.: WO2017/106328
PCT Pub. Date: Jun. 22, 2017

(65) Prior Publication Data
US 2018/0369229 A1 Dec. 27, 2018

Related U.S. Application Data

(60) Provisional application No. 62/267,052, filed on Dec. 14, 2015, provisional application No. 62/271,087, filed on Dec. 22, 2015, provisional application No. 62/281,962, filed on Jan. 22, 2016, provisional application No. 62/428,964, filed on Dec. 1, 2016.

(51) Int. Cl.
| | |
|---|---|
| *A61K 31/4709* | (2006.01) |
| *A61K 9/48* | (2006.01) |
| *A61K 9/14* | (2006.01) |
| *A61K 47/02* | (2006.01) |
| *A61K 47/14* | (2017.01) |
| *A61K 47/20* | (2006.01) |
| *A61K 47/38* | (2006.01) |
| *A61P 35/00* | (2006.01) |

(52) U.S. Cl.
CPC .......... *A61K 31/4709* (2013.01); *A61K 9/485* (2013.01); *A61K 9/4858* (2013.01); *A61K 9/4866* (2013.01); *A61K 47/02* (2013.01); *A61K 47/14* (2013.01); *A61K 47/20* (2013.01); *A61K 47/38* (2013.01); *A61P 35/00* (2018.01); *A61K 9/14* (2013.01)

(58) Field of Classification Search
CPC .... A61K 31/4709; A61K 47/02; A61K 47/14; A61K 47/20; A61K 47/38; A61K 9/14; A61K 9/485; A61K 9/4858; A61K 9/4866; A61P 35/00
See application file for complete search history.

(56) References Cited

U.S. PATENT DOCUMENTS

| | | | |
|---|---|---|---|
| 4,933,447 A | 6/1990 | Konno et al. |
| 5,021,409 A | 6/1991 | Murrer et al. |
| 5,235,056 A | 8/1993 | Cunkle et al. |
| 5,563,151 A | 10/1996 | Bowles et al. |
| 5,582,823 A | 12/1996 | Souza et al. |
| 5,583,131 A | 12/1996 | Bridger et al. |
| 5,698,546 A | 12/1997 | Bridger et al. |
| 5,817,807 A | 10/1998 | Bridger et al. |
| 5,932,749 A | 8/1999 | Li et al. |
| 6,001,826 A | 12/1999 | Murrer et al. |
| 6,245,799 B1 | 6/2001 | Asseslin et al. |
| 6,268,354 B1 | 7/2001 | Nishimura et al. |
| 6,365,583 B1 | 4/2002 | MacFarland et al. |
| 6,506,770 B1 | 1/2003 | Bridger et al. |
| 6,552,065 B2 | 4/2003 | Remiszewski et al. |
| 6,635,278 B1 | 10/2003 | Dahl et al. |
| 6,683,192 B2 | 1/2004 | Baxter et al. |
| 6,734,191 B2 | 5/2004 | Bridger et al. |
| 6,734,194 B2 | 5/2004 | End et al. |
| 6,794,379 B2 | 9/2004 | Medina et al. |
| 6,825,351 B2 | 11/2004 | McEachern et al. |
| 6,835,731 B2 | 12/2004 | Bridger et al. |
| 6,864,265 B2 | 3/2005 | Bridger et al. |
| 6,878,714 B2 | 4/2005 | Askew et al. |
| 6,987,102 B2 | 1/2006 | Bridger et al. |

(Continued)

FOREIGN PATENT DOCUMENTS

| | | |
|---|---|---|
| EP | 0434385 | 6/1991 |
| WO | WO-1997009976 | 3/1997 |

(Continued)

OTHER PUBLICATIONS

Skerlj et. al., Journal of Medicinal Chemistry, 2010, ACS, vol. 53, pp. 3376-3388 (Year: 2010).*
"Common Terminology Criteria for Adverse Events (CTCAE), Version 4.0," U.S. Department of Health and Human Services, National Institutes of Health, National Cancer Institute, NIH Publication No. 09-5410, May 28, 2009, revised Jun. 2010 (196 pages).
"European Medicines Agency, Background Review for Sodium Laurilsulfate Used as an Excipient," Jul. 23, 2015, http://www.ema.europa.eu/docs/en_GB/document_library/Report/2015/08/WC500191475.pdf. p. 5, table 1. Date Accessed Jan. 23, 2017 (18 pages).
"Nivolumab," Drugbank, http://www.drugbank.ca/drugs/DB09035. Date Accessed, Nov. 30, 2018 (14 pages).

(Continued)

*Primary Examiner* — Sarah Pihonak
(74) *Attorney, Agent, or Firm* — Dechert LLP; Andrea L.C. Reid; Joseph W. Arico

(57) ABSTRACT

The present invention relates to methods of treating patients with advanced forms of cancer, such as clear cell renal cell carcinoma, in which X4P-001 is administered in order to reduce angiogenic escape that typically occurs with TKI therapy. The methods demonstrate surprising results, including regression of tumor size and cell number, with comparatively little toxicity.

14 Claims, 17 Drawing Sheets

(56) References Cited

U.S. PATENT DOCUMENTS

| | | |
|---|---|---|
| 7,053,215 B2 | 5/2006 | Medina et al. |
| 7,091,217 B2 | 8/2006 | Bridger et al. |
| 7,135,570 B2 | 11/2006 | McEachern et al. |
| 7,169,750 B2 | 1/2007 | Bridger et al. |
| 7,291,631 B2 | 11/2007 | Bridger et al. |
| 7,332,605 B2 | 2/2008 | Crawford et al. |
| 7,354,932 B2 | 4/2008 | Bridger et al. |
| 7,354,934 B2 | 4/2008 | Bridger et al. |
| 7,452,994 B2 | 11/2008 | McEachern et al. |
| 7,491,544 B2 | 2/2009 | Canary et al. |
| 7,501,518 B2 | 3/2009 | Chen et al. |
| 7,550,484 B2 | 6/2009 | Bridger et al. |
| 7,592,351 B2 | 9/2009 | Sundermann et al. |
| 7,723,525 B2 | 5/2010 | Crawford et al. |
| 7,863,293 B2 | 1/2011 | Bridger et al. |
| 7,897,590 B2 | 3/2011 | Bridger et al. |
| 7,935,692 B2 | 5/2011 | Bridger et al. |
| 8,168,783 B2 | 5/2012 | Kokubo et al. |
| 8,178,123 B2 | 5/2012 | Pauletti et al. |
| 8,778,967 B2 | 7/2014 | Bridger et al. |
| 8,889,159 B2 | 11/2014 | Cleary et al. |
| 8,906,682 B2 | 12/2014 | June et al. |
| 9,119,790 B2 | 9/2015 | Crowley et al. |
| 9,155,723 B2 | 10/2015 | Jain et al. |
| 9,267,934 B2 | 2/2016 | Singh et al. |
| 9,314,468 B2 | 4/2016 | Clark et al. |
| 10,548,889 B1 | 2/2020 | Brands |
| 10,610,527 B2 | 4/2020 | Arbeit et al. |
| 2003/0220341 A1 | 11/2003 | Bridger et al. |
| 2003/0232808 A1 | 12/2003 | Kobayashi et al. |
| 2005/0154201 A1 | 7/2005 | Chen et al. |
| 2005/0227958 A1 | 10/2005 | Wang et al. |
| 2007/0123538 A1 | 5/2007 | Dunkle et al. |
| 2007/0167459 A1 | 7/2007 | Habashita et al. |
| 2007/0232615 A1 | 10/2007 | Gudmundsson et al. |
| 2008/0045537 A1 | 2/2008 | Gudmundsson et al. |
| 2008/0058353 A1 | 3/2008 | Banks |
| 2008/0096861 A1 | 4/2008 | Gudmundsson et al. |
| 2008/0167341 A1 | 7/2008 | Bridger et al. |
| 2008/0171740 A1 | 7/2008 | Gudmundsson et al. |
| 2009/0203533 A1 | 8/2009 | Munnes et al. |
| 2009/0247570 A1 | 10/2009 | Mayer |
| 2009/0325877 A1 | 12/2009 | Grunt et al. |
| 2010/0002272 A1 | 1/2010 | Sato et al. |
| 2010/0022724 A1 | 1/2010 | Jacobsen et al. |
| 2010/0028299 A1 | 2/2010 | Einav et al. |
| 2010/0143301 A1 | 6/2010 | Desai et al. |
| 2011/0206607 A1 | 8/2011 | Olsson et al. |
| 2011/0293521 A1* | 12/2011 | Hyde .............. A61M 5/14244 424/9.1 |
| 2012/0041028 A1 | 2/2012 | Cooper et al. |
| 2012/0141471 A1 | 6/2012 | Salvino et al. |
| 2013/0216531 A1 | 8/2013 | Jain et al. |
| 2014/0275260 A1 | 9/2014 | Kawale, Sr. et al. |
| 2015/0004239 A1 | 1/2015 | Cullen et al. |
| 2015/0030561 A1 | 1/2015 | Dale et al. |
| 2015/0216843 A1 | 8/2015 | Fearon et al. |
| 2015/0246019 A1 | 9/2015 | Bridger et al. |
| 2015/0301058 A1 | 10/2015 | Schettini et al. |
| 2015/0352208 A1 | 12/2015 | Fearon et al. |
| 2016/0089385 A1 | 3/2016 | Sherman et al. |
| 2017/0090658 A1 | 3/2017 | Park et al. |
| 2017/0166591 A1 | 6/2017 | Ojima et al. |
| 2017/0234879 A1 | 8/2017 | Klinguer-Hamour et al. |
| 2018/0228894 A1 | 8/2018 | Fearon et al. |
| 2018/0369167 A1 | 12/2018 | Arbeit et al. |
| 2019/0030023 A1 | 1/2019 | Arbeit et al. |
| 2019/0083485 A1 | 3/2019 | Arbeit et al. |
| 2019/0160051 A1 | 5/2019 | Arbeit et al. |
| 2019/0322671 A1 | 10/2019 | Bourque et al. |
| 2020/0123150 A1 | 4/2020 | Bourque et al. |
| 2020/0138804 A1 | 5/2020 | Parasuraman et al. |

FOREIGN PATENT DOCUMENTS

| | | |
|---|---|---|
| WO | WO-1999004794 | 2/1999 |
| WO | WO-1999031264 | 6/1999 |
| WO | WO-2000002870 | 1/2000 |
| WO | WO-2000022599 | 4/2000 |
| WO | WO-2000045814 | 8/2000 |
| WO | WO-2000056729 | 9/2000 |
| WO | WO-2002022600 | 3/2002 |
| WO | WO-2002034745 | 5/2002 |
| WO | WO-2002076948 | 10/2002 |
| WO | WO-2003011277 | 2/2003 |
| WO | WO-2003055876 | 7/2003 |
| WO | WO-2004019973 | 3/2004 |
| WO | 2004093817 | 11/2004 |
| WO | WO-2004106493 | 12/2004 |
| WO | WO-2006026703 | 3/2006 |
| WO | WO-2006036816 | 4/2006 |
| WO | WO-2006096444 | 9/2006 |
| WO | WO-2006138259 | 12/2006 |
| WO | 2007008539 | 1/2007 |
| WO | 2007022523 A2 | 2/2007 |
| WO | WO-2007027999 | 3/2007 |
| WO | 2007087548 | 8/2007 |
| WO | WO-2007087549 | 8/2007 |
| WO | WO-2009026251 | 2/2009 |
| WO | 2009117706 A2 | 9/2009 |
| WO | 2011147026 | 12/2011 |
| WO | 2012049277 | 4/2012 |
| WO | WO-2012075362 | 6/2012 |
| WO | 2012094703 | 7/2012 |
| WO | WO-2015030853 | 3/2015 |
| WO | WO-2015038887 | 3/2015 |
| WO | WO-2015069770 | 5/2015 |
| WO | WO-2015143012 | 9/2015 |
| WO | 2015200341 | 12/2015 |
| WO | WO-2016008976 | 1/2016 |
| WO | 2016090434 A1 | 6/2016 |
| WO | 2016146261 | 9/2016 |
| WO | WO-2016201425 | 12/2016 |
| WO | 2017048702 | 3/2017 |
| WO | WO-2017106328 | 6/2017 |
| WO | WO-2017106332 | 6/2017 |
| WO | WO-2017112894 | 6/2017 |
| WO | WO-2017127811 | 7/2017 |
| WO | 2017177230 | 10/2017 |
| WO | 2017181073 | 10/2017 |
| WO | 2017223229 | 12/2017 |
| WO | 2017223239 | 12/2017 |
| WO | 2017223243 | 12/2017 |
| WO | WO-2018237158 | 12/2018 |
| WO | 2019094392 | 5/2019 |
| WO | 2019126106 A1 | 6/2019 |
| WO | 2019200223 | 10/2019 |

OTHER PUBLICATIONS

"Q3C—Tables and Lists, Guidance for Industry," U.S. Department of Health and Human Services, Food and Drug Adminstration, Center for Drug Evaluation and Research, Center for Biologics Evaluation and Research, Aug. 2018, https://www.fda.gov/downloads/Drugs/GuidanceComplianceRegulatoryInformation/Guidances/UCM073395.pdf. Date Accessed Jan. 22, 2019 (10 pages).

"Therapeutics," Encyclopedia Britannica Online, 2018, https://www.britannica.com/science/therapeutics. Date Accessed, Nov. 6, 2018 (1 page).

"WMA Declaration of Helsinki—Ethical Principles for Medical Research Involving Human Subjects," amended Oct. 2013, http://www.wma.net/en/30publications/10policies/b3/. Date Accessed Apr. 6, 2015 (4 Pages).

Abi-Younes et al., "The Stromal Cell-Derived Factor-1 Chemokine Is a Potent Platelet Agonist Highly Expressed in Atherosclerotic Plaques," Circulation Research, vol. 86, Feb. 4, 2000 (pp. 131-138).

Acharyya et al.,"CXCL1 paracrine network links cancer chemoresistance and metastasis." Cell, vol. 150, No. 1, 2012 (pp. 165-178).

Aduro Biotech, Inc., "Safety and Efficacy of MIW815 (ADU-S100) +/− Ipilimumab in Patients With Advanced/Metastatic Solid Tumors

(56) References Cited

OTHER PUBLICATIONS or Lymphomas," ClinicalTrials.gov: NCT02675439, First Posted: Feb. 5, 2016, Last Update: Sep. 26, 2018, https://clinicaltrials.gov/ct2/show/study/NCT02675439. Date Accessed, Mar. 18, 2019 (6 pages).

Aeglea Biotherapeutics, "A Multiple Dose, Dose Escalation Trial of AEB1102 in Patients With Advanced Solid Tumors," ClinicalTrials.gov: NCT02561234, First Posted: Sep. 28, 2015, Last Update: Mar. 22, 2019, https://clinicaltrials.gov/ct2/show/study/NCT02561234. Date Accessed, Mar. 25, 2019 (6 pages).

Aeglea Biotherapeutics, "A Multiple Dose, Dose Escalation Trial of AEB1102 in Patients With AML or MDS," ClinicalTrials.gov: NCT02732184, First Posted: Apr. 8, 2016, Last Update: Oct. 17, 2018, https://clinicaltrials.gov/ct2/show/study/NCT02732184. Date Accessed, Mar. 25, 2019 (6 pages).

Agenus Inc., "AGEN-1884, an Anti-CTLA-4 Antibody, in Advanced Solid Cancers," ClinicalTrials.gov: NCT02694822, First Posted: Mar. 1, 2016, Last Update: Jun. 27, 2017, https://clinicaltrials.gov/ct2/show/study/NCT02694822. Date Accessed, Mar. 25, 2019 (7 pages).

Aileron Therapeutics, "ALRN-6924 in Patients With Advanced Solid Tumors or Lymphomas," ClinicalTrials.gov: NCT02264613, First Posted: Oct. 15, 2014, Last Update: Jun. 27, 2017, https://clinicaltrials.gov/ct2/show/study/NCT02264613. Date Accessed, Mar. 25, 2019 (7 pages).

Aileron Therapeutics, "Safety Study of ALRN-6924 in Patients With Acute Myeloid Leukemia or Advanced Myelodysplastic Syndrome," ClinicalTrials.gov: NCT02909972, First Posted: Sep. 21, 2016, Last Update: Jun. 27, 2017, https://clinicaltrials.gov/ct2/show/study/NCT02909972. Date Accessed, Mar. 25, 2019 (7 pages).

ALX Oncology Inc., "A Study of ALX148 in Patients With Advanced Solid Tumors and Lymphoma," ClinicalTrials.gov: NCT03013218, First Posted: Jan. 6, 2017, Last Update: Aug. 8, 2018, https://clinicaltrials.gov/ct2/show/study/NCT03013218. Date Accessed, Mar. 18, 2019 (6 pages).

Ami and Horui, "Lipase-catalyzed Kinetic Resolution of (±)-trans and cis-2-Azidocycloalkanols," Bioscience, Biotechnology, Biochemistry, vol. 63, No. 12, 1999 (pp. 2150-2156).

An et al., "Solution phase combinatorial chemistry. Discovery of 13- and 15-membered polyazapyridinocyclophane libraries with antibacterial activity," Tetrahedron, vol. 54, (pp. 3999-4012).

Arenburg et al., "The role of CXC chemokines in the regulation of angiogenesis in non-small cell lung cancer," Journal of Leukocyte Biology, vol. 62, 1997 (pp. 554-562).

Auiti et al., "The Chemokine SDF-1 is a Chemoattractant for Human CD34+ Hematopoietic Progenitor Cells and Provides a New Mechanism to Explain the Mobilization of CD34+ Progenitors to Peripheral Blood," Journal of Experimental Medicine, vol. 185, No. 1, Jan. 6, 1997 (pp. 111-120).

Ayers et al., "IFN-γ-related mRNA profile predicts clinical response to PD-1 blockade," The Journal of Clinical Investigation, vol. 127, No. 8, 2017 (pp. 2930-2940).

Baggiolini, "Chemokines and leukocyte traffic," Nature, vol. 392, Apr. 9, 1998 (pp. 565-568).

Balabanian, et al., "Proper desensitization of CXCR4 is required for lymphocyte development and peripheral compartmentalization in mice," Blood, vol. 119, No. 24, Mar. 2012 (pp. 5722-5730).

Balabanian, et al., "WHIM syndromes with different genetic anomalies are accounted for by impaired CXCR4 desensitization to CXCL12," Blood, vol. 105, No. 6, Mar. 15, 2005 (pp. 2449-2457).

Bayer, "Phase I Study of BAY1436032 in IDH1-mutant Advanced Solid Tumors," ClinicalTrials.gov: NCT02746081, First Posted: Apr. 21, 2016, Last Update: Mar. 19, 2019, https://clinicaltrials.gov/ct2/show/study/NCT02746081. Date Accessed, Mar. 25, 2019 (8 pages).

Beaussant-Cohen, et al., "Description and outcome of a cohort of 8 patients with WHIM syndrome from the French Severe Chronic Neutropenia Registry," Orphanet Journal of Rare Diseases, vol. 7, No. 71, Jun. 14, 2012 (pp. 5722-5730).

Berge et al., "Pharmaceutical Salts," Journal of Pharmaceutical Sciences, vol. 66, No. 1, Jan. 1977 (pp. 1-19).

Black et al., "In vivo HIV-1 infection of CD45RA+CD4+ T cells is established primarily by syncytium-inducing variants and correlates with the rate of CD4+ T cell decline," Proceedings of the National Academy of Sciences of the United States of America, vol. 97, No. 3, 2000 (pp. 1269-1274).

Blanchette, S., "NCT02823405: X4P-001 and Prembrolizumab in Patents With Advanced Melanoma (X4P-001-MELA)," Jul. 6, 2016, https://clinicaltrials.gov/ct2/show/NCT02823405> Date Accessed Oct. 5, 2018 (7 pages).

Blanco et al. "The CXCR4 Antagonist AMD3100 Efficiently Inhibits Cell-Surface-Expressed Human Immunodeficiency Virus Type 1 Envelope-Induced Apoptosis," Antimicrobial Agents and Chemotherapy, vol. 44, No. 1., Jan. 2000 (pp. 51-56).

Bleul et al., "B Lymphocyte Chemotaxis Regulated in Association with Microanatomic Localization, Differentiation State, and B Cell Receptor Engagement," Journal of Experimental Medicine, vol. 187, No. 5, Mar. 2, 1998 (pp. 753-762).

Bohinjec, "Myelokathexis: chronic neutropenia with hyperplastic bone marrow and hypersegmented neutrophils in two siblings," Blut, vol. 42, 1981 (pp. 191-196).

Bristol-Myers Squibb, "A Phase I Open Label Study of the Safety and Tolerability of Elotuzumab (BMS-901608) Administered in Combination With Either Lirilumab (BMS-986015) or Urelumab (BMS-663513) in Subjects With Multiple Myeloma," ClinicalTrials.gov: NCT02252263, First Posted: Sep. 30, 2014, Last Update: Nov. 1, 2017, https://clinicaltrials.gov/ct2/show/study/NCT02252263. Date Accessed, Mar. 18, 2019 (7 pages).

Bristol-Myers Squibb, "An Investigational Immuno-therapy Study of Experimental Medication BMS-986178 by Itself or in Combination With Nivolumab and/or Ipilimumab in Patients With Solid Cancers That Are Advanced or Have Spread," ClinicalTrials.gov: NCT02737475, First Posted: Apr. 14, 2016, Last Update: Jan. 31, 2019, https://clinicaltrials.gov/ct2/show/study/NCT02737475. Date Accessed, Mar. 18, 2019 (11 pages).

Bristol-Myers Squibb, "An Investigational Immuno-therapy Study of Experimental Medication BMS-986179 Given Alone and in Combination With Nivolumab," ClinicalTrials.gov: NCT02754141, First Posted: Apr. 28, 2016, Last Update: Feb. 1, 2019, https://clinicaltrials.gov/ct2/show/study/NCT02754141. Date Accessed, Mar. 18, 2019 (8 pages).

Bristol-Myers Squibb, "An Investigational Immuno-Therapy Study to Determine the Safety and Effectiveness of Nivolumab and Daratumumab in Patients With Multiple Myeloma," ClinicalTrials.gov: NCT01592370, First Posted: May 7, 2012, Last Update: Jan. 15, 2019, https://clinicaltrials.gov/ct2/show/study/NCT01592370. Date Accessed, Mar. 18, 2019 (9 pages).

Bristol-Myers Squibb, "An Investigational Immuno-therapy Study to Evaluate the Safety and Effectiveness of Experimental Medication BMS-986207 by Itself and in Combination With Nivolumab in Solid Cancers That Are Advanced or Have Spread," ClinicalTrials.gov: NCT02913313, First Posted: Sep. 23, 2016, Last Update: Jan. 31, 2019, https://clinicaltrials.gov/ct2/show/study/NCT02913313. Date Accessed, Mar. 25, 2019 (9 pages).

Bristol-Myers Squibb, "An Investigational Immuno-therapy Study to Investigate the Safety and Effectiveness of Nivolumab, and Nivolumab Combination Therapy in Virus-associated Tumors (CheckMate358)," ClinicalTrials.gov: NCT02488759, First Posted: Jul. 2, 2015, Last Update: Oct. 19, 2018, https://clinicaltrials.gov/ct2/show/study/NCT02488759. Date Accessed Nov. 29, 2018 (7 pages).

Broxmeyer et al., "Effects of in vivo treatment with PIXY321 (GM-CSF/IL-3 fusion protein) on proliferation kinetics of bone marrow and blood myeloid progenitor cells in patients with sarcoma," Experimental Hematology, vol. 23, 1995 (pp. 335-340).

Broxmeyer, "A WHIM satisfactorily addressed," Blood, vol. 123, No. 15, 2014 (pp. 2286-2288).

Burger et al., "Chronic Lymphocytic Leukemia B Cells Express Functional CXCR4 Chemokine Receptors That Mediate Spontaneous Migration Beneath Bone Marrow Stromal Cells," Blood, vol. 94, No. 11, Dec. 1, 1999 (pp. 3658-3667).

(56) References Cited

OTHER PUBLICATIONS

Canadian Cancer Trials Group, "Reolysin Combined With Docetaxel and Prednisone or Docetaxel and Prednisone Alone in Metastatic Castration Resistant Prostate Cancer," ClinicalTrials.gov: NCT01619813, First Posted: Jun. 14, 2012, Last Update: Jan. 23, 2019, https://clinicaltrials.gov/ct2/show/study/NCT01619813. Date Accessed, Mar. 25, 2019 (8 pages).

Canadian Cancer Trials Group, "Reolysin in Combination With FOLFOX6 and Bevacizumab or FOLFOX6 and Bevacizumab Alone in Metastatic Colorectal Cancer," ClinicalTrials.gov: NCT01622543 First Posted: Jun. 19, 2012, Last Update: Feb. 1, 2018, https://clinicaltrials.gov/ct2/show/study/NCT01622543. Date Accessed, Mar. 25, 2019 (8 pages).

Cao, et al., "Effect of Low-Dose Ritonavir on the Pharmacokinetics of the CXCR4 Antagonist AMD070 in Healthy Volunteers," Antimicrobial Agents and Chemotherpy, vol. 52, No. 5, 2008 (pp. 1630-1634).

Catalano, J. G. et al., "Synthesis of a novel tricyclic 1, 2,3,4, 4a, 5,, 10b-octahydro-1, 10-phenanthroline ring system and CXCR4 antagonists with potent activity against HIV-1," Bioorganic & Medicinal Chemistry Letters, vol. 20, 2010 (pp. 2186-2190).

Celgene, "A Safety and Efficacy Study of Oral AG-120 Plus Subcutaneous Azacitidine and Oral AG-221 Plus Subcutaneous Azacitidine in Subjects With Newly Diagnosed Acute Myeloid Leukemia (AML)," ClinicalTrials.gov: NCT02677922, First Posted: Feb. 9, 2016, Last Update: Feb. 21, 2019, https://clinicaltrials.gov/ct2/show/study/NCT02677922. Date Accessed, Mar. 20, 2019 (11 pages).

Celgene, "A Study of CC-90002 in Subjects With Acute Myeloid Leukemia (AML) and High-risk Myelodysplastic Syndrome (MDS)," ClinicalTrials.gov: NCT02641002, First Posted: Dec. 29, 2015, Last Update: Oct. 18, 2018, https://clinicaltrials.gov/ct2/show/study/NCT02641002. Date Accessed, Mar. 18, 2019 (7 pages).

Celgene, "An Efficacy and Safety Study of AG-221 (CC-90007) Versus Conventional Care Regimens in Older Subjects With Late Stage Acute Myeloid Leukemia Harboring an Isocitrate Dehydrogenase 2 Mutation (IDHENTIFY)," ClinicalTrials.gov: NCT02577406, First Posted: Oct. 16, 2015, Last Update: Feb. 21, 2019, https://clinicaltrials.gov/ct2/show/study/NCT02577406. Date Accessed, Mar. 25, 2019 (12 pages).

Celldex Therapeutics, "A Dose Escalation and Cohort Expansion Study of Anti-CD27 (Varlilumab) and Anti-PD-1 (Nivolumab) in Advanced Refractory Solid Tumors," ClinicalTrials.gov: NCT02335918, First Posted: Jan. 12, 2015, Last Update: Jan. 7, 2019, https://clinicaltrials.gov/ct2/show/study/NCT02335918. Date Accessed, Mar. 18, 2019 (9 pages).

Celldex Therapeutics, "A Study of CDX-1127 (Varlilumab) in Patients With Select Solid Tumor Types or Hematologic Cancers," ClinicalTrials.gov: NCT01460134, First Posted: Oct. 26, 2011, Last Update: Jan. 31, 2018, https://clinicaltrials.gov/ct2/show/study/NCT01460134. Date Accessed, Mar. 18, 2019 (9 pages).

Centre Leon Berard, "Evaluation of Safety and Activity of an Anti-PDL1 Antibody (DURVALUMAB) Combined With CSF-1R TKI (PEXIDARTINIB) in Patients With Metastatic/Advanced Pancreatic or Colorectal Cancers (MEDIPLEX)," ClinicalTrials.gov: NCT02777710, First Posted: May 19, 2016, Last Update Jan. 17, 2019, https://clinicaltrials.gov/ct2/show/study/NCT02777710. Date Accessed, Mar. 18, 2019 (10 pages).

Chen et al., "CXCR4 inhibition in tumor microenvironmental facilitates anti-programmed death receptor-1 immunotherapy in sorafenib-treated hepatocellular carcinoma in mice," Hepatology, vol. 61, No. 5, May 2015, (pp. 1591-1602).

Clark, PE., "Rationale for targeted therapies and potential role of pazopanib in advanced renal cell carcinoma," Biologics: Targets and Therapy, vol. 4, Jun. 26, 2010 (pp. 187-197).

Cold Genesys, Inc., "Safety and Efficacy of CG0070 Oncolytic Virus Regimen for High Grade NMIBC After BCG Failure (BOND2)," ClinicalTrials.gov: NCT02365818, First Posted: Feb. 19, 2015, Last Update: Mar. 20, 2019, https://clinicaltrials.gov/ct2/show/study/NCT02365818. Date Accessed, Mar. 25, 2019 (9 pages).

Comba et al., "Catalytic Aziridination of Styrene with Copper Complexes for Substituted 3,7-Diazabicyclo[3.3.1]nonanones," European Journal of Inorganic Chemistry, vol. 9, 2003 (pp. 1711-1718).

Connolly et al., "Complexities of TGF-β Targeted Cancer Therapy," (2012) International Journal of Biological Sciences vol. 8, No. 7, Jul. 2012 (pp. 964-978).

Connor et al., "Human Immunodeficiency Virus Type 1 Variants with Increased Replicative Capacity Develop during the Asymptomatic Stage before Disease Progression," Journal of Virology, vol. 68, No. 7, 1994 (pp. 4400-4408).

Crawford et al., "AMD070, a CXCR4 Chemokine Receptor Antagonist: Practical Large-Scale Laboratory Synthesis," Organic Process Research and Development, vol. 12, No. 5, 2008 (pp. 823-830).

Crump et al., "Solution structure and basis for functional activity of stromal cell derived factor-1; dissociation of CXCR4 activation from binding and inhibition of HIV-1," The EMBO Journal, vol. 16, No. 23, 1997 (pp. 6996-7007).

D' Alterio, et al., "Inhibition of stromal CXCR4 impairs development of lung metastases," Cancer Immunology, Immunotherapy, vol. 61, 2012 (pp. 1713-1720).

Dale et al., "Effects of Granulocyte-Macrophage Colony-Stimulating Factor (GM-CSF) on Neutrophil Kinetics and Function in Normal Human Volunteers," American Journal of Hematology, (1998), vol. 57, 1998 (pp. 7-15).

Dale et al., "The CXCR4 antagonist plerixafor is a potential therapy for myelokathexis, WHIM syndrome," Blood, vol. 118, No. 18, Nov. 3, 2011 (pp. 4963-4966).

Dale et al., "The Severe Chronic Neutropenia International Registry: 10-Year Follow-up Report," Supportive Cancer Therapy. vol. 3, No. 4, 2006 (pp. 220-231).

Dana-Farber Cancer Institute, "LY3022855 With BRAF/MEK Inhibition in Patients With Melanoma," ClinicalTrials.gov: NCT03101254, First Posted: Apr. 5, 2017, Last Update: Feb. 4, 2019, https://clinicaltrials.gov/ct2/show/study/NCT03101254. Date Accessed, Mar. 18, 2019 (9 pages).

Debnath et al., "Small molecule inhibitors of CXCR4," Theranostics, vol. 3, No. 1, Jan. 15, 2013 (pp. 47-75).

Doranz, "Chemokine receptors as fusion cofactors for human immunodeficiency virus type 1 (HIV-1)," Immunologic Research, vol. 16, 1997 (pp. 15-28).

Dorwald, "Side Reactions in Organic Synthesis," Wiley: VCH, Weinheim, 2005 (p. IX of preface and pp. 1-15, 41).

Dotta et al., "Clinical and genetic features of warts, hypogammaglobulinemia, infections and myelokathexis (WHIM) syndrome," Current Molecular Medicine, vol. 11, 2011 (pp. 317-325).

Duda et al., "CXCL12 (SDF1a)-CXCR4/CXCR7 Pathway Inhibition: An Emerging Sensitizer for Anticancer Therapies?," Clinical Cancer Research, vol. 17, No. 8, 2011 (pp. 2074-2080).

Egberink et al., "Bicyclams, Selective Antagonists of the Human Chemokine Receptor CXCR4, Potently Inhibit Feline Immunodeficiency Virus Replication," Journal of Virology, vol. 73, No. 8, 1999 (pp. 6346-6352).

Eli Lilly and Company, "A Study of LY3022855 in Combination With Durvalumab or Tremelimumab in Participants With Advanced Solid Tumors," ClinicalTrials.gov: NCT02718911, First Posted: Mar. 24, 2016, Last Update Jan. 15, 2019, https://clinicaltrials.gov/ct2/show/study/NCT02718911. Date Accessed, Mar. 18, 2019 (7 pages).

Eli Lilly and Company, "A Study of LY3321367 Alone or With LY3300054 in Participants With Advanced Relapsed/Refractory Solid Tumors," ClinicalTrials.gov: NCT03099109, First Posted: Apr. 4, 2017, Last Update: Mar. 5, 2019, https://clinicaltrials.gov/ct2/show/study/NCT03099109. Date Accessed, Mar. 25, 2019 (10 pages).

EMD Serono Research & Development Institute, Inc., "MSB0011359C (M7824) in Metastatic or Locally Advanced Solid Tumors," ClinicalTrials.gov: NCT02517398, First Posted: Aug. 7, 2015, Last Update: Nov. 19, 2018, https://clinicaltrials.gov/ct2/show/study/NCT02517398. Date Accessed, Mar. 25, 2019 (8 pages).

Facciabene et al., "Tumour hypoxia promotes tolerance and angiogenesis via CCL28 and Treg cells," Nature, vol. 475, 2011 (pp. 226-230).

(56) References Cited

OTHER PUBLICATIONS

Fedyk et al., "Maturation decreases responsiveness of human bone marrow B lineage cells to stromal-derived factor 1 (SDF-1)," Journal of Leukocyte Biology, vol. 66, Oct. 1999 (pp. 667-673).
Feig et al., "Targeting CXCL12 from FAP-expressing carcinoma-associated fibroblasts synergizes with anti-PD-L1 immunotherapy in pancreatic cancer," PNAS, vol. 110, No. 50, 2013 (pp. 20212-20217).
Finke J. et al., "MDSC as a mechanism of tumor escape from sunitinib mediated anti-angiogenic therapy," International Immunopharmacology, vol. 11, No. 7, Jul. 2011 (pp. 856-861).
Forty Seven, Inc., "CAMELLIA: Anti-CD47 Antibody Therapy in Haematological Malignancies," ClinicalTrials.gov: NCT02678338, First Posted: Feb. 9, 2016, Last Update: Feb. 21, 2019, https://clinicaltrials.gov/ct2/show/study/NCT02678338. Date Accessed, Mar. 18, 2019 (5 pages).
Forty Seven, Inc., "Trial of Hu5F9-G4 in Combination With Cetuximab in Patients With Solid Tumors and Advanced Colorectal Cancer," ClinicalTrials.gov: NCT02953782, First Posted: Nov. 3, 2016, Last Update: Aug. 1, 2018, https://clinicaltrials.gov/ct2/show/study/NCT02953782. Date Accessed, Mar. 18, 2019 (7 pages).
Forty Seven, Inc., "Trial of Hu5F9-G4 in Combination With Rituximab in Relapsed/Refractory B-cell Non-Hodgkin's Lymphoma," ClinicalTrials.gov: NCT02953509, First Posted: Nov. 2, 2016, Last Update: Feb. 8, 2019, https://clinicaltrials.gov/ct2/show/study/NCT02953509. Date Accessed, Mar. 18, 2019 (8 pages).
Gacche, RN. "Compensatory angiogenesis and tumor refractoriness," Oncogenesis, vol. 4, e153, Jun. 1, 2015 (8 pages).
Gale et al., "Chemokines: extracellular messengers for all occasions?," BioEssays, vol. 21, 1999 (pp. 17-28).
Galsky et al., "A Phase I Trial of LY2510924, a CXCR4 Peptide Antagonist, in Patients with Advanced Cancer," Clinical Cancer Research, vol. 20, No. 16, Aug. 15, 2014 (pp. 3581-3588; 4414).
Genelux Corporation, "GL-ONC1 Oncolytic Immunotherapy in Patients With Recurrent or Refractory Ovarian Cancer," ClinicalTrials.gov: NCT02759588, First Posted: May 3, 2016, Last Update: Nov. 8, 2018, https://clinicaltrials.gov/ct2/show/study/NCT02759588. Date Accessed, Mar. 25, 2019 (8 pages).
Genelux GmbH, "A Study of GL-ONC1, an Oncolytic Vaccinia Virus, in Patients With Advanced Peritoneal Carcinomatosis," ClinicalTrials.gov: NCT01443260, First Posted: Sep. 29, 2011, Last Update: Mar. 10, 2015, https://clinicaltrials.gov/ct2/show/study/NCT01443260. Date Accessed, Mar. 25, 2019 (6 pages).
Genzyme, a Sanofi Company, "Safety and Efficacy Study of GC1008 to Treat Renal Cell Carcinoma or Malignant Melanoma," ClinicalTrials.gov: NCT00356460, First Posted: Jul. 26, 2006, Last Update: Mar. 19, 2014, https://clinicaltrials.gov/ct2/show/study/NCT00356460. Date Accessed, Mar. 25, 2019 (10 pages).
Glaspy et al., "Peripheral Blood Progenitor Cell Mobilization Using Stem Cell Factor in Combination With Filgrastim in Breast Cancer Patients," Blood, vol. 90, 1997 (pp. 2939-2951).
GlaxoSmithKline, "Dose Escalation and Expansion Study of GSK3359609 in Subjects With Selected Advanced Solid Tumors (INDUCE-1)," ClinicalTrials.gov: NCT02723955, First Posted: Mar. 31, 2016, Last Update: Feb. 25, 2019, https://clinicaltrials.gov/ct2/show/study/NCT02723955. Date Accessed, Mar. 18, 2019 (25 pages).
GlaxoSmithKline, "GSK3174998 Alone or With Pembrolizumab in Subjects With Advanced Solid Tumors (ENGAGE-1)," ClinicalTrials.gov: NCT02528357, First Posted: Aug. 19, 2015, Last Update: Jun. 1, 2018, https://clinicaltrials.gov/ct2/show/study/NCT02528357. Date Accessed, Mar. 18, 2019 (11 pages).
Gonzalo et al., "Critical Involvement of the Chemotactic Axis CXCR4/Stromal Cell-Derived Factor-1α in the Inflammatory Component of Allergic Airway Disease," Journal of Immunology, vol. 165, No. 1, Jul. 1, 2000 (pp. 499-508).
Gudmundsson, K.S., "Amine sustituted N-(1H-benzimidazol-2ylmethyl)-5,6,7,8-tetrahydro-8-quino-linamines as CXCR4 antagonists with potent activity against HIV-1," Bioorganic & Medicinal Chemistry Letters, 2009 (pp. 1-5).

Gulino et al., "Altered leukocyte response to CXCL12 in patients with warts hypogammaglobulinemia, infections, myelokathexis (WHIM) syndrome," Blood, vol. 104, No. 2, 2014 (pp. 444-452).
H. Lee Moffitt Cancer Center and Research Institute, "Combining PD-1 Blockade, CD137 Agonism and Adoptive Cell Therapy for Metastatic Melanoma," ClinicalTrials.gov: NCT02652455, First Posted: Jan. 11, 2016, Last Update: Dec. 4, 2018, https://clinicaltrials.gov/ct2/show/study/NCT02652455. Date Accessed, Mar. 18, 2019 (9 pages).
Hendrix et al., "Pharmacokinetics and safety of AMD-3100, a novel antagonist of the CXCR-4 chemokine receptor, in human volunteers," Antimicrobial Agents and Chemotherapy, vol. 44, No. 6, Jun. 2000 (pp. 1667-1673).
Hendrix, et al., "Safety, Pharmacokinetics, and Antiviral Activity of AMD3100, a Selective CXCR4 Receptor Inhibitor, in HIV-1 Infection," Journal of Acquired Immune Deficiency Syndrome, vol. 37, No. 2. Oct. 1, 2004 (pp. 1253-1262).
Hernandez et al., "Mutations in the chemokine receptor gene CXCR4 are associated with WHIM syndrome, a combined immunodeficiency disease," Nature Genetics, vol. 34, No. 1., May 31, 2003 (pp. 70-74).
Hesselgesser et al., "CD-4-independent association between HIV-1 gp120 and CXCR4: functional chemokine receptors are expressed in human neurons," Current Biology, vol. 7, No. 2, Jan. 21, 1997 (pp. 112-121).
Hesselgesser et al., "Neuronal apoptosis inducted by HIV-1 gp120 and chemokine SDF-1α is mediated by the chemokine receptor CXCR4," Current Biology, vol. 8, No. 10, Apr. 27, 1998 (pp. 595-598).
Highfill et al., "Disruption of CXCR2-mediated MDSC tumor trafficking enhances anti-PD1 efficacy," Science Translational Medicine, vol. 6, No. 237, May 21, 2014 (pp. 1-13).
Husain Z. et al., "Tumor-derived lactate modifies antitumor immune response: Effect on myeloid-derived suppressor cells and NK cells," Journal of Immunology, vol. 191, 2013 (pp. 1486-1495).
Immutep Australia Pty. Ltd., "Phase 1 Study of IMP321 (Eftilagimod Alpha) Adjuvant to Anti-PD-1 Therapy in Unresectable or Metastatic Melanoma (TACTI-mel)," ClinicalTrials.gov: NCT02676869, First Posted: Feb. 8, 2016, Last Update: Jan. 11, 2019, https://clinicaltrials.gov/ct2/show/study/NCT02676869. Date Accessed, Mar. 25, 2019 (6 pages).
Immutep S.A., "IMP321 (Eftilagimod Alpha) as Adjunctive to a Standard Chemotherapy Paclitaxel Metastatic Breast Carcinoma," ClinicalTrials.gov: NCT02614833, First Posted: Nov. 25, 2015, Last Update: Mar. 18, 2019, https://clinicaltrials.gov/ct2/show/study/NCT02614833. Date Accessed, Mar. 25, 2019 (9 pages).
Immutep S.A., "IMP321 Plus First-line Paclitaxel in Metastatic Breast Carcinoma," ClinicalTrials.gov: NCT00349934, First Posted: Jul. 10, 2006, Last Update Jan. 7, 2010, https://clinicaltrials.gov/ct2/show/study/NCT00349934. Date Accessed, Mar. 25, 2019 (7 pages).
Incyte Biosciences International Sàrl, "An Open-Label, Dose-Escalation, Safety Study of INCAGN01876 in Subjects With Advanced or Metastatic Solid Tumors," ClinicalTrials.gov: NCT02697591, First Posted: Mar. 3, 2016, Last Update: Oct. 31, 2018, https://clinicaltrials.gov/ct2/show/study/NCT02697591. Date Accessed, Mar. 18, 2019 (6 pages).
Incyte Biosciences International Sàrl, "Phase 1/2 Study Exploring the Safety, Tolerability, and Efficacy of INCAGN01876 Combined With Immune Therapies in Advanced or Metastatic Malignancies," ClinicalTrials.gov: NCT03126110, First Posted: Apr. 24, 2017, Last Update: Dec. 10, 2018, https://clinicaltrials.gov/ct2/show/study/NCT03126110. Date Accessed, Mar. 18, 2019 (7 pages).
Innate Pharma, "Combination Study of IPH2201 With Ibrutinib in Patients With Relapsed, Refractory or Previously Untreated Chronic Lymphocytic Leukemia," ClinicalTrials.gov: NCT02557516, First Posted: Sep. 23, 2015, Last Update: Apr. 24, 2018, https://clinicaltrials.gov/ct2/show/study/NCT02557516. Date Accessed, Mar. 20, 2019 (6 pages).
Innate Pharma, "Efficacy Study of Anti-KIR Monoclonal Antibody as Maintenance Treatment in Acute Myeloid Leukemia (EFFIKIR) (EFFIKIR)," ClinicalTrials.gov: NCT01687387, First Posted: Sep.

(56) References Cited

OTHER PUBLICATIONS 18, 2012, Last Update: Feb. 8, 2019, https://clinicaltrials.gov/ct2/show/study/NCT01687387. Date Accessed, Mar. 18, 2019 (9 pages).
Innate Pharma, "Study of IPH4102 in Patients With Relapsed/Refractory Cutaneous T-cell Lymphomas (CTCL)," ClinicalTrials.gov: NCT02593045, First Posted: Oct. 30, 2015, Last Update: Feb. 12, 2019, https://clinicaltrials.gov/ct2/show/study/NCT02593045. Date Accessed, Mar. 18, 2019 (6 pages).
Innate Pharma, "Study of Monalizumab and Cetuximab in Patients With Recurrent or Metastatic Squamous Cell Carcinoma of the Head and Neck," ClinicalTrials.gov: NCT02643550, First Posted: Dec. 31, 2015, Last Update: Sep. 13, 2018, https://clinicaltrials.gov/ct2/show/study/NCT02643550. Date Accessed, Mar. 20, 2019 (9 pages).
Innate Pharma, "Study on the Anti-tumor Activity, Safety and Pharmacology of IPH2101 in Patients With Smoldering Multiple Myeloma (KIRMONO)," ClinicalTrials.gov: NCT01222286, First Posted: Oct. 18, 2010, Last Update: May 9, 2014, https://clinicaltrials.gov/ct2/show/study/NCT01222286. Date Accessed, Mar. 18, 2019 (7 pages).
Innate Pharma, "Study on the Safety, Anti-tumor Activity and Pharmacology of IPH2101 Combined With Lenalidomide in Patients With Multiple Myeloma Experiencing a First or Second Relapse (KIRIMID)," ClinicalTrials.gov: NCT01217203, First Posted: Oct. 8, 2010, Last Update: Feb. 28, 2014, https://clinicaltrials.gov/ct2/show/study/NCT01217203. Date Accessed, Mar. 18, 2019 (7 pages).
International Preliminary Examination Report for PCT/US2002/041407, titled "Chemokine Receptor Binding Heterocyclic Compounds with Enhanced Efficacy," dated Aug. 1, 2003 (4 pages).
International Preliminary Report on Patentability for PCT/US2004/015977, titled "Chemokine Receptor Binding Heterocyclic Compounds with Enhanced Efficacy," dated May 2, 2006 (4 pages).
International Search Report and Written Opinion issued by the United States Patent and Trademark Office as International Searching Authority for International Patent Application No. PCT/US2016/066634, dated Feb. 16, 2017 (15 pages).
International Search Report and Written Opinion issued by the United States Patent and Trademark Office as International Searching Authority for International Patent Application No. PCT/US2016/066639, dated Feb. 16, 2017 (11 pages).
International Search Report and Written Opinion issued by the United States Patent and Trademark Office as International Searching Authority for International Patent Application No. PCT/US2016/068394, dated Mar. 3, 2017 (10 pages).
International Search Report and Written Opinion issued by the United States Patent and Trademark Office as International Searching Authority for International Patent Application No. PCT/US2017/014578, dated Apr. 4, 2017 (12 pages).
International Search Report and Written Opinion issued by the United States Patent and Trademark Office as International Searching Authority for International Patent Application No. PCT/US2018/066141, dated Mar. 8, 2019 (8 pages).
International Search Report issued by the United States Patent and Trademark Office as International Searching Authority for International Patent Application No. PCT/US05/34491, dated Apr. 11, 2006 (2 pages).
International Search Report issued by the United States Patent and Trademark Office as International Searching Authority for International Patent Application No. PCT/US05/34950, dated Oct. 4, 2006 (4 pages).
International Search Report issued by the United States Patent and Trademark Office as International Searching Authority for International Patent Application No. PCT/US2002/029372, dated Aug. 10, 2004 (4 pages).
International Search Report issued by the United States Patent and Trademark Office as International Searching Authority for International Patent Application No. PCT/US2004/011328, dated Oct. 20, 2004 (2 pages).
International Search Report issued by the United States Patent and Trademark Office as International Searching Authority for International Patent Application No. PCT/US2004/012627, dated Jan. 13, 2005 (3 pages).
International Search Report issued by the United States Patent and Trademark Office as International Searching Authority for International Patent Application No. PCT/US2004/015977, dated Jul. 15, 2005 (3 pages).
International Search Report issued by the United States Patent and Trademark Office as International Searching Authority for International Patent Application No. PCT/US2005/08268, dated May 26, 2005 (3 pages).
Ishii et al., "Expression of Stromal Cell-Derived Factor-1/Pre-B Cell Growth-Stimulating Factor Receptor, CXC Chemokine Receptor 4, on CD34+ Human Bone Marrow Cells is a Phenotypic Alteration for Committed Lymphoid Progenitors," The Journal of Immunology, vol. 163, 1999 (pp. 3612-3620).
Iwakura et al., "AMD-3100, a CXCR4 Antagonist, Augments Incorporation of Bone Marrow-Derived Eendothelial Progenitor Cells into Sites of Myocardial Neovascularization," Abstract # 1127, Poster Board #-Session: 293I, Blood, vol. 100, No. 11, Nov. 16, 2002 (pp. 293A-294A).
Jackson et al., "Regeneration of ischemic cardiac muscle and vascular endothelium by adult stem cells," The Journal of Clinical Investigation, vol. 107, No. 1, Jun. 2011 (pp. 1395-1402).
Jennerex Biotherapeutics, "A Study of Recombinant Vaccinia Virus to Treat Malignant Melanoma," ClinicalTrials.gov: NCT00429312, First Posted: Jan. 31, 2007, Last Update: Jan. 15, 2015, https://clinicaltrials.gov/ct2/show/study/NCT00429312. Date Accessed, Mar. 25, 2019 (7 pages).
Jounce Therapeutics, Inc., "JTX-2011 Alone and in Combination With Anti-PD-1 or Anti-CTLA-4 in Subjects With Advanced and/or Refractory Solid Tumors (ICONIC)," ClinicalTrials.gov: NCT02904226, First Posted: Sep. 16, 2016, Last Update: Jun. 28, 2018, https://clinicaltrials.gov/ct2/show/study/NCT02904226. Date Accessed, Mar. 18, 2019 (11 pages).
Kawai et al., "Enhanced function with decreased internalization of carboxy-terminus truncated CXCR4 responsible for WHIM syndrome," Experimental Hematology, vol. 33, 2005 (pp. 460-468).
Kawai et al., "WHIM syndrome myelokathexis reproduced in the NOD/SCID mouse xenotransplant model engrafted with healthy human stem cells transduced with C-terminus-truncated CXCR4," Blood, vol. 109, No. 1, Jan. 1, 2007 (pp. 78-84), Epub Aug. 31, 2006.
Kawai et al., "WHIM syndrome: congenital immune deficiency disease," Current Opinion in Hematology, vol. 16, No. 1, Jan. 2009 (pp. 20-26).
Kim, et al., "CXCR4 signaling regulates metastasis of chemoresistant melanoma cells by a lymphatic metastatic niche," Cancer Research, vol. 70, No. 24, 2010 (pp. 10411-10421).
King, A. G. et al. "Rapid Mobilization of Murine Hematopoietic Stem Cells With Enhanced Engraftment Properties and Evaluation of Hematopoietic Progenitor Cell Mobilization in Rhesus Monkeys by a Single Injection of SB-251353, a Specific Truncated Form of the Human CXC Chemokine GROI3," Blood, vol. 97, No. 6, 2001 (pp. 1534-1542).
Kirkland et al., "Quantitation of Mafosfamide-Resistant Pre-Colony-Forming Units in Allogeneic Bone Marrow Transplantation: Relationship With Rate of Engraftment and Evidence for Long-Lasting Reduction in Stem Cell Numbers," Blood, vol. 87, No. 9, 1996 (pp. 3963-3969).
Kocher et al. "Neovascularization of ischemic myocardium by human bone-marrow-derived angioblasts prevents cardiomyocyte apoptosis, reduces remodeling and improves cardiac function," Nature Medicine, vol. 7, 2001 (pp. 430-436).
Lagane et al., "CXCR4 dimerization and beta-arrestin-mediated signaling account for the enhanced chemotaxis to CXCL12 in WHIM syndrome," Blood, vol. 112, No. 1, Jul. 1, 2008 (pp. 34-44).
Lapidot et al., "Current understanding of stem cell mobilization the roles of chemokines, proteolytic enzymes, adhesion molecules, cytokines, and stromal cells," Experimental Hematology, vol. 30, 2002, (pp. 973-981).

(56) References Cited

OTHER PUBLICATIONS

Lapidot et al., "The essential roles of the chemokine SDF-1 and its receptor CXCR4 in human stem cell homing and repopulation of transplanted immune-deficient NOD/SCID and NOD/SCID/B2m(null) mice," Leukemia, vol. 16, 2002 (pp. 1992-2003).
Lataillade et al., "Chemokine SDF-1 enhances circulating CD341 cell proliferation in synergy with cytokines: possible role in progenitor survival," Blood, vol. 95, No. 3., 1999 (pp. 756-768).
Leap Therapeutics, Inc., "Phase 1 Open-label Study of TRX518 Monotherapy and TRX518 in Combination With Gemcitabine, Pembrolizumab, or Nivolumab," ClinicalTrials.gov: NCT02628574, First Posted: Dec. 11, 2015, Last Update: Jan. 17, 2018, https://clinicaltrials.gov/ct2/show/study/NCT02628574. Date Accessed, Mar. 18, 2019 (8 pages).
Leap Therapeutics, Inc., "Trial of TRX518 (Anti-GITR mAb) in Stage III or IV Malignant Melanoma or Other Solid Tumors (TRX518-001)," ClinicalTrials.gov: NCT01239134, First Posted: Nov. 11, 2010, Last Update: Aug. 14, 2018, https://clinicaltrials.gov/ct2/show/study/NCT01239134. Date Accessed, Mar. 18, 2019 (8 pages).
Lee et al., "Coreceptor/Chemokine Receptor Expression on Human Hematopoietic Cells: Biological Implications for Human Immunodeficiency Virus—Type 1 Infection," Blood, vol. 93, No. 4, 1999 (pp. 1145-1156).
Liu et al., "Homozygous defect in HIV-1 coreceptor accounts for resistance of some multiply-exposed individuals to HIV-1 infection," Cell, vol. 86, No. 3, 1996 (pp. 367-377).
Lord, B. I. et al "Mobilization of Early Hematopoietic Progenitor Cells with BB-1001-: A Genetically Engineered Variant of Human Macrophage Inflammatory Protein-1 alpha," Blood, vol. 85, No. 12, 1995 (pp. 3412-3415).
Ludwig Institute for Cancer Research, "A Phase 1/2 Study of Motolimod (VTX-2337) and MEDI4736 in Subjects With Recurrent, Platinum-Resistant Ovarian Cancer for Whom Pegylated Liposomal Doxorubicin (PLD) is Indicated," ClinicalTrials.gov: NCT02431559, First Posted: May 1, 2015, Last Update: Aug. 7, 2018, https://clinicaltrials.gov/ct2/show/study/NCT02431559. Date Accessed, Mar. 25, 2019 (9 pages).
Ludwig Institute for Cancer Research, "A Phase 1/2 Study to Investigate the Safety, Biologic and Anti-tumor Activity of ONCOS-102 in Combination With Durvalumab in Subjects With Advanced Peritoneal Malignancies," ClinicalTrials.gov: NCT02963831, First Posted: Nov. 15, 2016, Last Update: Mar. 18, 2019, https://clinicaltrials.gov/ct2/show/study/NCT02963831. Date Accessed, Mar. 25, 2019 (8 pages).
Lukacs et al., "AMD3100, a CxCR4 Antagonist, Attenuates Allergic Lung Inflammation and Airway Hyperreactivity," American Journal of Pathology, vol. 16, No. 4, 2002 (pp. 1353-1360).
Lycera Corp., "Study of LYC-55716 in Adult Subjects With Locally Advanced or Metastatic Cancer," ClinicalTrials.gov: NCT02929862, First Posted: Oct. 11, 2016, Last Update: May 7, 2018, https://clinicaltrials.gov/ct2/show/study/NCT02929862. Date Accessed, Mar. 25, 2019 (6 pages).
M.D. Anderson Cancer Center, "Lirilumab and Azacitidine in Treating Patients With Refractory or Relapsed Acute Myeloid Leukemia," ClinicalTrials.gov: NCT02399917, First Posted: Mar. 26, 2015, Last Update: Nov. 30, 2018, https://clinicaltrials.gov/ct2/show/study/NCT02399917. Date Accessed, Mar. 18, 2019 (8 pages).
M.D. Anderson Cancer Center, "Lirilumab and Nivolumab With 5-Azacitidine in Patients With Myelodysplastic Syndromes (MDS)," ClinicalTrials.gov: NCT02599649, First Posted: Nov. 6, 2015, Last Update: Feb. 1, 2019, https://clinicaltrials.gov/ct2/show/study/NCT02599649. Date Accessed, Mar. 18, 2019 (8 pages).
M.D. Anderson Cancer Center, "Lirilumab With Rituximab for Relapsed, Refractory or High-risk Untreated Chronic Lymphocytic Leukemia (CLL) Patients," ClinicalTrials.gov: NCT02481297, First Posted: Jun. 25, 2015, Last Update: Jul. 3, 2018, https://clinicaltrials.gov/ct2/show/study/NCT02481297. Date Accessed, Mar. 18, 2019 (7 pages).
M.D. Anderson Cancer Center, "Nivolumab and HPV-16 Vaccination in Patients With HPV-16 Positive Incurable Solid Tumors," ClinicalTrials.gov: NCT02426892, First Posted: Apr. 27, 2015, Last Update: Aug. 6, 2018, https://clinicaltrials.gov/ct2/show/NCT02426892. Date Accessed Nov. 29, 2018 (8 pages).
Ma et al., "The chemokine receptor CXCR4 is required for retention of B lineage and granulocytic precursors in the bone marrow microenvironment," Immunity, vol. 10, Apr. 1999 (pp. 463-471).
Maciejweski-Duval et al., "Altered chemotactic response to CXCL12 in patients carrying GATA2 mutations," Journal of Leukocyte Biology, vol. 99, No. 6. Epub Dec. 28, 2015 (pp. 1065-1076).
Maekawa et al., "Chemokine/Receptor Dynamics in the Regulation of Hematopoiesis," Internal Medicine, vol. 39, No. 2., 2000 (pp. 90-100).
Matthys et al., "AMD3100, a potent and specific antagonist of the stromal cell-derived factor-1 chemokine receptor CXCR4, inhibits autoimmune joint inflammation in IFN-gamma receptor-deficient mice," Journal of Immunology, vol. 167, No. 8, 2001 (p. 4686-4692).
Maximilian Diehn, "SABR-ATAC: A Trial of TGF-beta Inhibition and Stereotactic Ablative Radiotherapy for Early Stage Non-small Cell Lung Cancer," ClinicalTrials.gov: NCT02581787, First Posted: Oct. 21, 2015, Last Update: Feb. 5, 2019, https://clinicaltrials.gov/ct2/show/study/NCT02581787. Date Accessed, Mar. 25, 2019 (7 pages).
McCormick et al., "Impaired recruitment of Grk6 and beta-Arrestin 2 causes delayed internalization and desensitization of a WHIM syndrome-associated CXCR4 mutant receptor," PLoS One, vol. 4, 2009, (e8102).
McDermott et al., "A phase 1 clinical trial of long-term, low-dose treatment of WHIM syndrome with the CXCR4 antagonist plerixafor," Blood, vol. 123, No. 15, Apr. 10, 2014 (pp. 2308-2316).
McDermott et al., "The CXCR4 antagonist plerixafor corrects panleukopenia in patients with WHIM syndrome," Blood, vol. 118, No. 18, Sep. 2, 2011 (pp. 4957-4962).
McDermott et al.,"Severe congenital neutropenia resulting from G6PC3 deficiency with increased neutrophil CXCR4 expression and myelokathexis," Blood Journal, vol. 116, 2010 (pp. 2793-2802).
McDermott, D. "Whim Syndrome," National Organization for Rare Disorders, 2013, 2016, https://rarediseases.org/rare-diseases/whim-syndrome. Date Accessed Sep. 27, 2018 (10 pages).
MedImmune LLC, "A Phase 1 Study of MEDI0562 in Adult Subjects With Selected Advanced Solid Tumors," ClinicalTrials.gov: NCT02318394, First Posted: Dec. 17, 2014, Last Update: Jan. 29, 2018, https://clinicaltrials.gov/ct2/show/study/NCT02318394. Date Accessed, Mar. 18, 2019 (7 pages).
MedImmune LLC, "A Study in Adult Subjects With Select Advanced Solid Tumors," ClinicalTrials.gov: NCT02583165, First Posted: Oct. 22, 2015, Last Update: Jan. 8, 2019, https://clinicaltrials.gov/ct2/show/study/NCT02583165. Date Accessed, Mar. 18, 2019 (7 pages).
MedImmune LLC, "A Study to Evaluate MEDI0562 in Combination With Immune Therapeutic Agents in Adult Subjects With Advanced Solid Tumors," ClinicalTrials.gov: NCT02705482, First Posted: Mar. 10, 2016, Last Update: Feb. 19, 2019, https://clinicaltrials.gov/ct2/show/study/NCT02705482. Date Accessed, Mar. 18, 2019 (10 pages).
MedImmune LLC, "MEDI9447 Alone and in Combination With MEDI4736 in Adult Subjects With Select Advanced Solid Tumors," ClinicalTrials.gov: NCT02503774, First Posted: Jul. 21, 2015, Last Update: Mar. 11, 2019, https://clinicaltrials.gov/ct2/show/study/NCT02503774. Date Accessed, Mar. 18, 2019 (8 pages).
Merck KGaA, Darmstadt, Germany, "MSB0011359C (M7824) in Subjects With Metastatic or Locally Advanced Solid Tumors," ClinicalTrials.gov: NCT02699515, First Posted: Mar. 4, 2016, Last Update: Sep. 12, 2018, https://clinicaltrials.gov/ct2/show/study/NCT02699515. Date Accessed, Mar. 25, 2019 (8 pages).
Merck Sharp & Dohme Corp., "Study of MK-1454 Alone or in Combination With Pembrolizumab in Participants With Advanced/Metastatic Solid Tumors or Lymphomas (MK-1454-001)," ClinicalTrials.gov: NCT03010176, First Posted: Jan. 4, 2017, Last Update: Mar. 15, 2019, https://clinicaltrials.gov/ct2/show/study/NCT03010176. Date Accessed, Mar. 18, 2019 (11 pages).

(56) References Cited

OTHER PUBLICATIONS

Merck Sharp & Dohme Corp., "Study of MK-4166 and MK-4166 in Combination With Pembrolizumab (MK-3475) in Participants With Advanced Solid Tumors (MK-4166-001)," ClinicalTrials.gov: NCT02132754, First Posted: May 7, 2014, Last Update: Sep. 24, 2018, https://clinicaltrials.gov/ct2/show/study/NCT02132754. Date Accessed, Mar. 18, 2019 (6 pages).
Michael et al., "Exclusive and Persistent Use of the Entry Coreceptor CXCR4 by Human Immunodeficiency Virus Type 1 from a Subject Homozygous for CCR5 Δ32," Journal of Virology, vol. 72, No. 7, Jul. 1998 (pp. 6040-6047).
Miller, J. et al, "Novel N-substituted benzimidazole CXCR4 antagonists as potential anti-HIV agents," Bioorganic & Medicinal Chemistry Letters, vol. 20, 2010 (pp. 2125-2128).
Miller, J. et al, "Synthesis and SAR of novel isoquinoline CXCR4 antagonists with potent anti-HIV activity," vol. 20, 2010 (pp. 3026-3030).
Montane et al., "Prevention of murine autoimmune diabetes by CCL22-mediated Treg recruitment to pancreatic islets," Journal of Clinical Investigation, vol. 121, No. 8, Aug. 2011 (pp. 3024-3028).
Mosi R. M. et al., "The molecular pharmacology of AMD11070: An orally bioavailable CXCR4 HIV entry inhibitor," Biochemical Pharmacology, vol. 83, 2012 (pp. 472-479).
Moskovits N. et al., "p53 attenuates cancer cell migration and invasion through repression of SDF-1/CXCL12 expression in stromal fibroblasts," Cancer Research, vol. 66, No. 22, Nov. 15, 2006 (pp. 10671-10676).
Motzer et al. (2015), "Nivolumab versus Everolimus in Advanced Renal-Cell Carcinoma," New England Journal of Medicine, vol. 373, No. 19, (pp. 1803-1813).
Moyle, et al., "Proof of Activity with AMD11070, an Orally Bioavailable Inhibitor of CXCR4-Tropic HIV Type 1," Clinical Infectious Diseases, vol. 48, 2009 (pp. 798-805).
Murdoch et al., "Chemokine receptors and their role in inflammation and infectious diseases," Blood, vol. 95, 2000 (pp. 3032-3043).
Nagaraj S. et al., "Altered recognition of antigen is a mechanism of CD8+ T cell tolerance in cancer," Natural Medicine, vol. 13, No. 7, Jul. 2007 (pp. 828-835).
Nagase et al., "Expression of CXCR4 in Eosinophils: Functional Analyses and Cytokine-Mediated Regulation," The Journal of Immunology, vol. 164, No. 11, 2000 (pp. 5935-5943).
Nanki et al., "Cutting Edge: Stromal Cell-Derived Factor-1 is a Costimulator for CD4+ T Cell Activation," The Journal of Immunology, vol. 164, No. 10, 2000 (pp. 5010-5014).
Nash et al., "Allogeneic HSCT for autoimmune diseases: conventional conditioning regimens," Bone Marrow Transplantation, vol. 32, 2003 (pp. S77-S80).
National Cancer Institute (NCI), "A Phase I Study of Intravenous Recombinant Human IL-15 in Adults With Refractory Metastatic Malignant Melanoma and Metastatic Renal Cell Cancer," ClinicalTrials.gov: NCT01021059, First Posted: Nov. 26, 2009, Last Update: Feb. 26, 2019, https://clinicaltrials.gov/ct2/show/study/NCT01021059. Date Accessed, Mar. 20, 2019 (9 pages).
National Cancer Institute (NCI), "Anti-ICOS Monoclonal Antibody MEDI-570 in Treating Patients With Relapsed or Refractory Peripheral T-cell Lymphoma Follicular Variant or Angioimmunoblastic T-cell Lymphoma," ClinicalTrials.gov: NCT02520791, First Posted: Aug. 13, 2015, Last Update: Feb. 6, 2019, https://clinicaltrials.gov/ct2/show/study/NCT02520791. Date Accessed, Mar. 18, 2019 (13 pages).
National Cancer Institute (NCI), "Part 2 of Phase 1 Study of GC1008 to Treat Advanced Melanoma (Part 2 Will Only Accept and Treat Patients With Advanced Malignant Melanoma)," ClinicalTrials.gov: NCT00923169, First Posted: Jun. 18, 2009, Last Update: Mar. 12, 2019, https://clinicaltrials.gov/ct2/show/study/NCT00923169. Date Accessed, Mar. 25, 2019 (8 pages).
National Cancer Institute (NCI), "Subcutaneous Recombinant Human IL-15 (s.c. rhIL-15) and Alemtuzumab for People With Refractory or Relapsed Chronic and Acute Adult T-cell Leukemia (ATL)," ClinicalTrials.gov: NCT02689453, First Posted: Feb. 24, 2016, Last Update: Mar. 20, 2019, https://clinicaltrials.gov/ct2/show/study/NCT02689453. Date Accessed, Mar. 20, 2019 (9 pages).
National Cancer Institute (NCI), "Trametinib and Navitoclax in Treating Patients With Advanced or Metastatic Solid Tumors," ClinicalTrials.gov: NCT02079740, First Posted: Mar. 6, 2014, Last Update: Feb. 6, 2019, https://clinicaltrials.gov/ct2/show/study/NCT02079740. Date Accessed, Mar. 25, 2019 (12 pages).
National Cancer Institute (NCI), "Use of IL-15 After Chemotherapy and Lymphocyte Transfer in Metastatic Melanoma," ClinicalTrials.gov: NCT01369888, First Posted: Jun. 9, 2011, Last Update: Jan. 27, 2015, https://clinicaltrials.gov/ct2/show/study/NCT01369888. Date Accessed, Mar. 20, 2019 (9 pages).
National Cancer Institute, "Nivolumab and Ipilimumab in Treating Patients With HIV Associated Relapsed or Refractory Classical Hodgkin Lymphoma or Solid Tumors That Are Metastatic or Cannot Be Removed by Surgery," ClinicalTrials.gov: NCT02408861, First Posted: Apr. 6, 2016, Last Update: Jun. 12, 2018, https://clinicaltrials.gov/ct2/show/study/NCT02408861. Date Accessed, Nov. 29, 2018 (13 pages).
National Cancer Institute, "Nivolumab in Treating Patients With HTLV-Associated T-Cell Leukemia/Lymphoma," ClinicalTrials.gov: NCT02631746, First Posted: Dec. 16, 2015, Last Update: Aug. 28, 2018, https://clinicaltrials.gov/ct2/show/study/NCT02631746. Date Accessed, Nov. 29, 2018 (9 pages).
Neumedicines Inc., "NM-IL-12 (rHuIL-12) in Relapsed/Refractory Diffuse Large B-Cell Lymphoma (DLBCL) Undergoing Salvage Chemotherapy," ClinicalTrials.gov: NCT02544724, First Posted: Sep. 9, 2015, Last Update: Aug. 3, 2016, https://clinicaltrials.gov/ct2/show/study/NCT02544724. Date Accessed, Mar. 20, 2019 (8 pages).
Neumedicines Inc., "NM-IL-12 in Cutaneous T-Cell Lymphoma (CTCL) Undergoing Total Skin Electron Beam Therapy (TSEBT)," ClinicalTrials.gov: NCT02542124, First Posted: Sep. 4, 2015, Last Update: Nov. 16, 2018, https://clinicaltrials.gov/ct2/show/study/NCT02542124. Date Accessed, Mar. 20, 2019 (8 pages).
Nicholas Butowski, "A Study of Varlilumab and IMA950 Vaccine Plus Poly-ICLC in Patients With WHO Grade II Low-Grade Glioma (LGG)," ClinicalTrials.gov: NCT02924038, First Posted: Oct. 5, 2016, Last Update: Mar. 6, 2019, https://clinicaltrials.gov/ct2/show/study/NCT02924038. Date Accessed, Mar. 18, 2019 (9 pages).
No author listed, SciFinder Search Results, No month listed, 2015 (39 pages).
No author listed, SciFinder Search Results, No month listed, 2015 (9 pages).
Novartis Pharmaceuticals, "A Phase I/Ib Study of NIZ985 in Combination With PDR001 in Adults With Metastatic Cancers," ClinicalTrials.gov: NCT02452268, First Posted: May 22, 2015, Last Update: Oct. 2, 2018, https://clinicaltrials.gov/ct2/show/study/NCT02452268. Date Accessed, Mar. 20, 2019 (7 pages).
Novartis Pharmaceuticals, "Phase I/Ib Study of GWN323 Alone and in Combination With PDR001 in Patients With Advanced Malignancies and Lymphomas," ClinicalTrials.gov: NCT02740270, First Posted: Apr. 15, 2016, Last Update: Feb. 18, 2019, https://clinicaltrials.gov/ct2/show/study/NCT02740270. Date Accessed, Mar. 28, 2019 (6 pages).
Novartis Pharmaceuticals, "Phase I/Ib Study of NIS793 in Combination With PDR001 in Patients With Advanced Malignancies.," ClinicalTrials.gov: NCT02947165, First Posted: Oct. 27, 2016, Last Update: Nov. 6, 2018, https://clinicaltrials.gov/ct2/show/study/NCT02947165. Date Accessed, Mar. 25, 2019 (9 pages).
Novartis Pharmaceuticals, "Phase I/II Study of BLZ945 Single Agent or BLZ945 in Combination With PDR001 in Advanced Solid Tumors," ClinicalTrials.gov: NCT02829723, First Posted: Jul. 12, 2016, Last Update: Jul. 12, 2018, https://clinicaltrials.gov/ct2/show/study/NCT02829723. Date Accessed, Mar. 18, 2019 (7 pages).
Novartis Pharmaceuticals, "Safety and Efficacy of MBG453 as Single Agent and in Combination With PDR001 in Patients With Advanced Malignancies," ClinicalTrials.gov: NCT02608268, First Posted: Nov. 18, 2015, Last Update: Oct. 2, 2018, https://clinicaltrials.gov/ct2/show/study/NCT02608268. Date Accessed, Mar. 25, 2019 (10 pages).
Novartis Pharmaceuticals, "Study of the Safety and Efficacy of MIW815 With PDR001 to Patients With Advanced/Metastatic Solid

(56) References Cited

OTHER PUBLICATIONS

Tumors or Lymphomas," ClinicalTrials.gov: NCT03172936, First Posted: Jun. 1, 2017, Last Update: Feb. 18, 2019, https://clinicaltrials.gov/ct2/show/study/NCT03172936. Date Accessed, Mar. 18, 2019 (9 pages).
Nyunt, et al., "Pharmacokinetic Effect of AMD070, an Oral CXCR4 Antagonist, on CYP3A4 and CYP2D6 Substrates Midazolam and Dextromethorphan in Healthy Volunteers," Journal of Acquired Immune Deficiency Syndrome, vol. 47, 2008 (pp. 559-565).
O'Hagen et al., "Apoptosis Induced by Infection of Primary Brian Cultures with Diverse Human Immunodeficiency Virus Type 1 Isolates: Evidence for a Role of the Envelope," Journal of Virology, vol. 73, No. 2, Feb. 1999 (pp. 897-906).
Okazaki, T. et al., "A rheostat for immune responses: the unique properties of PD1 and their advantages for clinical application," Nature Immunology, vol. 14, No. 12, Dec. 2013 (pp. 1212-1218).
Oncolytics Biotech, "A Study of REOLYSIN® in Combination With Gemcitabine in Patients With Advanced Pancreatic Adenocarcinoma," ClinicalTrials.gov: NCT00998322, First Posted: Oct. 20, 2009, Last Update: Apr. 10, 2015, https://clinicaltrials.gov/ct2/show/study/NCT00998322. Date Accessed, Mar. 25, 2019 (6 pages).
Oncolytics Biotech, "Efficacy Study of REOLYSIN® in Combination With Paclitaxel and Carboplatin in Platinum-Refractory Head and Neck Cancers," ClinicalTrials.gov: NCT01166542, First Posted: Jul. 21, 2010, Last Update: Nov. 5, 2014, https://clinicaltrials.gov/ct2/show/study/NCT01166542. Date Accessed, Mar. 25, 2019 (7 pages).
Oncolytics Biotech, "Phase 2 Study of REOLYSIN® in Combination With Paclitaxel and Carboplatin for Non-Small Cell Lung Cancer With KRAS or EGFR Activation," ClinicalTrials.gov: NCT00861627, First Posted: Mar. 13, 2009, Last Update: Dec. 2, 2015, https://clinicaltrials.gov/ct2/show/study/NCT00861627. Date Accessed, Mar. 25, 2019 (7 pages).
OncoMed Pharmaceuticals, Inc., "A Study of OMP-313M32 in Subjects With Locally Advanced or Metastatic Solid Tumors," ClinicalTrials.gov: NCT03119428, First Posted: Apr. 18, 2017, Last Update: Dec. 7, 2018, https://clinicaltrials.gov/ct2/show/study/NCT03119428. Date Accessed, Mar. 25, 2019 (7 pages).
Panka, DJ. et al., "HDM2 antagonism delays the development of sunitinib resistance in RCC xenografts: Effects of MI-319 on sunitinib-induced p53 activation, SDF-1 induction, and tumor infiltration by CD11b+/Gr-1+ myeloid suppressor cells," Molecular Cancer, vol. 12, No. 17, 2013 (pp. 1-12).
Peled et al., "The chemokine SDF-1 activates the integrins LFA-1, VLA-4, and VLA-5 on immature human CD34(+) cells: role in transendothelial/stromal migration and engraftment of NOD/SCID mice," Blood, vol. 95, No. 11, 2000 (pp. 3289-3296).
Pfizer, "A Study of Avelumab in Combination With Other Cancer Immunotherapies in Advanced Malignancies (JAVELIN Medley)," ClinicalTrials.gov: NCT02554812, First Posted: Sep. 18, 2015, Last Update: Mar. 13, 2019, https://clinicaltrials.gov/ct2/show/study/NCT02554812. Date Accessed, Mar. 18, 2019 (13 pages).
Pfizer, "Avelumab in Combination Regimens That Include an Immune Agonist, Epigenetic Modulator, CD20 Antagonist and/or Conventional Chemotherapy in Patients With Relapsed or Refractory Diffuse Large B-cell Lymphoma (R/R DLBCL) (Javelin DLBCL)," ClinicalTrials.gov: NCT02951156, First Posted: Nov. 1, 2016, Last Update: Jan. 29, 2019, https://clinicaltrials.gov/ct2/show/study/NCT02951156. Date Accessed, Mar. 18, 2019 (11 pages).
Pike et al., "Nutrition: An Integrated Approach," Third Edition, John Wiley & Sons, 1984 (pp. 538-539).
Plexxikon, "A Combination Clinical Study of PLX3397 and Pembrolizumab to Treat Advanced Melanoma and Other Solid Tumors," ClinicalTrials.gov: NCT02452424, First Posted: May 22, 2015, Last Update: Nov. 15, 2018, https://clinicaltrials.gov/ct2/show/study/NCT02452424. Date Accessed, Mar. 18, 2019 (9 pages).
Ponath et al., "Chemokine receptor antagonists: novel therapeutics for inflammation and AIDS" Expert Opinion on Investigational Drugs, vol. 7, No. 1, 1998 (pp. 1-18).

Providence Health & Services, "Anti-OX40 Antibody (MEDI6469) in Patients With Metastatic Colorectal Cancer," ClinicalTrials.gov: NCT02559024, First Posted: Sep. 24, 2015, Last Update: Oct. 10, 2018, https://clinicaltrials.gov/ct2/show/study/NCT02559024. Date Accessed, Mar. 18, 2019 (6 pages).
Providence Health & Services, "Anti-OX40 Antibody in Head and Neck Cancer Patients," ClinicalTrials.gov: NCT02274155, First Posted: Oct. 24, 2014, Last Update: Nov. 26, 2018, https://clinicaltrials.gov/ct2/show/study/NCT02274155. Date Accessed, Mar. 18, 2019 (6 pages).
Providence Health & Services, "Anti-OX40, Cyclophosphamide (CTX) and Radiation in Patients With Progressive Metastatic Prostate Cancer," ClinicalTrials.gov: NCT01303705, First Posted: Feb. 25, 2011, Last Update: Aug. 29, 2018, https://clinicaltrials.gov/ct2/show/study/NCT01303705. Date Accessed, Mar. 18, 2019 (10 pages).
Providence Health & Services, "Stereotactic Body Radiation and Monoclonal Antibody to OX40 (MEDI6469) in Breast Cancer Patients With Metastatic Lesions (OX40 Breast)," ClinicalTrials.gov: NCT01862900, First Posted: May 27, 2013, Last Update: Mar. 6, 2019, https://clinicaltrials.gov/ct2/show/study/NCT01862900. Date Accessed, Mar. 18, 2019 (7 pages).
PsiOxus Therapeutics Ltd, "Phase I / Dose Expansion Study of Enadenotucirev in Ovarian Cancer Patients (OCTAVE)," ClinicalTrials.gov: NCT02028117, First Posted: Jan. 6, 2014, Last Update: Feb. 26, 2019, https://clinicaltrials.gov/ct2/show/study/NCT02028117. Date Accessed, Mar. 25, 2019 (8 pages).
PsiOxus Therapeutics Ltd, "Phase I Study of Enadenotucirev and PD-1 Inhibitor in Subjects With Metastatic or Advanced Epithelial Tumors (SPICE)," ClinicalTrials.gov: PsiOxus Therapeutics Ltd, First Posted: Dec. 21, 2015, Last Update: Mar. 4, 2019, https://clinicaltrials.gov/ct2/show/study/NCT02636036. Date Accessed, Mar. 25, 2019 (9 pages).
PubChem Open Chemistry Database, Compound Summary for CID 10890081, created Oct. 25, 2006 (14 pages).
PubChem Open Chemistry Database, Compound Summary for CID 12087079, created Feb. 7, 2007 (14 pages).
PubChem Open Chemistry Database, Compound Summary for CID 19046926, created Dec. 4, 2017 (11 pages).
PubChem Open Chemistry Database, Compound Summary for CID 70962830, created Mar. 21, 2013 (12 pages).
Rana et al., "Role of CCR5 in infection of primary macrophages and lymphocytes by macrophage-tropic strains of human immunodeficiency virus: resistance to patient-derived and prototype isolates resulting from the delta ccr5 mutation," Journal of Virology, vol. 71, No. 4, 1997 (pp. 3219-3227).
Ratajczak, et al., "The pleotropic effects of the SDF-1-CXCR4 axis in organogenesis, regeneration, and tumorigenesis," Leukemia, vol. 20, 2006 (pp. 1915-1924).
Reetz et al., "Highly Efficient Lipase-Catalyzed Kinetic Resolution of Chiral Amines" Chimia International Journal for Chemistry, vol. 48, No. 12, 1994 (p. 570).
Regeneron Pharmaceuticals, "An Exploratory Tumor Biopsy-driven Study to Understand the Relationship Between Biomarkers and Clinical Response in Melanoma Patients Receiving REGN2810 (Anti-PD-1)," ClinicalTrials.gov: NCT03002376, First Posted: Dec. 23, 2016, Last Update: Jan. 11, 2019, https://clinicaltrials.gov/ct2/show/study/NCT03002376. Date Accessed, Mar. 25, 2019 (6 pages).
Regeneron Pharmaceuticals, "PD-1 in Patients With Advanced Basal Cell Carcinoma Who Experienced Progression of Disease on Hedgehog Pathway Inhibitor Therapy, or Were Intolerant of Prior Hedgehog Pathway Inhibitor Therapy," ClinicalTrials.gov: NCT03132636, First Posted: Apr. 28, 2017, Last Update: Oct. 2, 2018, https://clinicaltrials.gov/ct2/show/study/NCT03132636. Date Accessed, Mar. 25, 2019 (6 pages).
Regeneron Pharmaceuticals, "Study of REGN 2810 Compared to Platinum-Based Chemotherapies in Participants With Metastatic Non-Small Cell Lung Cancer (NSCLC)," ClinicalTrials.gov: NCT03088540, First Posted: Mar. 23, 2017, Last Update: Nov. 5, 2018, https://clinicaltrials.gov/ct2/show/study/NCT03088540. Date Accessed, Mar. 25, 2019 (9 pages).
Regeneron Pharmaceuticals, "Study of REGN2810 and REGN1979 in Patients With Lymphoma," ClinicalTrials.gov: NCT02651662,

(56) References Cited

OTHER PUBLICATIONS

First Posted: Jan. 11, 2016, Last Update: Sep. 11, 2018, https://clinicaltrials.gov/ct2/show/study/NCT02651662. Date Accessed, Mar. 25, 2019 (7 pages).
Regeneron Pharmaceuticals, "Study of REGN2810 in Patients With Advanced Cutaneous Squamous Cell Carcinoma," ClinicalTrials.gov: NCT02760498, First Posted: May 3, 2016, Last Update: Jan. 14, 2019, https://clinicaltrials.gov/ct2/show/study/NCT02760498. Date Accessed, Mar. 25, 2019 (6 pages).
Regeneron Pharmaceuticals, "Study of REGN3767 (Anti-LAG-3) With or Without REGN2810 (Anti-PD1) in Advanced Cancers," ClinicalTrials.gov: NCT03005782, First Posted: Dec. 29, 2016, Last Update: Jun. 18, 2018, https://clinicaltrials.gov/ct2/show/study/NCT03005782. Date Accessed, Mar. 25, 2019 (7 pages).
Righi E. et al., "CXCL12/CXCR4 Blockade Induces Multimodal Antitumor Effects That Prolong Survival in an Immunocompetent Mouse Model of Ovarian Cancer," Cancer Research, vol. 71, No. 16, Aug. 15, 2011 (pp. 5522-5534).
Robert Lowsky, "A Phase I/II Study of Intratumoral Injection of SD-101," ClinicalTrials.gov: NCT02254772, First Posted: Oct. 2, 2014, Last Update: Sep. 29, 2017, https://clinicaltrials.gov/ct2/show/study/NCT02254772. Date Accessed, Mar. 25, 2019 (9 pages).
Robert, et al., "Pembrolizumab versus Ipilimumab in Advanced Melanoma," New England Journal of Medicine, vol. 372, 2015 (pp. 2521-2532).
Salcedo et al., "Vascular endothelial growth factor and basic fibroblast growth factor induce expression of CXCR4 on human endothelial cells: In vivo neovascularization induced by stromal-derived factor-1alpha.Am," The American Journal of Pathology, vol. 154, No. 4, 1999 (pp. 1125-1135).
Saxena et al., "Efficacy and Mechanism of Action of CXCR4 Inhibition in B16 OVA Melanoma Model," The Society for Immunotherapy of Cancer Annual Meeting, National Harbor, Maryland, Nov. 8-12, 2017 (1 page).
Saxena et al., "Efficacy and Mechanism of Action of CXCR4 Inhibition in B16-OVA Melanoma Model," Journal for ImmunoTherapy of Cancer, Abstract, vol. 5, Suppl. 2, 2017 (p. 356).
Scala, et al., "Expression of CXCR4 predicts poor prognosis in patients with malignant melanoma," Clinical Cancer Research, vol. 11, Mar. 1, 2005 (pp. 1835-1841).
Schlabach et al., "Cancer proliferation gene discovery through functional genomics," Science, vol. 319, No. 5863, Feb. 1 2008 (pp. 620-624).
Schols et al., "Bicyclams, a class of potent anti-HIV agents, are targeted at the HIV coreceptor for Fusin/CXCR-4," Antiviral Research, vol. 35, 1997 (pp. 147-156).
Schols et al., "Inhibition of T-tropic HIV Strains by Selective Antagonization of the Chemokine Receptor CXCR4J," Journal of Experimental Medicine, vol. 186, No. 8, 1997 (pp. 1383-1388).
Schramm et al., "Cytopathicity of Human Immunodeficiency Virus Type 2 (HIV-2) in Human Lymphoid Tissue is Coreceptor Dependent and Comparable to That of HIV-1," Journal of Virology, vol. 74., No. 20, 2000 (pp. 184-192).
Schuitemaker et al., "Biological phenotype of human immunodeficiency virus type 1 clones at different stages of infection: progression of disease is associated with a shift from monocytotropic to T-cell-tropic virus population," Journal of Virology, vol. 66, No. 3, 1992 (pp. 1354-1360).
Sharma, P. et al., "Primary, Adaptive, and Acquired Resistance to Cancer Immunotherapy," Cell, vol. 168, No. 4, Feb. 9, 2017 (pp. 707-723).
Shen et al., "CXCR4-mediated STAT3 activation is essential for CXCL12-induced invasion in bladder cancer," Tumour Biology, vol. 34, 2013 (pp. 1839-1845).
Shojaei F. et al., "Tumor refractoriness to anti-VEGF treatment is mediated by CD11b+Gr1+ myeloid cells," Nature Biotechnology, vol. 25, No. 8, Aug. 2007 (pp. 911-920).
Sidney Kimmel Comprehensive Cancer Center at Johns Hopkins, "Anti-LAG-3 Alone & in Combination w/ Nivolumab Treating Patients w/ Recurrent GBM (Anti-CD137 Arm Closed Oct. 16, 2018)," ClinicalTrials.gov: NCT02658981, First Posted: Jan. 20, 2016, Last Update: Feb. 11, 2019, https://clinicaltrials.gov/ct2/show/study/NCT02658981. Date Accessed, Mar. 18, 2019 (13 pages).
Sidney Kimmel Comprehensive Cancer Center at Johns Hopkins, "Pilot Study With CY, Pembrolizumab, GVAX, and IMC-CS4 (LY3022855) in Patients With Borderline Resectable Adenocarcinoma of the Pancreas," ClinicalTrials.gov: NCT03153410, First Posted: May 15, 2017, Last Update: Mar. 19, 2019, https://clinicaltrials.gov/ct2/show/study/NCT03153410. Date Accessed, Mar. 18, 2019 (8 pages).
SillaJen, Inc., "Hepatocellular Carcinoma Study Comparing Vaccinia Virus Based Immunotherapy Plus Sorafenib vs Sorafenib Alone (PHOCUS)," ClinicalTrials.gov: NCT02562755, First Posted: Sep. 29, 2015, Last Update: Feb. 6, 2019, https://clinicaltrials.gov/ct2/show/study/NCT02562755. Date Accessed, Mar. 25, 2019 (7 pages).
Silva et al., "Profiling essential genes in human mammary cells by multiplex RNA1 screening," Science, vol. 319, Feb. 1, 2008 (pp. 617-620).
Simmons et al., "CXCR4 as a Functional Coreceptor for Human Immunodeficiency Virus Type 1 Infection of Primary Macrophages," Journal of Virology, vol. 72, No. 10, 1998 (pp. 8453-8457).
Simmons et al., "Primary, syncytium-inducing human immunodeficiency virus type 1 isolates are dual-tropic and most can use either Lestr or CCR5 as coreceptors for virus entry," Journal of Virolology, vol. 70, No. 12, 1996 (pp. 8355-8360).
SK Chemicals Co., Ltd., "Study to Evaluate SID 530 Compared to Taxotere," ClinicalTrials.gov: NCT00931008, First Posted: Jul. 2, 2009, Last Update: Jan. 24, 2013, https://clinicaltrials.gov/ct2/show/study/NCT00931008. Date Accessed, Mar. 25, 2019 (6 pages).
Stone, et al., "Multiple-Dose Escalation Study of the Safety, Pharmacokinetics, and Biologic Activity of Oral AMD070, a Selective CXCR4 Receptor Inhibitor, in Human Subjects.," Antimicrobial Agents and Chemotherapy, vol. 51, No. 7, Jul. 2007 (pp. 2351-2358).
Supplementary European Search Report issued by the European Patent Office for European Patent App. No. 02775823.4, dated Dec. 23, 2004 (3 pages).
Supplementary European Search Report issued by the European Patent Office for European Patent App. No. 02805977.2, dated Apr. 16, 2008 (3 pages).
Supplementary European Search Report issued by the European Patent Office for European Patent App. No. 04752905.2, dated Mar. 12, 2010 (6 pages).
Supplementary European Search Report issued by the European Patent Office for European Patent App. No. 04814091.7, dated Mar. 10, 2008 (4 pages).
Supplementary European Search Report issued by the European Patent Office for European Patent App. No. 04760161.2, dated Jun. 10, 2008 (3 pages).
Syndax Pharmaceuticals, "A Phase 2 Multi-Center Study of Entinostat (SNDX-275) in Patient With Relapsed or Refractory Hodgkin's Lymphoma," ClinicalTrials.gov: NCT00866333, First Posted: Mar. 20, 2009, Last Update: Jul. 1, 2016, https://clinicaltrials.gov/ct2/show/study/NCT00866333. Date Accessed, Mar. 20, 2019 (6 pages).
Targovax Oy, "A Pilot Study of Sequential ONCOS-102, an Engineered Oncolytic Adenovirus Expressing GMCSF, and Pembrolizumab in Patients With Advanced or Unresectable Melanoma Progressing After Programmed Cell Death Protein 1 (PD1) Blockade," ClinicalTrials.gov: NCT03003676, First Posted: Dec. 28, 2016, Last Update: Oct. 25, 2018, https://clinicaltrials.gov/ct2/show/study/NCT03003676. Date Accessed, Mar. 25, 2019 (8 pages).
Tarhini, et al., "Immune Monitoring of the Circulation and the Tumor Microenvironment in Patients with Regionally Advanced Melanoma Receiving Neoadjuvant Ipilimumab," PLoS One, vol. 9, No. 2, Feb. 2014 (p. e87705).
Teasdale et al., "Risk Assessment of Genotoxic Impurities in New Chemical Entities: Strategies to Demonstrate Control," Organic Process Research and Development, vol. 17, 2013 (p. 221-230).
Tersmette et al., "Differential Syncytium-Inducing Capacity of Human Immunodeficiency Virus Isolates: Frequent Detection of Syncytium—Inducing Isolates in Patients with Aquired Immune

(56) References Cited

OTHER PUBLICATIONS

Deficiency Syndrome (AIDS) and AIDS-Related Complex," Journal of Virology, vol. 62, No. 6. (pp. 2026-2032).
Tesaro, Inc., "A Phase 1 Study of TSR-022, an Anti-TIM-3 Monoclonal Antibody, in Patients With Advanced Solid Tumors (AMBER)," ClinicalTrials.gov: NCT02817633, First Posted: Jun. 29, 2016, Last Update: Mar. 19, 2019, https://clinicaltrials.gov/ct2/show/study/NCT02817633. Date Accessed, Mar. 25, 2019 (8 pages).
Therasse et al., "New Guidelines to Evaluate the Response to Treatment in Solid Tumors," Journal of the National Cancer Institute, vol. 92, No. 3, Feb. 2, 2000 (pp. 205-216).
Tortorici et al., "Influence of mild and moderate hepatic impairment on axitinib pharmacokinetics," Investigational New Drugs, vol. 29, 2011 (pp. 1370-1380).
Toyozawa, et al., "Chemokine receptor CXCR4 is a novel marker for the progression of cutaneous malignant melanoma," Japan Society of Histochemisty and Cytochemistry, vol. 45, No. 5, 2012 (pp. 293-299).
Trillium Therapeutics Inc., "A Trial of TTI-621 for Patients With Hematologic Malignancies and Selected Solid Tumors," ClinicalTrials.gov: NCT02663518, First Posted: Jan. 26, 2016, Last Update: Oct. 29, 2018, https://clinicaltrials.gov/ct2/show/study/NCT02663518. Date Accessed, Mar. 18, 2019 (9 pages).
Trillium Therapeutics Inc., "Trial of Intratumoral Injections of TTI-621 in Subjects With Relapsed and Refractory Solid Tumors and Mycosis Fungoides," ClinicalTrials.gov: NCT02890368, First Posted: Sep. 7, 2016, Last Update: Mar. 13, 2019, https://clinicaltrials.gov/ct2/show/study/NCT02890368. Date Accessed, Mar. 18, 2019 (9 pages).
Tu S.P. et al., "Curcumin induces the differentiation of myeloid-derived suppressor cells and inhibits their interaction with cancer cells and related tumor growth," Cancer Prevention Research, vol. 5, No. 2, Feb. 2012 (pp. 205-215).
Tumeh, et al., "PD-1 blockade induces responses by inhibiting adaptive immune resistance," Nature, vol. 515, No. 7528, Nov. 2014 (pp. 568-571).
U.S. Appl. No. 16/091,689, filed Oct. 5, 2018 (27 pages).
U.S. Appl. No. 16/215,963, filed Dec. 11, 2018 (132 pages).
U.S. Appl. No. 16/311,020, filed Dec. 18, 2018 (237 pages).
U.S. Appl. No. 16/311,055, filed Dec. 18, 2018 (186 pages).
U.S. Appl. No. 16/311,083, filed Dec. 18, 2018 (276 pages).
University of Southern California, "Axitinib With or Without Anti-OX40 Antibody PF-04518600 in Treating Patients With Metastatic Kidney Cancer," ClinicalTrials.gov: NCT03092856, First Posted: Mar. 28, 2017, Last Update: Aug. 13, 2018, https://clinicaltrials.gov/ct2/show/study/NCT03092856. Date Accessed, Mar. 18, 2019 (11 pages).
University of Texas Southwestern Medical Center, "Phase 2 Study of IDH305 in Low Grade Gliomas," ClinicalTrials.gov: NCT02987010, First Posted: Dec. 8, 2016, Last Update: Oct. 11, 2017, https://clinicaltrials.gov/ct2/show/study/NCT02987010. Date Accessed, Mar. 25, 2019 (7 pages).
Vanharanta et al., "Epigenetic expansion of VHL-HIF signal output drives multiorgan metastasis in renal cancer," Natural Medicine, vol. 19, No. 1., Jan. 2013 (pp. 50-56).
VentiRx Pharmaceuticals Inc., "A Phase Ib Study of Neoadjuvant Cetuximab Plus Motolimod and Cetuximab Plus Motolimod Nivolumab," ClinicalTrials.gov: NCT02124850, First Posted: Apr. 28, 2014, Last Update: Jul. 22, 2016, https://clinicaltrials.gov/ct2/show/study/NCT02124850. Date Accessed, Mar. 25, 2019 (6 pages).
Ward et al., "Genetic and molecular diagnosis of severe congenital neutropenia," Current Opinion in Hematology, vol. 16, No. 1, Jan. 2009 (pp. 9-13).
Wong, "Comparison of the potential multiple binding modes of bicyclam, monocylam, and noncyclam small molecule CXC chemokine receptor 4 inhibitors," Molecular Pharmacology, vol. 74, No. 6, 2008 (pp. 1485-1495).
Zea A.H. et al. "Arginase-producing myeloid suppressor cells in renal cell carcinoma patients: a mechanism of tumor evasion," Cancer Research, vol. 65, No. 8, 2005 (pp. 3044-3048).
Zhang et al. "Preferential involvement of CXCR4 and CXCL12 in T cell migration toward melanoma cells," Cancer Biology & Therapy, vol. 5, No. 10, Oct. 2006 (pp. 1034-1312).
Zhang et al., "Chemokine Coreceptor Usage by Diverse Primary Isolates of Human Immunodeficiency Virus Type 1," Journal of Virology, vol. 72, No. 11, 1998 (pp. 9307-9312).
Zhang et al., "Will Multiple Coreceptors Need to Be Targeted by Inhibitors of Human Immunodeficiency Virus Type 1 Entry?," Journal of Virology, vol. 73, No. 4., 1999 (pp. 3443-3448).
Zhao et al., "TNF signaling drives myeloid-derived suppressor cell accumulation," Journal of Clinical Investigation, vol. 122, No. 11, Nov. 2012 (pp. 4094-4104).
Zlotnik et al., "Chemokines: a new classification system and their role in immunity," Immunity, vol. 12, Feb. 2000 (pp. 121-127).
Zou et al., "PD-L1 (B7-H1) and PD-1 Pathway Blockade for Cancer Therapy: Mechanisms, Response Biomarkers and Combinations," Science Translatonal Medicine, vol. 8., No. 328, Mar. 2016 (pp. 1-34).
Zuelzer, "'Myelokathexis'—A New Form of Chronic Granulocytopenia. Report of a case," New England Journal of Medicine, vol. 270, No. 14, 1964 (pp. 699-704).
*Apotex Inc.* v. *Wyeth LLC*, Fed. Cir. 2016 Appeal No. 2015-1871.
*UCB, Inc.* v. *Watson Laboratories*, 927 F.3d 1272 (Fed. Cir. 2019).
Andtbacka et al., "X4P-001, an Orally Bioavailable CXCR4 Antagonist, Increases T Cell Infiltration in Human Metastatic Melanoma," The Society for Immunotherapy of Cancer Annual Meeting, National Harbor, Maryland, Nov. 8-12, 2017 (1 page).
AnorMed, "X4P-001 Product Page," Adis Insight, Lastest Information Update: Mar. 20, 2019, https://adisinsight.springer.com/drugs/800017499, Date Accessed, Apr. 1, 2019 (5 pages).
Azilji et al., "New Developments in the Treatment of Metastatic Melanoma: Immune Checkpoint Inhibitors and Targeted Therapies," Anticancer Research, vol. 34, 2014 (pp. 1493-1506).
Boutsikou et al., "Tumour necrosis factor, interferon-gamma and interleukins as predictive markers of antiprogrammed cell-death protein-1 treatment in advanced non-small cell lung cancer: a pragmatic approach in clinical practice," Therapeutic Advances in Medical Oncology, vol. 10, 2018 (pp. 1-8).
Bristol-Myers Squibb, "Safety and Efficacy Study of Ulocuplumab and Nivolumab in Subjects With Solid Tumors (CXCessoR4)," ClinicalTrials.gov: NCT02472977, First Posted: Jun. 16, 2015, Last Update: Nov. 1, 2018, https://clinicaltrials.gov/ct2/show/study/NCT02472977. Date Accessed, Aug. 20, 2019 (7 pages).
Courtney et al., "Optimizing recent advances in metastatic renal cell carincoma," Current Onocology Reports, vol. 11, No. 3, May 1, 2009 (pp. 218-226).
DePrimo et al., "Circulating protein biomarkers of pharmacodynamic activity of sunitinib in patients with metastatic renal cell carcinoma: modulation of VEGF and VEGF-related proteins," Journal of Translational Medicine, vol. 5, No. 32, Jul. 2, 2007 (11 pages).
Hamid et al., "Safety and Tumor Responses with Lambrolizumab (Anti-PD-1) in Melanoma," New England Journal of Medicine, vol. 369, No. 2, 2013 (pp. 134-144).
Langan et al., "Liver Directed Therapy for Renal Cell Carcinoma," Journal of Cancer, vol. 3, 2012 (pp. 184-190).
Motzer et al., "Nivolumab for Metastatic Renal Cell Carcinoma: Results of a Randomized Phase II Trial," Journal of Clinical Oncology, vol. 33, No. 13, 2015 (pp. 1430-1437).
Neves, M. et al., Ligand-guided optimization of CXCR4 homology models for virtual screening using a multiple chemotype approach, Journal of Computer-Aided Molecular Design, vol. 24, No. 12, Oct. 20, 2010 (pp. 1023-1033).
O'Boyle et al., "Inhibition of CXCR4-CXCL12 chemotaxis in melanoma by AMD11070," British Journal of Cancer, vol. 108, No. 8, Apr. 2013 (pp. 1634-1640).
Parameswaran et al., "Combination of drug therapy in acute lymphblastic leukemia with CXCR4 antagonist," Leukemia, vol. 25, No. 8, Aug. 1, 2011 (pp. 1314-1323).
PubChem Open Chemistry Database, Compound Summary for SID 219642471, created Oct. 21, 2014 (12 pages).
Raman et al., "Immunotherapy in Metastatic Renal Cell Carcinoma: A Comprehensive Review," Biomed Research International, vol. 2015, 2015 (pp. 1-9).

(56) References Cited

OTHER PUBLICATIONS

Reagen-Shaw et al., "Dose translation from animal to human studies revisited," The FASEB Journal, vol. 22, Mar. 2007 (pp. 659-661).
Rini et al., "Comparative effectiveness of axitinib versus soragenib in advanced renal cell carcinoma (AXIS): a randomness phase 3 trial," Lancet, vol. 378, 2011 (pp. 1931-1939).
Scala et al., "Molecular Pathways: Targeting the CXCR4-CXCL12 Axis—Untapped Potential in the Tumor Microenvironment," Clincal Cancer Research, vol. 21, No. 19, Jul. 21, 2015 (pp. 4278-4285).
Sullivan et al., "Pembrolizumab for Treatment of Patients with Advanced or Unresectable Melanoma," Clincal Cancer Research, vol. 12, No. 13, Apr. 30, 2015 (pp. 2892-2897).
Andtbacka et al., "X4P-001, an Orally Bioavailable CXCR4 Antagonist, Increase T Cell Infiltration in Human Metastatic Melanoma," The Society for Immunotherapy of Cancer Annual Meeting, National Harbor, Maryland, Nov. 8-12, 2017 (1 page).
Choueiri et al., "Combination Therapy with the CXCR4 Inhibitor X4P-001 and Nivolumab Demonstrates Preliminary Anti-tumor Activity in RCC Patients that are Unresponsive to Nivolumab Alone," 2018 ESMO Congress, Munich Germany, Oct. 19-23, 2018 (1 page).
Choueiri, "Systematic Therapy for Metastatic Renal-Cell Carcinoma," The New England Journal of Medicine, 2017, 376:354-66.
Dudley et al., "CD8+ Enriched "Young" Tumor Infiltrating Lymphocytes Can Mediate Regression of Metastatic Melanoma," Clinical Cancer Research, 2010, 16(24):6122-6131.
Gao et al., "Intratumoral Balance of Regulatory and Cytotoxic T Cells Is Associated With Prognosis of Hepatocellular Carcinoma After Resection," Journal of Clinical Oncology, 2007, 25(18):2586-2593.
Gassenmeier et al., "CXC Chemokine Receptor 4 is Essential for Maintenance of Renal cell Carcinoma?Initiating Cells and Predicts Metastasis," Stem Cells Journals, 2013, 31(8):1467-1476.
Hainsworth et al., "A Randomized, Open-Label Phase 2 Study of the CXCR4 Inhibitor LY2510924 in Combination with Sunitinib Versus Sunitinib Alone in Patients with Metastatic Renal Cell Carcinoma," Target Oncology, 2016, 11:643-653.
McDermott et al., "Safety and Efficacy of the Oral CXCR4 Inhibitor X4P-001 + Axitnib in Advanced Renal Cell Carcinoma Patients: An Analysis of Subgroup Responses by Prior Treatment," ESMO Congress, Barcelona, Spain, Sep. 30, 2019 (1 page).
Morimoto et al., "Enhancement of the CXCL12/CXCR4 axis due to acquisition of gemcitabine resistance in pancreatic cancer: effect of CXCR4 antagonists," BMC Cancer. 2016, 16(305):1-13.
Panka et al., "MDSC trafficking and function in RCC by CXCR4 in the presence of a VEGF-R antagonist is dependent on HIF-2? expression," European Journal of Cancer, 2016, 69(Supp 1): 146 (1 page).
PCT International Search Report and Written Opinion from PCT/US2017/026819 dated Jul. 21, 2017.
PCT International Search Report and Written Opinion from PCT/US2017/038590 dated Oct. 17, 2017.
PCT International Search Report and Written Opinion from PCT/US2017/038609 dated Oct. 31, 2017.
PCT International Search Report and Written Opinion from PCT/US2017/038613 dated Dec. 28, 2017.
PCT International Search Report and Written Opinion from PCT/US2018/038776 dated Nov. 20, 2018.
PCT International Search Report and Written Opinion from PCT/US2018/059482 dated Jan. 17, 2019.
Portella et al., Preclinical Development of a Novel Class of CXCR4 Antagonist Impairing Solid Tumors Growth and Metastases, PLOS One, 2013, 8(9):1-9.
Skerlj R. et al., "Discovery of Novel Small Molecule Orally Bioavailable C-X-C Chemokine Receptor 4 Antagonists That Are Potent Inhibitors of T-Tropic (X4) HIV-1 Replication," Journal of Medicinal Chemistry, 2010, 53(8):3376-3388.
Vaishampayan et al., "A Phase 1/2 Study Evaluating the Efficacy and Safety of the Oral CXCR4 Inhibitor X4P-001 in Combination with Axitinib in Patients with Advanced Renal Cell Carcinoma," 2018 American Society for Clinical Oncology Annual Meeting, Chicago, Illinois, Jun. 2, 2018 (1 page).

\* cited by examiner

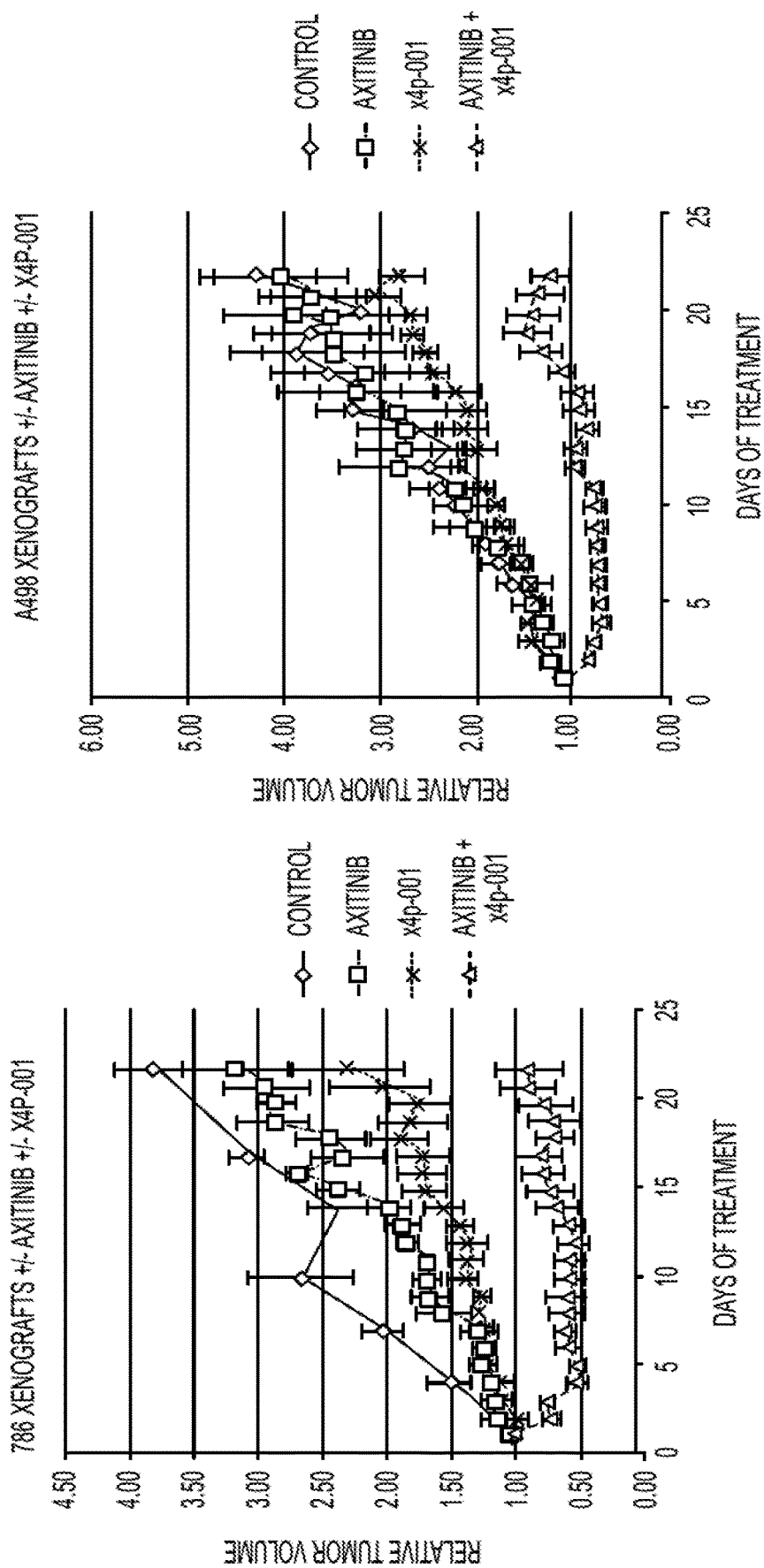

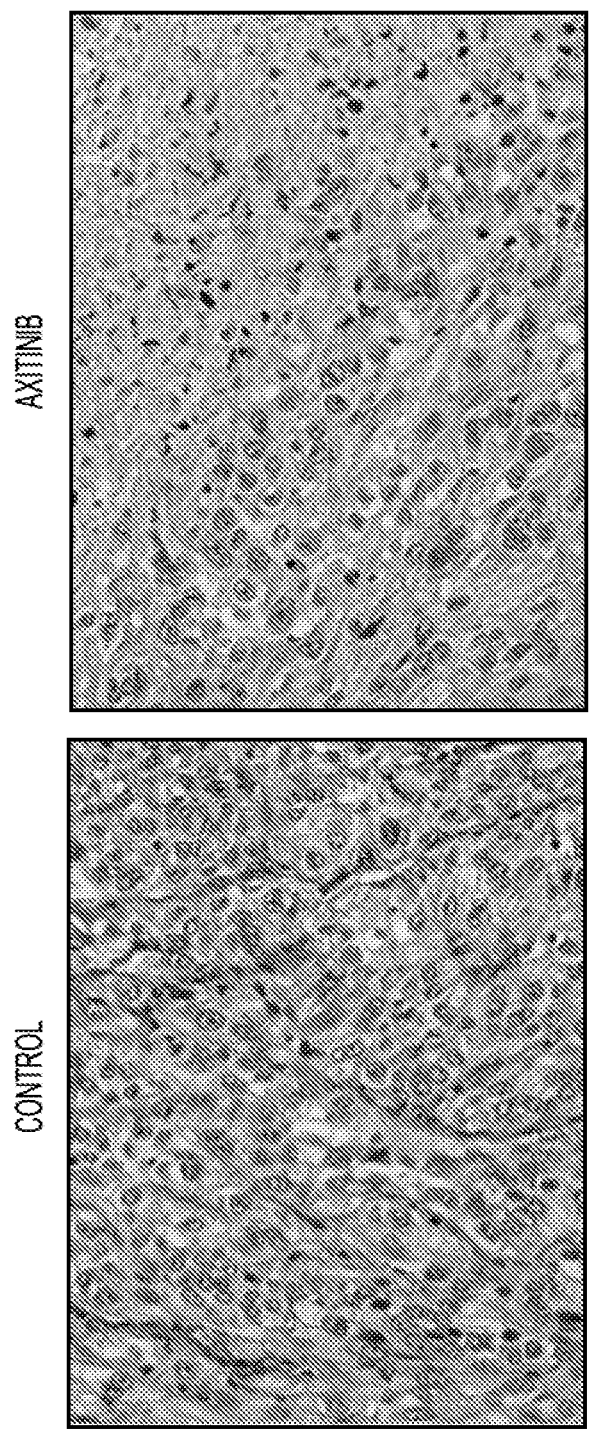

* $P<0.05$ VS. CONTROL
** $P<0.05$ X4P-001 PLUS AXITINIB VS. X4P-001 ALONE

MDSC (CD11b+ GR-1+) INFILTRATING 786 XENOGRAFTS TREATED WITH AXITINIB ALONE (LOW POWER)

METHODS FOR TREATING CANCER

CROSS-REFERENCE TO RELATED APPLICATIONS

This application claims the benefit of priority to U.S. Provisional Patent Application Ser. Nos. 62/267,052, filed Dec. 14, 2015, U.S. Ser. No. 62/271,087, filed Dec. 22, 2015, U.S. Ser. No. 62/281,962, filed Jan. 22, 2016, and U.S. Ser. No. 62/428,964, filed Dec. 1, 2016, the entirety of each of which is hereby incorporated by reference.

FIELD OF THE INVENTION

The present invention relates to methods for treating cancer, in particular, methods for overcoming resistance to treatment with VEGF-R antagonists in cancers, such as renal cell carcinoma.

BACKGROUND OF THE INVENTION

In ~75% of patients with sporadic clear-cell renal cell carcinoma (ccRCC) there is functional loss of the VHL gene, typically by mutation, but also silencing by hypermethylation. VHL encodes the von Hippel-Lindau tumor suppression protein, which mediates proteolytic degradation of the hypoxia-inducible factor (HIF)-α [2]. Loss of this function results in increased levels of HIF-α, increased expression of VEGF, tumor angiogenesis, and, ultimately, the hypervascularity characteristic of these malignancies. Multiple agents that block the activation of the VEGF pathway have been shown to improve outcomes, including tyrosine kinase inhibitors (TKIs), such as sunitinib, axitinib, sorafenib or pazopanib, that block the VEGF signaling pathway and bevacizumab, a monoclonal antibody, that binds circulating VEGF and thus prevents the ligand from binding to the VEGF receptor.

Despite the demonstrated benefits of such angiogenesis inhibitors in ccRCC, the approach is not curative. Although many patients respond initially, most of them experience relapse and progression. There is a clear unmet need for agents that improve outcomes by preventing or delaying treatment resistance.

BRIEF DESCRIPTION OF THE FIGURES

FIGS. 1A and 1B illustrates the increase in tumor regression observed in two murine models of tumor xenografts that have been treated with a combination of X4P-001 and axitinib, as described in Example 1. FIG. 1A shows the relative effects on tumor volume of treatment of murine 786-0 xenografts in mice treated with control, axitinib or X4P-001 as single agents, and with a combination of X4P-001 and axitinib. FIG. 1B shows the relative effects on tumor volume of treatment of murine A498 xenografts with control, axitinib or X4P-001 as single agents, and with a combination of X4P-001 and axitinib. Treatment was initiated when tumor nodules reached ~7 mm mean diameter.

FIG. 3A-3D illustrate the increase in tumor cell death observed in the murine 498 xenograft model described in Example 1 in mice treated with control (FIG. 3A), axitinib (FIG. 3B) or X4P-001 (FIG. 3C) as single agents, or with a combination of X4P-001 and axitinib (FIG. 3D).

FIG. 4A shows the relative preponderance of expression of Ki-67 by tumor cells in the murine 786-0 xenograft model after treatment with control, axitinib or X4P-001 as single agents, and with a combination of X4P-001 and axitinib. FIG. 4B shows the relative preponderance of expression of CD34 by tumor cells in the murine 786-0 xenograft model after treatment with control, axitinib or X4P-001 as single agents, and with a combination of X4P-001 and axitinib. FIG. 4C shows the relative preponderance of expression of Ki-67 by tumor cells in the murine A498 xenograft model after treatment with control, axitinib or X4P-001 as single agents, and with a combination of X4P-001 and axitinib. FIG. 4D shows the relative preponderance of expression of CD34 by tumor cells in the murine A498 xenograft model after treatment with control, axitinib or X4P-001 as single agents, and with a combination of X4P-001 and axitinib. In all instances, the reduction in expression of Ki-67 and CD34 was significantly reduced ($p<0.05$) in mice treated with the combination compared to mice treated with X4P-001.

FIG. 5A shows the relative reduction in area of MDSC infiltration in xenografts in the murine 786-0 xenograft model after treatment with control, axitinib or X4P-001 as single agents, and with a combination of X4P-001 and axitinib. FIG. 5B shows the relative reduction in area of MDSC infiltration in xenografts in the murine A498 xenograft model after treatment with control, axitinib or X4P-001 as single agents, and with a combination of X4P-001 and axitinib. FIG. 5C shows the relative number of MDSC (CD11b+ GR-1+) cells infiltrating xenografts in the murine 786-0 xenograft model after treatment with control, axitinib or X4P-001 as single agents, and with a combination of X4P-001 and axitinib. FIG. 5D shows the relative number of MDSC (CD11b+ GR-1+) cells infiltrating xenografts in the murine A498 xenograft model after treatment with control, axitinib or X4P-001 as single agents, and with a combination of X4P-001 and axitinib.

FIG. 14A shows a Western blot of 786 cells treated with X4P-001 for 24 hours in normoxic and hypoxic (1% $O_2$) conditions. FIG. 14B illustrates mir-30a and mir-30c microRNA and (FIG. 14C) total HIF-2α RNA expression from the same cells from FIG. 14A.

DETAILED DESCRIPTION OF CERTAIN EMBODIMENTS OF THE INVENTION

Figure 2A:
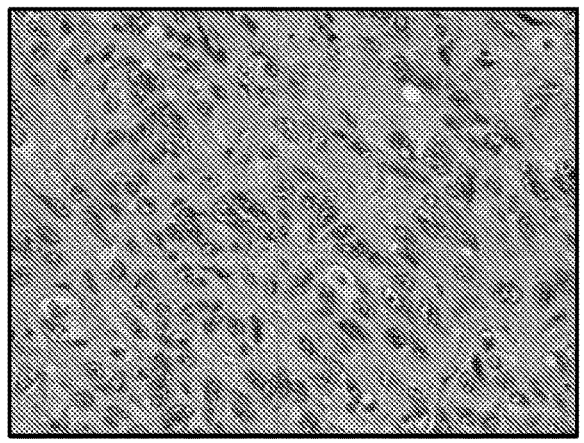
FIGS. 2A-2D illustrate the increase in tumor cell death observed in the murine 786-0 xenograft model described in Example 1 in mice treated with control (FIG. 2A), axitinib (FIG. 2B) or X4P-001 (FIG. 2C) as single agents, or with a combination of X4P-001 and axitinib (FIG. 2D).
Figure 2B:
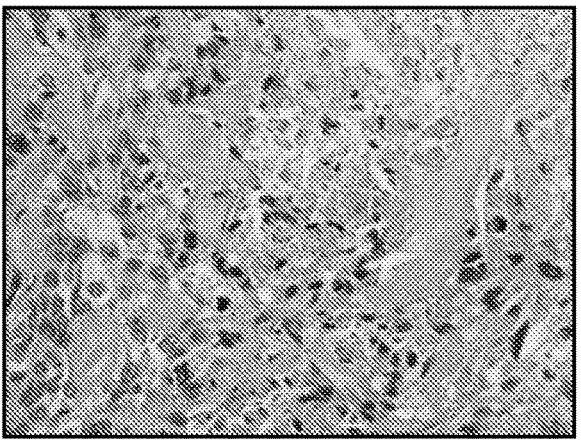
Figure 2C:
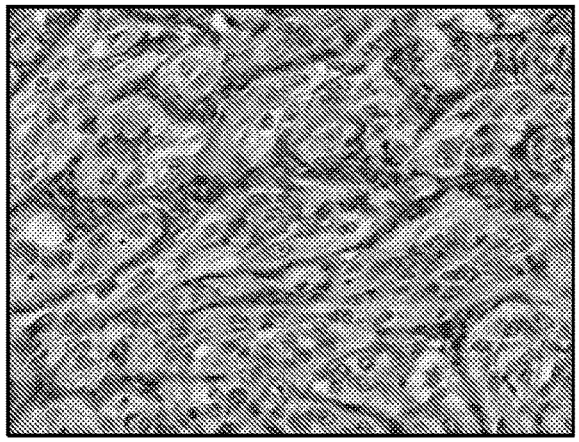
Figure 2D:
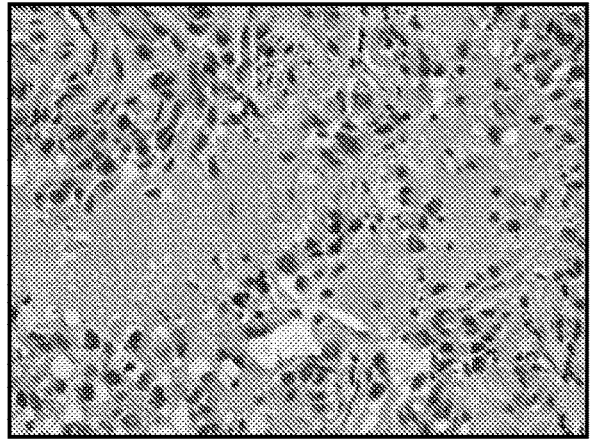
Figure 3D:
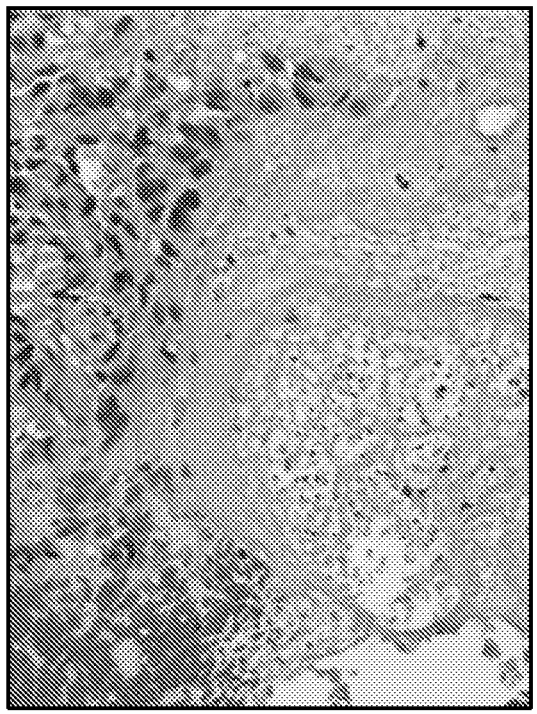
Figure 3C:
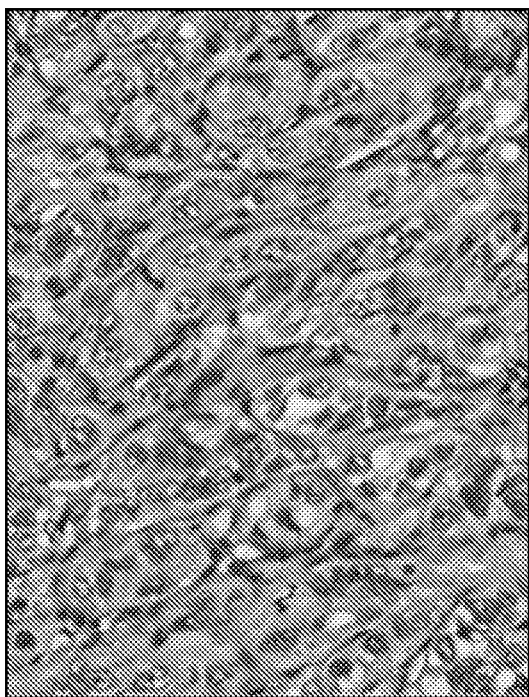

CXCR4 (C-X-C chemokine receptor type 4) is the receptor for CXCL12 (C-X-C chemokine ligand type 12; also referred to as SDF-1α, stromal-derived-factor 1α). CXCL12 has potent chemotactic activity for lymphocytes and MDSCs (myeloid-derived suppressor cells), and is important in homing of hematopoietic stem cells to the bone marrow. CXCR4 is also expressed and active on multiple types of human cancers, including ccRCC, ovarian cancer, and melanoma, and increased expression of CXCR4 on tumor cells has been associated with significantly decreased overall patient survival [3, 4, 5, 6].

Multiple observations implicate the CXCL12/CXCR4 axis in contributing to the lack (or loss) of tumor responsiveness to angiogenesis inhibitors (also referred to as "angiogenic escape"). In animal cancer models, interference with CXCR4 function has been demonstrated to disrupt the tumor microenvironment (TME) and unmask the tumor to immune attack by multiple mechanisms, including eliminating tumor re-vascularization [7, 8], and increasing the ratio of CD8+ T cells to Treg cells [7, 9, 10]. These effects result in significantly decreased tumor burden and increased overall survival in xenograft, syngeneic, as well as transgenic, cancer models [7, 9, 8].

X4P-001 is a potent, orally bioavailable CXCR4 antagonist [11], that has demonstrated activity in solid and liquid tumor models [12, and unpublished data] and has previously (under the designations AMD070 and AMD11070) been in Phase 1 and 2a trials involving a total of 71 healthy volunteers [11, 13, 14] and HIV-infected subjects [15, 16]. These studies demonstrated that oral administration of up to 400 mg BID for 3.5 days (healthy volunteers) and 200 mg BID for 8-10 days (healthy volunteers and HIV patients) was well-tolerated with no pattern of adverse events or clinically significant laboratory changes. These studies also demonstrated pharmacodynamic activity, with dose- and concentration-related changes in circulating white blood cells (WBCs); and a high volume of distribution (VL), suggesting high tissue penetrance.

Earlier work by some of the inventors on the mechanisms of acquired resistance to VEGF-targeted therapies, demonstrated that treatment with sunitinib treatment resulted in a marked increase in the infiltration of renal cell carcinoma (RCC) xenografts with CD11b+/Gr-1+ myeloid-derived suppressor cells (MDSC)(1). These cells have been repeatedly implicated in the development of resistance to a diverse array of anticancer therapies, including VEGF-targeted agents (2-5). The inventors further observed that the influx of MDSC, as well as the development of sunitinib resistance, could be prevented by the concurrent administration of the HDM2 antagonist MI-319 (Sanofi-Aventis), a drug whose biological effects are mediated primarily through the up regulation of p53. MDSC trafficking into tumor tissue is regulated by chemokines, many of which (e.g. SDF-1 and CXCL-12) are produced in response to hypoxia in a HIF-dependent manner. p53 is known to directly repress SDF-1 transcription (6) and the inventors have shown that MI-319 suppresses HIF-2 expression, suggesting that the drug may have both direct and indirect effects on SDF-1 expression. Based on these data, the inventors considered the possibility that MI-319 might mediate its effects on MDSC through the suppression of chemokine (e.g. SDF-1) production. Subsequent western blot analysis of tumor lysates confirmed this hypothesis.

These findings suggested that the ability of MI-319 to prevent sunitinib resistance might be due at least in part to the suppression of SDF-1 production and MDSC recruitment. To the extent that this is the case, the inventors conceived that agents that block SDF-1/CXCR4 signaling directly (e.g. AMD11070) could duplicate the effects of HDM2 blockade on MDSC trafficking and prevent sunitinib resistance.

Moreover, the inventors conceived that such a result might be achieved with comparatively little toxicity since, unlike HDM2 antagonists, CXCR4-targeted drugs would not be expected to induce cell cycle arrest in bone marrow and other normal proliferating cell populations. Accordingly, the present invention provides significant advantages in treatment outcomes utilizing the low toxicity and effects of the CXCR4 inhibitor AMD11070 (X4P-001) on MDSC trafficking, differentiation, and tumor cell gene expression in RCC.

It has now been found that CXCR4 antagonism by X4P-001 provides significant effects which may provide significant treatment benefits in patients with advanced ccRCC and other cancers by multiple mechanisms. Administration of X4P-001 decreased recruitment of MDSC, resulting in increased anti-tumor immune attack. Administration of X4P-001 additionally sustained decreases in neoangiogenesis and tumor vascular supply; and interferes with the autocrine effect of increased expression by ccRCC of both CXCR4 and its only ligand, CXCL12, thereby potentially reducing cancer cell metastasis. Administering X4P-001, a CXCR4 antagonist, sequentially (e.g. administered at the same time as separate unit dosage forms or administered as separate unit dosage forms at different times separated by up to 12 h) or concurrently (e.g. taken together) with a TKI inhibitor such as axitinib, blocks communication between the tumor and the MDSC, suppresses HIF-2α expression, reduces MDSC tumor infiltration, and appreciably improves the anti-tumor treatment effect.

In the present invention, patients with advanced forms of cancer, such as clear cell renal cell carcinoma (ccRCC) are treated with X4P-001, either as a single agent (monotherapy), or in combination with axitinib, a small molecule tyrosine kinase inhibitor (TKI) that is approved for second-line treatment of patients with ccRCC.

Without wishing to be bound by any particular theory, it is believed that by combining the two medicaments, the patients' treatment outcome can be further improved by reducing the angiogenic escape that typically occurs with TKI therapy.

In some embodiments, X4P-001, or a pharmaceutically acceptable salt thereof, is administered to a patient in a fasted state.

In some embodiments, the present invention provides a method for treating patients with cancer that presents as a solid tumor. In some embodiments, the patient has kidney cancer, renal tumor, renal carcinoma (including clear cell and papillary renal carcinoma), ovarian cancer, or melanoma.

In some embodiments, the present invention provides a method for treating refractory cancer in a patient in need thereof comprising administering X4P-001, or a pharmaceutically acceptable salt and/or composition thereof. In certain embodiments, the patient was previously administered a protein kinase inhibitor. In some embodiments, the patient was previously administered a VEGF-R antagonist. In some embodiments, the patient was previously administered a VEGF-R antagonist selected from axitinib (Inlyta) (Pfizer Inc., NY, USA), sorafenib (Nexavar® Bayer AG and Onyx); sunitinib (Sutent, Pfizer, New York, US); pazopanib (Votrient, GlaxoSmithKline, Research Triangle Park, US); cabozanitib (Cometriq, Exelexis, US); regorafenib (Stivarga, Bayer); lenvatinib (Lenvima, Eisai); bevacizumab (Avastin, Genentech, Inc. of South San Francisco, Calif.), an anti-VEGF monoclonal antibody; and aflibercept, also known as VEGF Trap (Zaltrap; Regeneron/Sanofi). Other kinase inhibitors/VEGF-R antagonists that are in development and may be used in the present invention include tivozanib (Aveo Pharmaeuticals, Cambridge, Mass.); vatalanib (Bayer, Novartis, Basel, Switzerland); lucitanib (Clovis Oncology); dovitinib (Novartis); CEP-11981 (Cephalon, US); linifanib (Abbott Laboratories, Abbott Park, US); PTC299 (PTC Therapeutics, South Plainfield, US); CP-547,632 (Pfizer); foretinib (Exelexis, GlaxoSmithKline); and motesanib (Amgen, Takeda).

In certain embodiments, the present invention provides a method for treating cancer in a patient in need thereof, wherein said method comprises administering to said patient X4P-001 in combination with a tyrosine kinase inhibitor. In certain embodiments, the X4P-001 and the tyrosine kinase inhibitor are administered simultaneously or sequentially. In certain embodiments, the tyrosine kinase inhibitor is selected from axitinib, sunitinib, sorafenib, pazopanib, cabozanitib or regorafenib. In a some embodiments of the invention, X4P-001 is administered in combination with axitinib.

Axitinib (Inlyta® Pfizer laboratories) is a kinase inhibitor. Axitinib has been shown to inhibit receptor tyrosine kinases including vascular endothelial growth factor receptors (VEGFR)-1, VEGFR-2, and VEGFR-3 at therapeutic plasma concentrations. These receptors are implicated in pathologic angiogenesis, tumor growth, and cancer progression. VEGF-mediated endothelial cell proliferation and survival were inhibited by axitinib in vitro and in mouse models. Axitinib was shown to inhibit tumor growth and phosphorylation of VEGFR-2 in tumor xenograft mouse models. Axitinib has the chemical name N-methyl-2-[3((E)-2-pyridin-2-yl-vinyl)-1H-indazol-6-ylsulfanyl]-benzamide.

The molecular formula is $C_{22}H_{18}N_4OS$ and the molecular weight is 386.47 Daltons. The chemical structure is depicted below.

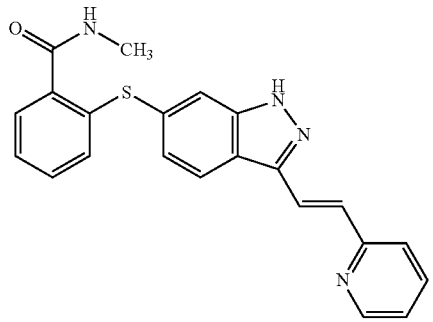 [SMILES: CNC(=O)c1ccccc1Sc1ccc2c(/C=C/c3ccccn3)n[nH]c2c1]

Axitinib is a white to light-yellow powder with a pKa of 4.8. The solubility of axitinib in aqueous media over the range pH 1.1 to pH 7.8 is in excess of 0.2 µg/mL. The partition coefficient (n-octanol/water) is 3.5.

Axitinib has been approved by the FDA for treatment of advanced renal cell carcinoma (RCC) after failure of one prior systemic therapy, i.e., as second line therapy. Axitinib has been tested or mentioned as a possible treatment in other oncologic indications. Accordingly, in some embodiments of the present invention, the cancer is selected from the group consisting of solid tumors (including solid fibrous tumors), neoplasms (including pancreatic, kidney, colorectal, lung, breast, thyroid and stomach neoplasms), glioblastoma, hepatocellular carcinoma or liver cancer, melanoma and intraocular melanoma, prostate cancer (including castrate-resistant prostate cancer), non-small cell lung cancer, renal tumor, renal carcinoma (including clear cell and papillary renal carcinoma) or kidney cancer, colorectal cancer, advanced gastric cancer, malignant mesothelioma, neurofibromatosis, including Schwannomatosis, soft tissue sarcoma, head and neck squamous cell carcinoma, nasopharyngeal carcinoma, adenocarcinoma, neuroendocrine carcinoma, acute myeloid leukemia, myelodysplastic syndrome, pheochromocytoma, paraganglioma, lymphoma, mantle-cell cancer, gastrointestinal-stromal tumors, or pancreatic ductal carcinoma.

In its current prescribed labeling for RCC, recommended starting oral dose of axitinib is 5 mg twice daily, approximately 12 hours apart. Depending upon individual tolerance, it is recommended that the prescribed dose of axitinib may be increased to 7 mg or 10 mg, twice daily; or reduced to 3 mg or 2 mg twice daily.

In some embodiments, the present invention provides a method for treating a refractory cancer in a patient in need thereof, wherein said method comprises administering to said patient X4P-001 in combination with a tyrosine kinase inhibitor. In some embodiments, the refractory cancer is ccRCC. In some embodiments, the refractory cancer is ccRCC and the tyrosine kinase inhibitor is axitinib.

In some embodiments, a provided method comprises administering the X4P-001, or a pharmaceutically acceptable salt thereof, is administered to a patient in a fasted state and administering the tyrosine kinase inhibitor to a patient in either a fasted or fed state.

In certain embodiments, the present invention provides a method for treating cancer in a patient in need thereof, wherein said method comprises administering to said patient X4P-001 in combination with a tyrosine kinase inhibitor, further comprising the step of obtaining a biological sample from the patient and measuring the amount of a disease-related biomarker. In some embodiments, the biological sample is a blood sample. In certain embodiments, the disease-related biomarker is circulating CD34+ cells and/or plasma levels of soluble VEGF-R.

In certain embodiments, the present invention provides a method for treating a refractory cancer in a patient in need thereof, wherein said method comprises administering to said patient X4P-001 in combination with a tyrosine kinase inhibitor, further comprising the step of obtaining a biological sample from the patient and measuring the amount of a disease-related biomarker. In some embodiments, the biological sample is a blood sample. In certain embodiments, the disease-related biomarker is circulating CD34+ cells and/or plasma levels of soluble VEGF-R.

In certain embodiments, the present invention provides a method for treating a refractory cancer in a patient in need thereof, wherein said method comprises administering to said patient X4P-001 in combination with axitinib, further comprising the step of obtaining a biological sample from the patient and measuring the amount of a disease-related biomarker. In some embodiments, the biological sample is a blood sample. In certain embodiments, the disease-related biomarker is circulating CD34+ cells and/or plasma levels of soluble VEGF-R.

In certain embodiments, the present invention provides a method for treating ccRCC in a patient in need thereof, wherein said method comprises administering to said patient X4P-001 in combination with axitinib, further comprising the step of obtaining a biological sample from the patient and measuring the amount of a disease-related biomarker. In some embodiments, the biological sample is a blood sample. In certain embodiments, the disease-related biomarker is circulating CD34+ cells and/or plasma levels of soluble VEGF-R.

In other embodiments of the invention, X4P-001 is administered in combination with a VEGF antagonist. The VEGF antagonist may be an antibody to VEGF or a VEGF trap. In certain embodiments, the VEGF antagonist is selected from bevacizumab or aflibercept.

In some embodiments, the present invention provides a method of treating cancer in a patient in need thereof, wherein said method comprises administering to said patient X4P-001 in combination with a tyrosine kinase inhibitor wherein the X4P-001 and the tyrosine kinase inhibitor act synergistically. One of ordinary skill in the art will appreciate that active agents (such as X4P-001 and a tyrosine kinase inhibitor) act synergistically when the combination of active agents results in an effect that is greater than additive. In some embodiments, the tyrosine kinase inhibitor is axitinib.

Dosage and Formulations

X4P-001 is a CXCR4 antagonist, with molecular formula $C_{21}H_{27}N_5$; molecular weight 349.48 amu; appearance white to pale yellow solid; solubility: X4P-001 is freely soluble in the pH range 3.0 to 8.0 (>100 mg/mL), sparingly soluble at pH 9.0 (10.7 mg/mL) and slightly soluble at pH 10.0 (2.0 mg/mL). X4P-001 is only slightly soluble in water; and melting point of 108.9° ΔC.

The chemical structure of X4P-001 is depicted below.

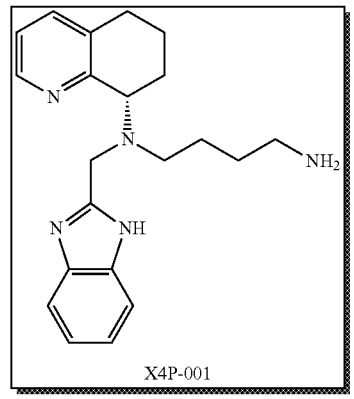

In certain embodiments, the composition containing X4P-001, or a pharmaceutically acceptable salt thereof, is administered orally, in an amount from about 200 mg to about 1200 mg daily. In certain embodiments, the dosage composition may be provided twice a day in divided dosage, approximately 12 hours apart. In other embodiments, the dosage composition may be provided once daily. The terminal half-life of X4P-001 has been generally determined to be between about 12 to about 24 hours, or approximately 14.5 hrs. Dosage for oral administration may be from about 100 mg to about 1200 mg once or twice per day. In certain embodiments, the dosage of X4P-0001, or a pharmaceutically acceptable salt thereof, useful in the invention is from about 200 mg to about 800 mg daily. In other embodiments, the dosage of X4P-001, or a pharmaceutically acceptable salt thereof, useful in the invention may range from about 200 mg to about 600 mg, from about 400 mg to about 800 mg, from about 600 mg to about 1000 mg or from about 800 mg to about 1200 mg daily.

In some embodiments, a provided method comprises administering to the patient a pharmaceutically acceptable composition comprising X4P-001 wherein the composition is formulated for oral administration. In certain embodiments, the composition is formulated for oral administration in the form of a tablet or a capsule. In some embodiments, the composition comprising X4P-001 is formulated for oral administration in the form of a capsule.

In certain embodiments, a provided method comprises administering to the patient one or more capsules comprising 10-1200 mg X4P-001 active ingredient; and one or more pharmaceutically acceptable excipients.

In certain embodiments, the present invention provides a composition comprising X4P-001, or a pharmaceutically acceptable salt thereof, one or more diluents, a disintegrant, a lubricant, a flow aid, and a wetting agent. In some embodiments, the present invention provides a composition comprising 10-1200 mg X4P-001, or a pharmaceutically acceptable salt thereof, microcrystalline cellulose, dibasic calcium phosphate dihydrate, croscarmellose sodium, sodium stearyl fumarate, colloidal silicon dioxide, and sodium lauryl sulfate. In some embodiments, the present invention provides a unit dosage form wherein said unit dosage form comprises a composition comprising 10-200 mg X4P-001, or a pharmaceutically acceptable salt thereof, microcrystalline cellulose, dibasic calcium phosphate dihydrate, croscarmellose sodium, sodium stearyl fumarate, colloidal silicon dioxide, and sodium lauryl sulfate. In certain embodiments, the present invention provides a unit dosage form comprising a composition comprising X4P-001, or a pharmaceutically acceptable salt thereof, present in an amount of about 10 mg, about 20 mg, about 25 mg, about 50 mg, about 75 mg, about 100 mg, about 150 mg, about 200 mg, about 250 mg, about 300 mg, about 400 mg, about 450 mg, about 500 mg, about 600 mg, about 700 mg, about 750 mg, about 800 mg, about 900 mg, about 1000 mg, about 1100 mg, or about 1200 mg. In some embodiments, a provided composition (or unit dosage form) is administered to the patient once per day, twice per day, three times per day, or four times per day. In some embodiments, a provided composition (or unit dosage form) is administered to the patient once per day or twice per day.

In some embodiments, the present invention provides a composition comprising:
(a) X4P-001, or a pharmaceutically acceptable salt thereof—about 30-40% by weight of the composition;
(b) microcrystalline cellulose—about 20-25% by weight of the composition;
(c) dibasic calcium phosphate dihydrate—about 30-35% by weight of the composition;
(d) croscarmellose sodium—about 5-10% by weight of the composition;
(e) sodium stearyl fumarate—about 0.5-2% by weight of the composition;
(f) colloidal silicon dioxide—about 0.1-1.0% by weight of the composition; and
(g) sodium lauryl sulfate—about 0.1-1.0% by weight of the composition.

In some embodiments, the present invention provides a composition comprising:
(a) X4P-001, or a pharmaceutically acceptable salt thereof—about 37% by weight of the composition;
(b) microcrystalline cellulose—about 23% by weight of the composition;
(c) dibasic calcium phosphate dihydrate—about 32% by weight of the composition;
(d) croscarmellose sodium—about 6% by weight of the composition;
(e) sodium stearyl fumarate—about 1% by weight of the composition;
(f) colloidal silicon dioxide—about 0.3% by weight of the composition; and
(g) sodium lauryl sulfate—about 0.5% by weight of the composition.

In some embodiments, the present invention provides a composition comprising:
(a) X4P-001, or a pharmaceutically acceptable salt thereof—about 8-25% by weight of the composition;
(b) microcrystalline cellulose—about 65-85% by weight of the composition;
(c) croscarmellose sodium—about 2-10% by weight of the composition;
(d) sodium stearyl fumarate—about 0.1-3% by weight of the composition; and
(e) colloidal silicon dioxide—about 0.05-0.7% by weight of the composition.

In some embodiments, the present invention provides a composition comprising:
(a) X4P-001, or a pharmaceutically acceptable salt thereof—about 25-45% by weight of the composition;
(b) microcrystalline cellulose—about 10-35% by weight of the composition;
(c) dibasic calcium phosphate dihydrate—about 15-45% by weight of the composition;
(d) croscarmellose sodium—about 2-10% by weight of the composition;
(e) sodium stearyl fumarate—about 0.3-2.5% by weight of the composition;
(f) colloidal silicon dioxide—about 0.05-1.2% by weight of the composition; and
(g) sodium lauryl sulfate—about 0.2-1.2% by weight of the composition.

In some embodiments, the present invention provides a composition comprising:
(a) X4P-001, or a pharmaceutically acceptable salt thereof—about 35-75% by weight of the composition;
(b) microcrystalline cellulose—about 5-28% by weight of the composition;
(c) dibasic calcium phosphate dihydrate—about 7-30% by weight of the composition;
(d) croscarmellose sodium—about 2-10% by weight of the composition;
(e) sodium stearyl fumarate—about 0.3-2.5% by weight of the composition;
(f) colloidal silicon dioxide—about 0.05-1.2% by weight of the composition; and
(g) sodium lauryl sulfate—about 0.2-1.2% by weight of the composition.

In some embodiments, the present invention provides a composition according to Table 1 or Table 2, below.

TABLE 1

25 mg Capsule Formulation

| Component | Reference to Standard | Function | Quantity (mg/capsule) | % w/w |
|---|---|---|---|---|
| X4P-001 | In-House | Active Ingredient | 25.0 | 14.7 |
| Microcrystalline Cellulose | NF | Diluent | 132.7 | 78.1 |
| Croscarmellose Sodium | NF | Disintegrant | 10.2 | 6.0 |
| Sodium Stearyl Fumarate | NF | Lubricant | 1.7 | 1.0 |
| Colloidal Silicon Dioxide | USP | Flow Aid | 0.4 | 0.2 |
| Sum Total | | | 170.0 | 100.0 |
| Hard Gelatin Capsules, Size 1 | USP | Packaging | NA | NA |

TABLE 2

100 mg and 200 mg Capsule Formulations

| | 200 mg | | 100 mg | |
|---|---|---|---|---|
| Ingredients | Percent Per Capsule (%) | Theoretical Amount Per Capsule (mg) | Percent Per Capsule (%) | Theoretical Amount Per Capsule (mg) |
| X4P-001 Drug Substance | 61.5 | 200.0 | 37.6 | 100 |
| Microcrystalline Cellulose, NF/EP (Avicel PH 101) or equivalent | 12.9 | 41.93 | 22.9 | 60.9 |
| Dibasic Calcium Phosphate Dihydrate, USP/NF | 17.8 | 57.85 | 31.7 | 84.3 |

TABLE 2-continued 100 mg and 200 mg Capsule Formulations

| Ingredients | 200 mg | | 100 mg | |
|---|---|---|---|---|
| | Percent Per Capsule (%) | Theoretical Amount Per Capsule (mg) | Percent Per Capsule (%) | Theoretical Amount Per Capsule (mg) |
| Croscarmellose Sodium, NF/EP (Ac-Di-Sol) | 6.0 | 19.50 | 6.0 | 16.0 |
| Sodium Lauryl Sulfate, NF/Ph. Eur. | 0.5 | 1.625 | 0.5 | 1.3 |
| Colloidal Silicone Dioxide, NF/Ph. Eur. (Cab-O-Sil M-5P) | 0.3 | 0.9750 | 0.3 | 0.8 |
| Sodium Stearyl Fumarate, NF (Pruv) | 1.0 | 3.250 | 1.0 | 2.7 |
| Total Capsule Fill | 100 | 325.0 | 100 | 266.0 |

In some embodiments, the present invention provides a unit dosage form comprising a composition described above. In some embodiments, the unit dosage form is a capsule.

Inasmuch as it may be desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for co-administration of the compositions. Thus the kit of the invention includes two or more separate pharmaceutical compositions, at least one of which contains a compound of the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically includes directions for administration and may be provided with a memory aid.

The examples below explain the invention in more detail. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

The contents of each document cited in the specification are herein incorporated by reference in their entireties.

EXEMPLIFICATION

Example 1: Murine Models with Human Cell Lines

The effects were examined of treatment with X4P-001 and axitinib singly, and in combination on the trafficking of MDSC and other immunosuppressive cell populations and on chemokine production by RCC cells.

Mice were inoculated with 786-0 and A498 RCC xenografts, the tumors permitted to grow to ~300 mm$^3$, and then treatment initiated with the CXCR4 inhibitor X4P-001, axitinib, both agents in combination, or saline (control).

With each of the human cell lines, 1×107 tumor cells were implanted subcutaneously in the flanks of 36 nude/beige mice and tumors allowed to grow to roughly 7 mm in diameter. The mice were randomly divided into 4 treatment groups of 9 mice each and treated with X4P-001 (at the recommended dose), axitinib (30 mg/kg daily by gavage), both drugs, or vehicle (control). We have previously shown that MDSC tumor influx is maximal at 7 days (not shown). Therefore, on day 7, the mice were sacrificed and the tumors were measured and immediately excised and divided into three parts. One part of each tumor was paraffin-embedded for dual color immunofluorescence. Another part was mechanically disaggregated and treated with collagenase/DNAse to generate a single cell suspension for flow cytometry. The third part was frozen for future pharmacokinetic analysis. Microscope slides were made from the paraffin-embedded tumor tissue, which were stained with antibodies against CD11b, Gr-1, and FAP. The number of infiltrating CD11b+/Gr-1+ MDSC and FAP+ fibroblasts present in the tumor tissue was then determined by immunofluorescence (IF) as previously described (1).

The disaggregated tumor specimens were analyzed for CD11b+/Gr-1+ MDSC and FAP+ fibroblasts by flow cytometry. The fraction of both populations expressing CXCR4 were also determined. At the time the mice were sacrificed, the spleens were removed and cut in half. One part was disaggregated into single cell suspensions and analyzed by flow cytometry as above for MDSC. The second half was frozen for future analyses, such as PK analysis. Finally, a bone marrow (BM) sample was generated by extruding marrow from an excised femur with a syringe filled with saline and analyzed by flow cytometry for MDSC.

Figure 4B:
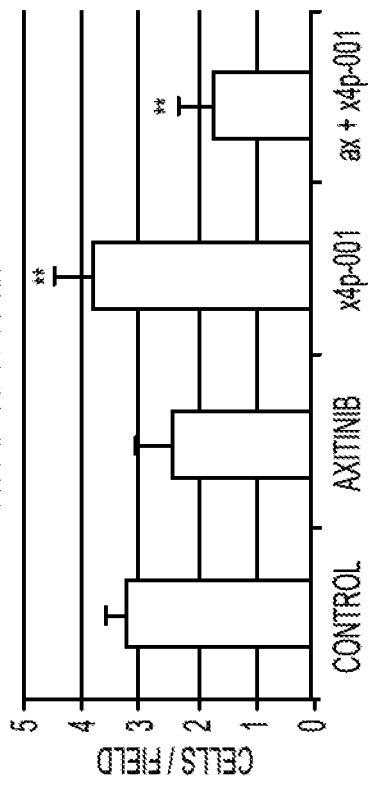
FIGS. 4A-4D illustrate the decreased presence of Ki-67+ and CD34+ cells observed in two murine models of tumor xenografts described in Example 1 that have been treated with a combination of X4P-001 and axitinib.
Figure 4D:
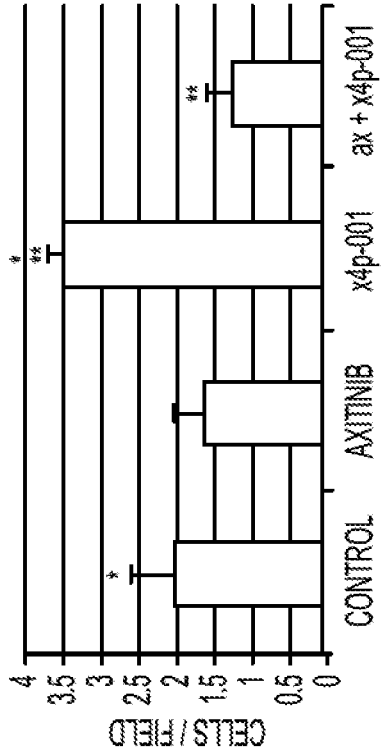
Figure 4A:
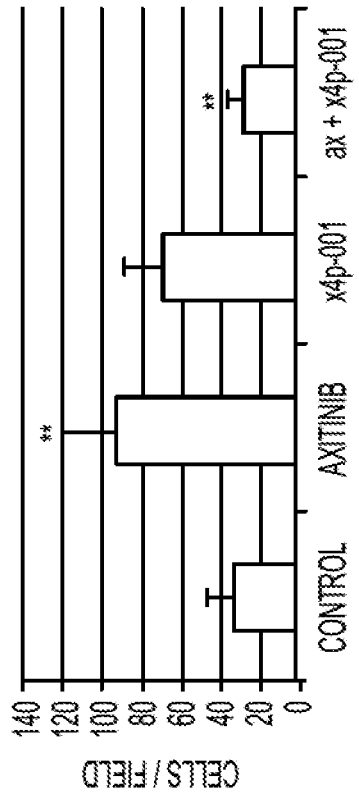
Figure 4C:
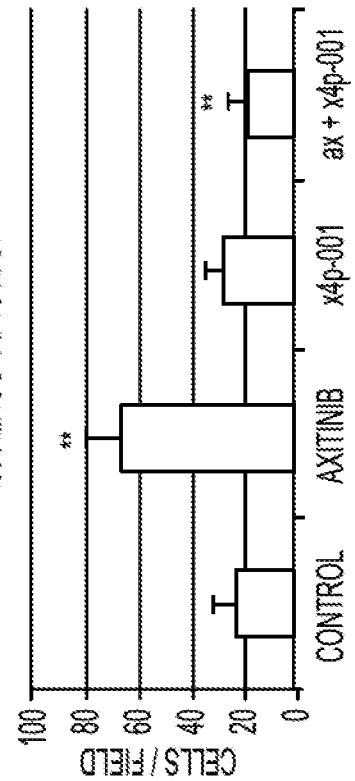
Figure 5A:
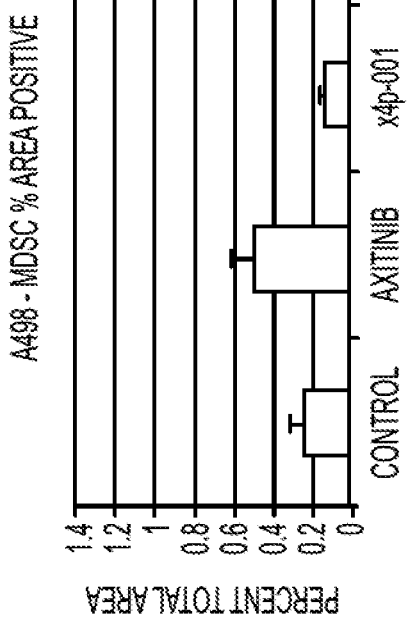
FIGS. 5A-5D illustrate the significantly reduced MDSC infiltration observed in two murine models of tumor xenografts described in Example 1 in mice that have been treated with a combination of X4P-001 and axitinib.
Figure 5B:
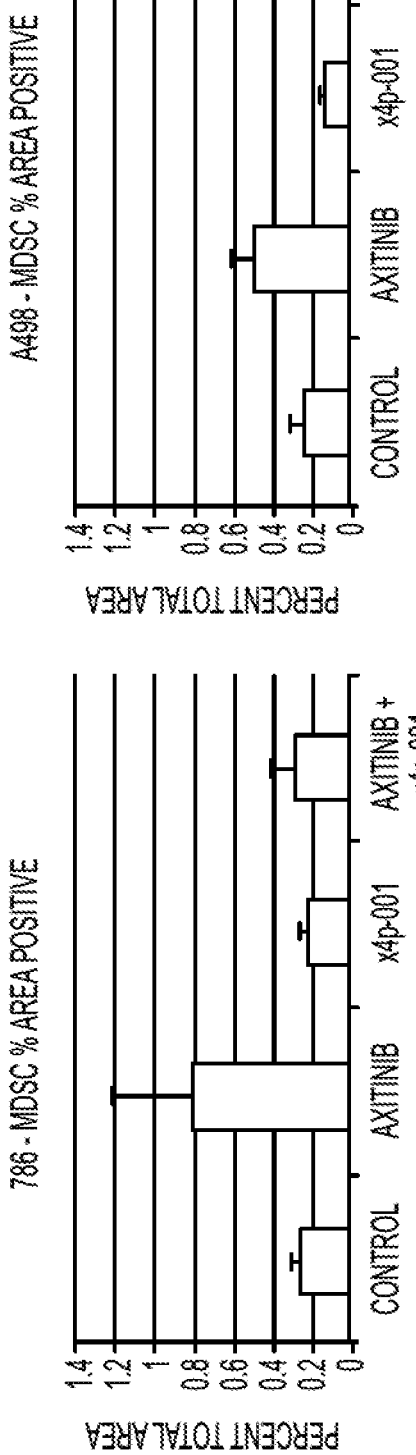
Figure 5C:
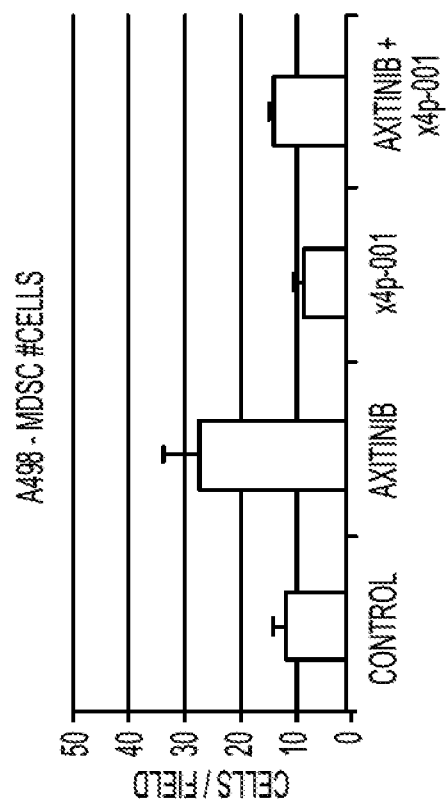
Figure 5D:
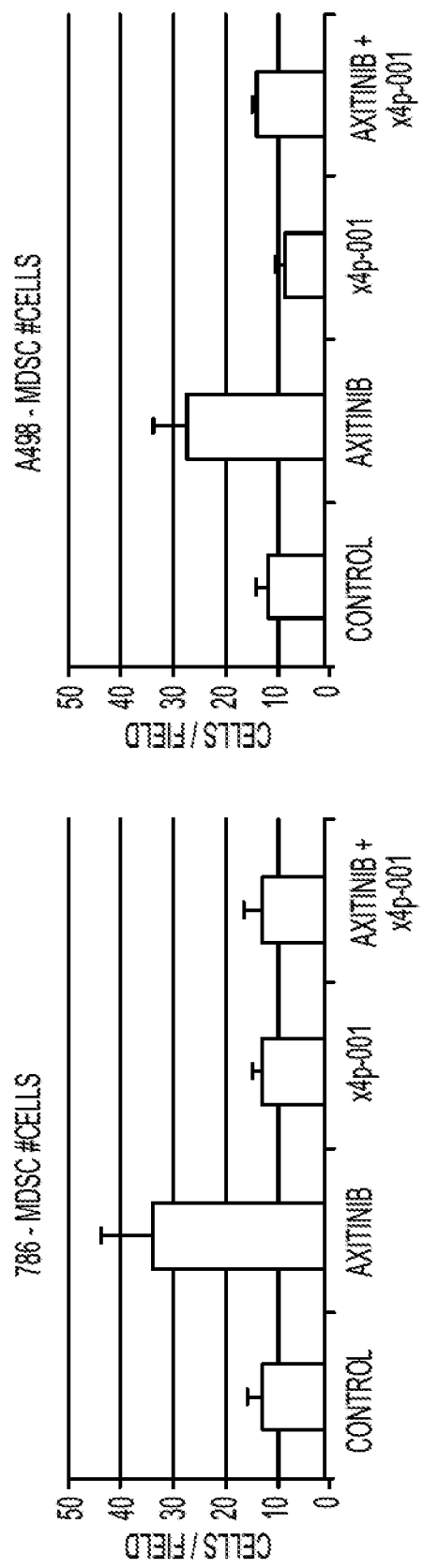
Figure 6:
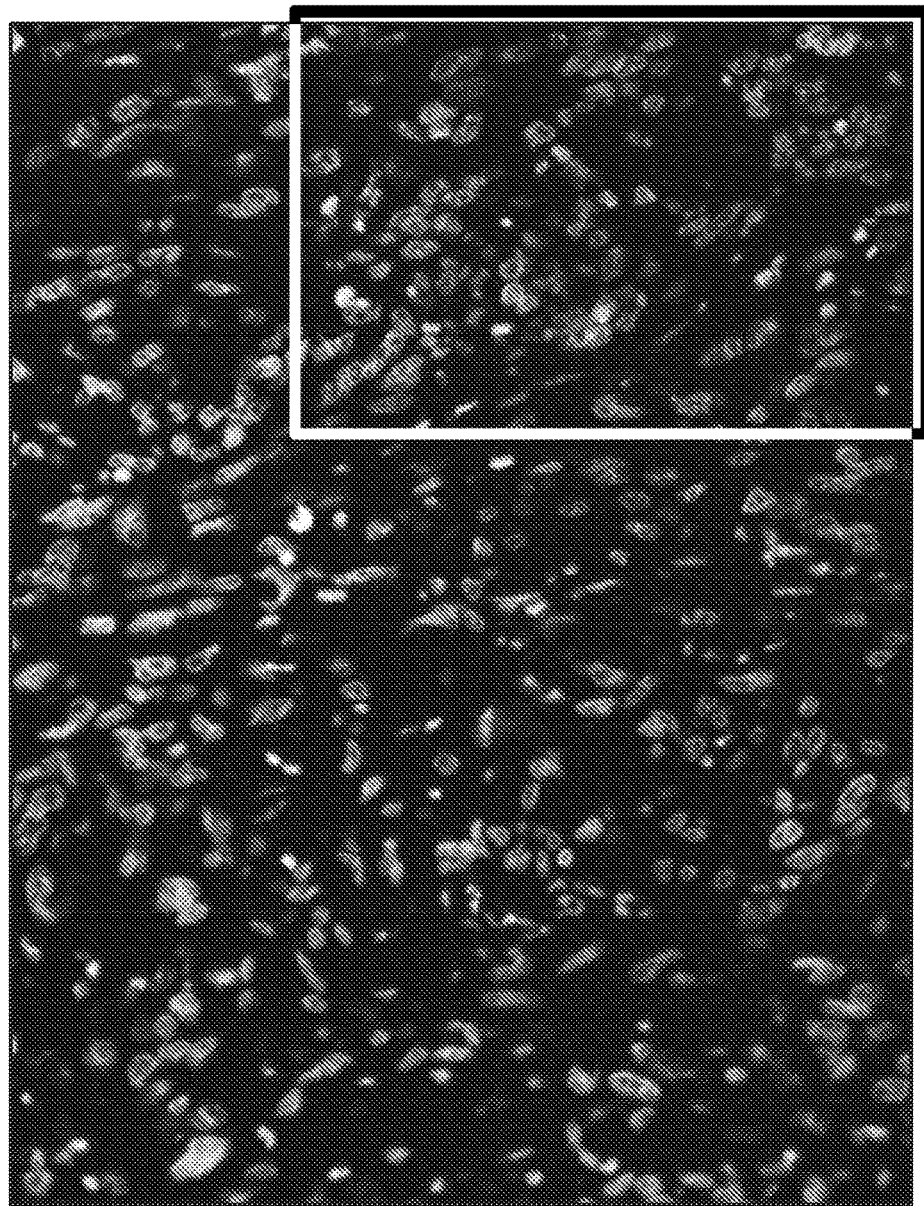
FIG. 6 and FIG. 7 illustrate through immunofluorescence (IF) the MDSC (CD11b+ GR-1+) infiltrating 786-0 xenografts treated with axitinib alone under low power (FIG. 6) and high power (FIG. 7), respectively.
Figure 7:
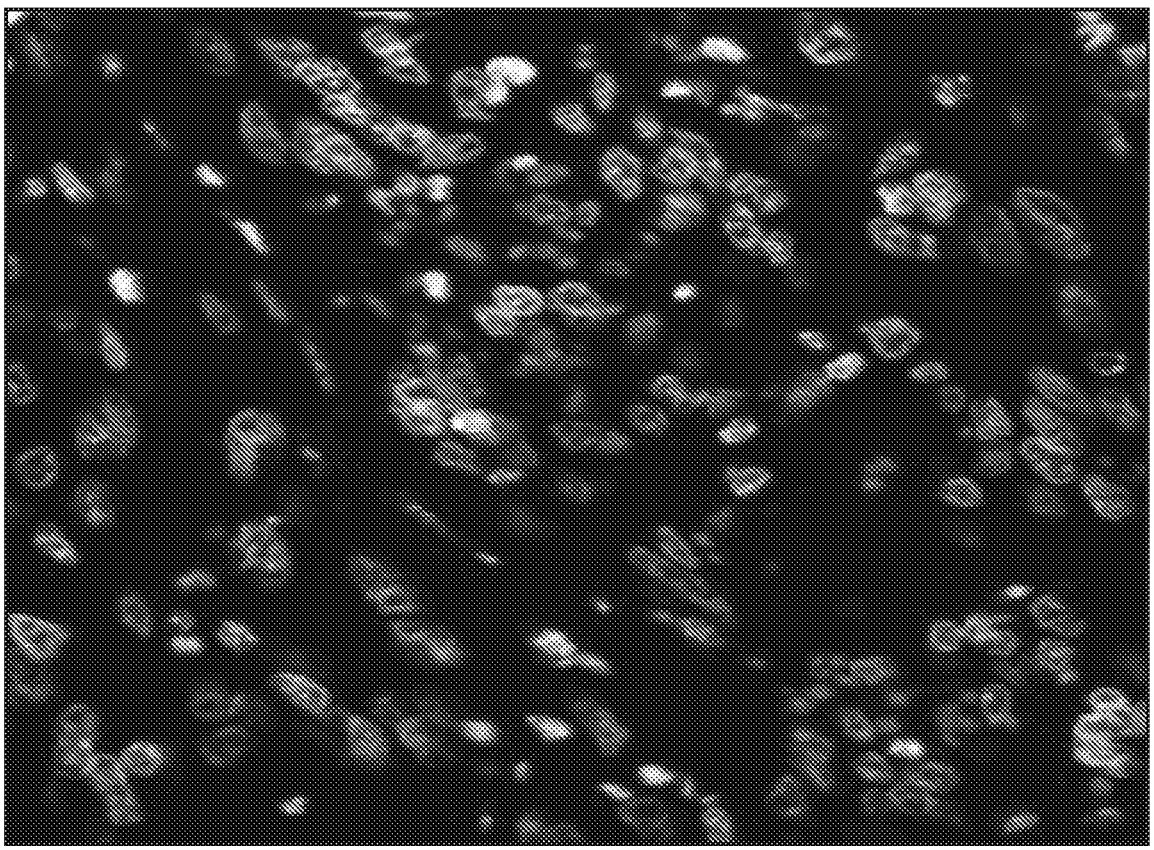

Results:

Whereas either drug alone either had no (axitinib) or modest (X4P-001) effects on tumor growth, the combination of X4P-001 and axitinib had additive and/or synergistic antitumor effects. Specifically, combination treatment resulted in massive tumor cell death, with the established implants actually regressing in size (See FIGS. 1A and 1B)—an effect not previously seen with VEGFR-targeted drugs given as single agents. IHC staining demonstrated, as previously, that mice treated with axitinib alone had an increase in Ki-67 positive tumor cells (See FIGS. 4A and 4C). This effect was not observed in mice that received both X4P-001 plus axitinib (See FIGS. 4A and 4C), suggesting an anti-proliferative effect of the combination. Finally, the tumors from mice receiving axitinib alone had extensive MDSC infiltration (see FIGS. 5A through 5D, whereas the tumors from mice receiving either X4P-001 alone or the axitinib/X4P-001 combination had significantly less MDSC infiltration (see FIGS. 5A through 5D).

Figure 11:
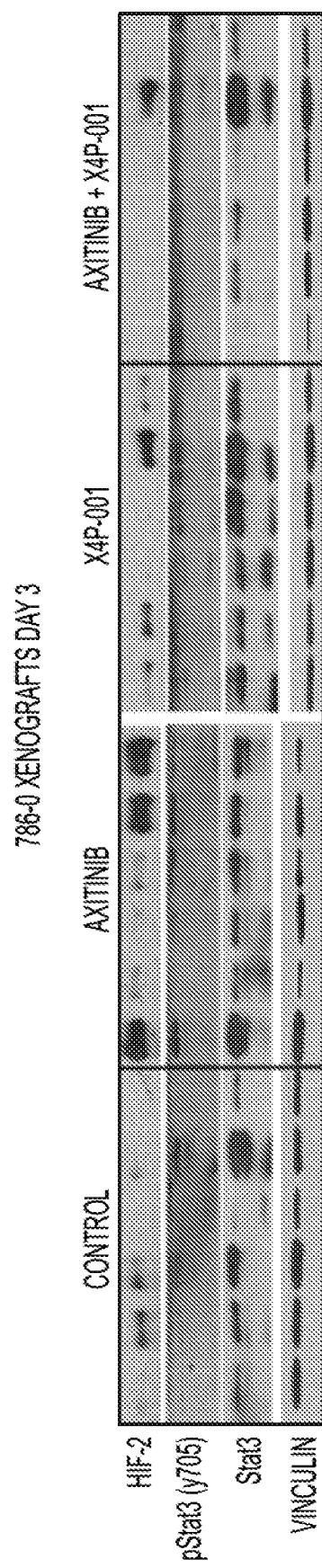
FIG. 11 illustrates Western blots of 786 xenografts treated with X4P-001 showed reduction in the level of HIF-2α relative to that caused by axitinib treatment.
Figure 12:
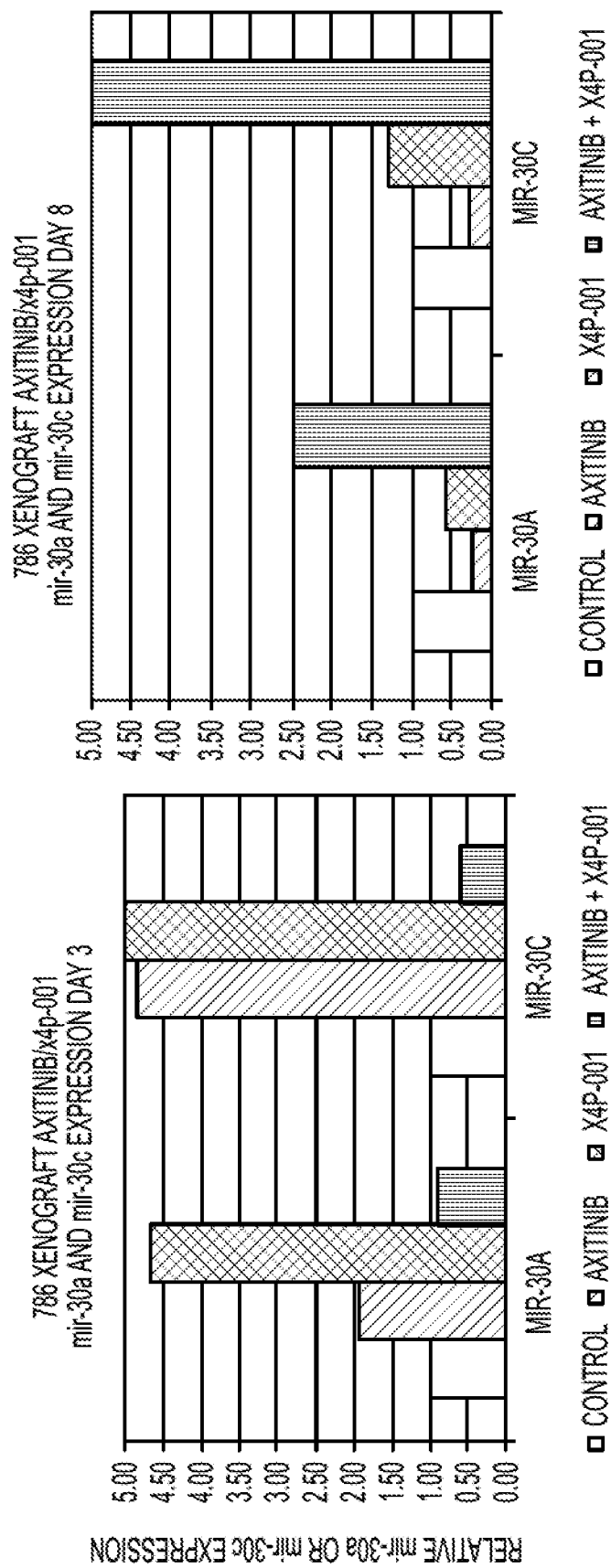
FIG. 12 illustrates that axitinib suppressed the microRNAs mir-30a and mir-30c, and the addition of X4P-001 to axitinib resulted in increased mir-30a and mir-30c after 8 days of treatment (786-0 xenograft tumor). mir-30a and mir-30c microRNA and HIF-2α mRNA expression from tumors of xenografts treated with axitinib +/−X4P-001. Data is presented as mir-30a or mir-30c expression relative to the mean control value (left side) and relative HIF-2α RNA expression.
Figure 13:
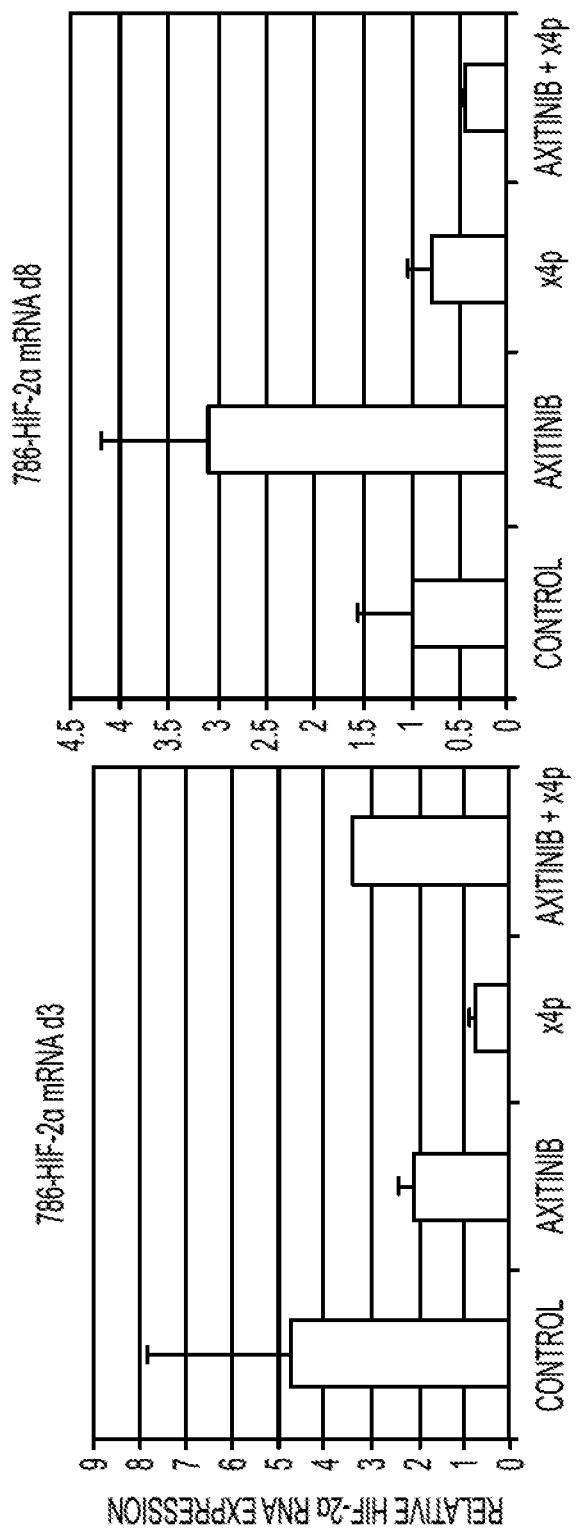
FIG. 13 illustrates that axitinib and X4P-001 together act to reduce HIF-2α expression after 8 days of treatment in 786 xenograft tumors.

Suppression of miRNAs mir-30a and mir-30c and Effect on HIF-2α in Xenografts:

As shown in FIG. 11, Western blots of 786 xenografts treated with X4P-001 showed reduction in the level of HIF-2α relative to that caused by axitinib treatment. Furthermore, as shown in FIGS. 12 and 13, axitinib suppressed the micro-RNAs mir-30a and mir-30c, and the addition of X4P-001 to axitinib resulted in increased mir-30a and mir-30c after 8 days of treatment (786-0 xenograft tumor). mir-30a and mir-30c microRNA and HIF-2α mRNA expression from tumors of xenografts treated with axitinib +/−X4P-001. Data is presented as mir-30a or mir-30c expression relative to the mean control value (left side) and relative HIF-2α RNA expression. FIG. 13 illustrates that axitinib and X4P-001 together act to reduce HIF-2α expression after 8 days of treatment in 786 xenograft tumors.

Figure 14:
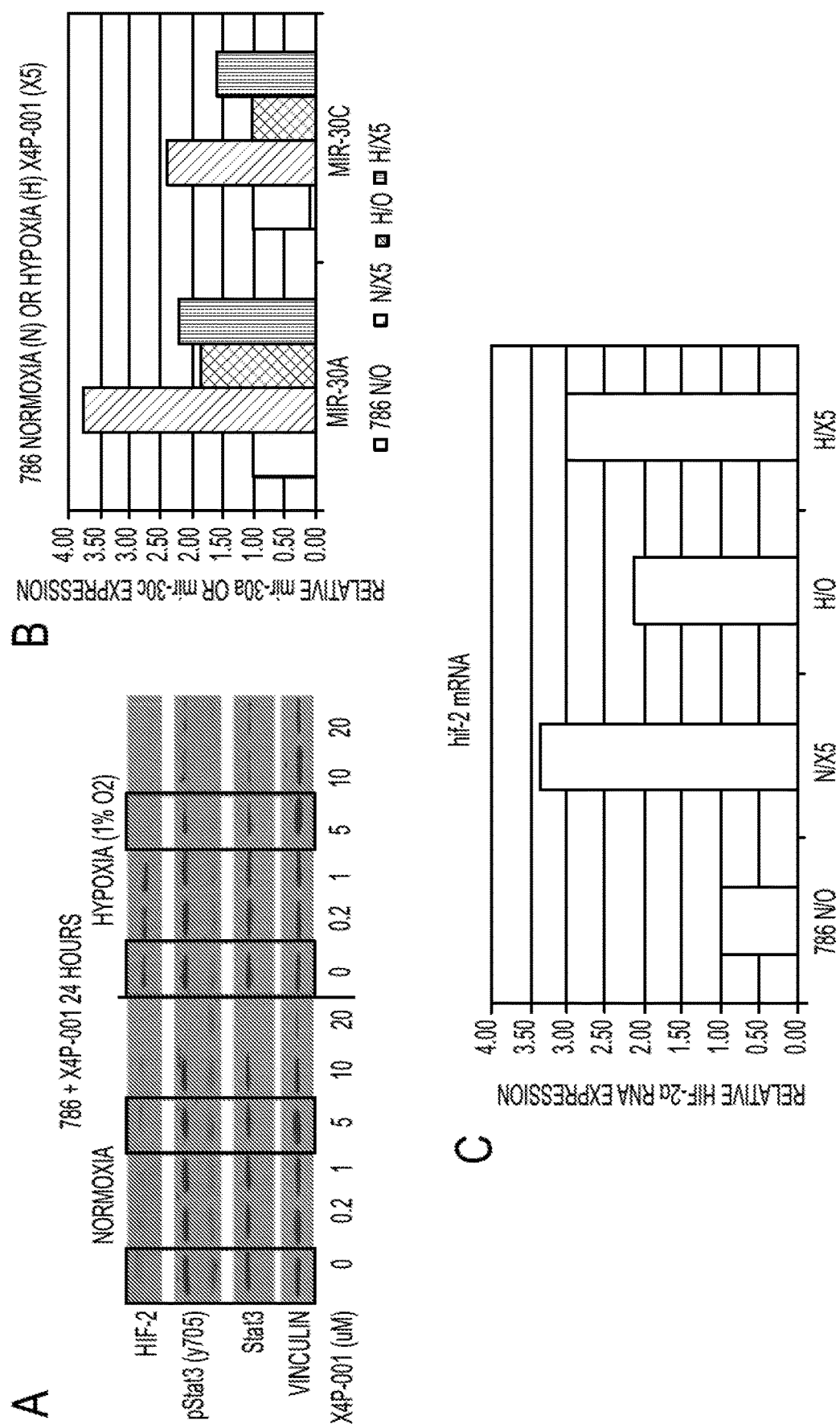
FIGS. 14A-C illustrate the effect of X4P-001 treatment on 786 hypoxic cells in vitro on mir-30a and mir-30c induction and HIF-2α reduction.

FIGS. 14A-C illustrate the effect of X4P-001 treatment on 786 hypoxic cells in vitro on mir-30a and mir-30c induction and HIF-2α reduction. FIG. 14A shows a Western blot of 786 cells treated with X4P-001 for 24 hours in normoxic and hypoxic (1% $O_2$) conditions. FIG. 14B illustrates mir-30a and mir-30c microRNA and (FIG. 14C) total HIF-2α, RNA expression from the same cells from FIG. 14A.

Figure 15:
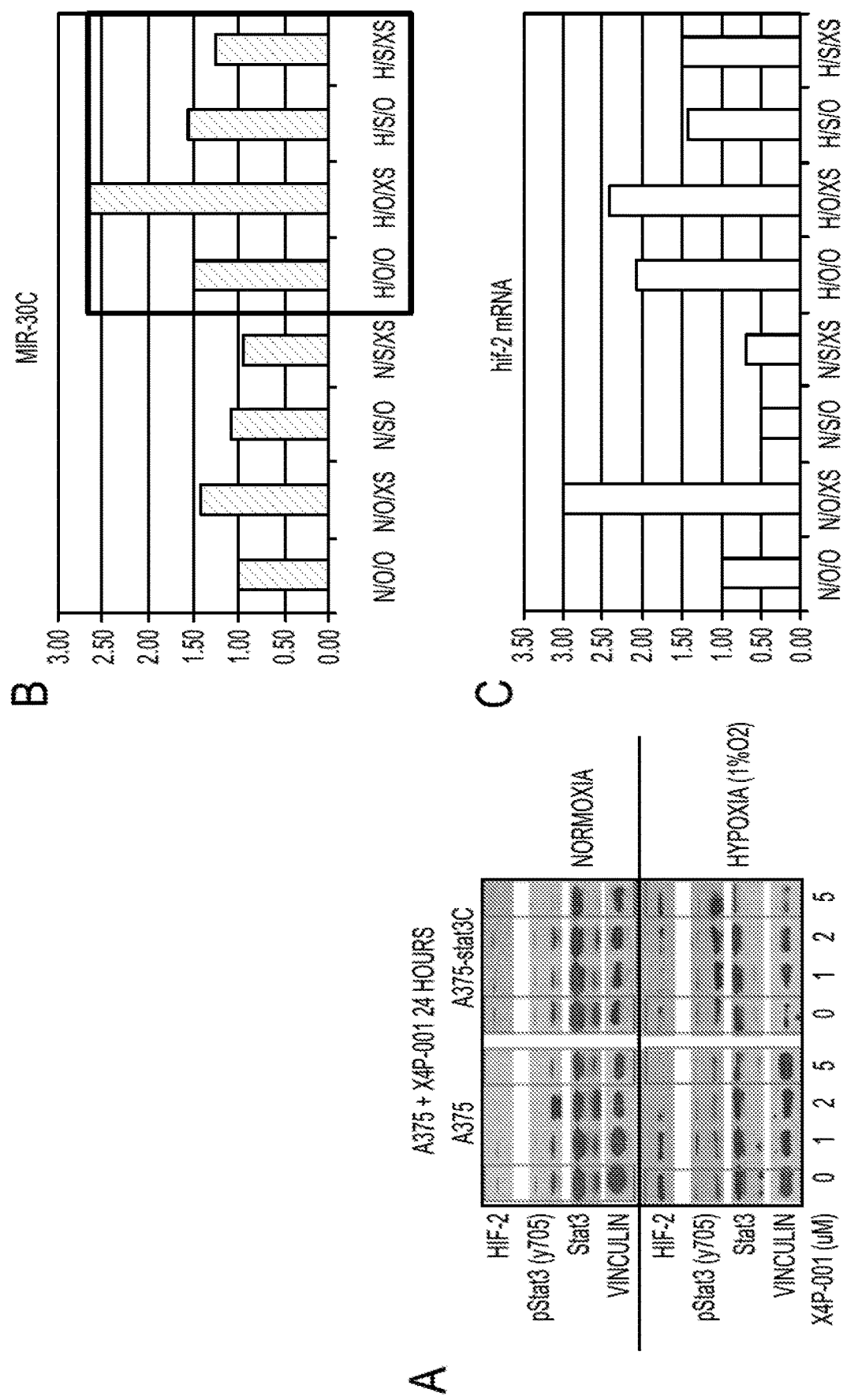
FIG. 15A illustrates Western blot results from lysates of A375 cells or A375 cells transfected with a constitutively active Stat3 construct. Cells were treated with X4P-001 for 24 h in normoxic or hypoxic conditions.
FIG. 15B shows mir-30c microRNA and FIG. 15C shows total RNA expression from the same cells from FIG. 15A. The suppression of HIF-2α and induction of mir-30a and 30c is thus dependent on Stat3 expression. Stat3 is known to be important in promoting CXCL12-mediated invasion of tumors.

FIG. 15A illustrates Western blot results from lysates of A375 cells or A375 cells transfected with a constitutively active Stat3 construct. Cells were treated with X4P-001 for 24 h in normoxic or hypoxic conditions. FIG. 15B shows mir-30c microRNA mid FIG. 15C shows total RNA expression from the same cells from FIG. 15A. The suppression of HIF-2α and induction of mir-30a and 30c is thus dependent on Stat3 expression. Without wishing to be bound by theory, it is believed that Stat3 is important in promoting CXCL-12 mediated invasion of tumors.

What these results show is that axitinib suppressed the micro-RNAs mir-30a and mir-30c, which, without wishing to be bound by theory, are believed to inhibit HIF-2α translation. The addition of X4P-001 to axitinib in vivo and in hypoxic cells in vitro results in increased mir-30a and mir-30c.

Example 2: Further Xenograft Studies

Further studies are conducted in order to determine how treatment with X4P-001 and axitinib alone or in combination affects the distribution of MDSC and other immunosuppressive CXCR4+ cell populations (Tregs and CAF) and how CXCR4 expression by these cells affects their trafficking in tumor-bearing mice. Example 1 above is repeated with additional testing of syngeneic murine RCC Renca model and 786-M1A cells, the latter of which is a 786-0 variant known to express CXCR4 at extremely high levels (7). The studies with Renca cells are done as described above for the human cell lines except that tumors are also analyzed for CD4+/CD25bright/Foxp3+ Tregs, CD3+/CD8+ T cells in addition to MDSC and fibroblasts.

Following the procedures of Example 1, the effects of treatment with X4P-001 and axitinib on bone marrow, spleen, and tumor infiltration by CD11b+/Gr-1+ MDSC, CD4+/CD25bright/Foxp3+ Tregs, CD3+/CD8+ T cells, and FAP+ cancer-associated fibroblasts (CAF) are examined and the levels of CXCR4 expression on these cells are determined.

Example 3: Cytokine and Chemokine Studies

The in vivo effects of treatment with X4P-001 and axitinib on chemokine production by RCC cells are assessed as follows:

Tumors excised from the mice undergoing treatment with X4P-001 and axitinib in Example 1 are analyzed by RT-PCR for drug-induced changes in the expression of M-CSF (CSF-1), CXCL1 (MGSA/gro-), CXCL2 (MIP-2/gro-), MIP-2/gro-, CXCL5 (ENA-78), CXCL6 (GCP-2), CXCL8 (IL-8), GM-CSF, VEGF, TNF, CCL22, and CCL28. The various ELR-containing CXCL chemokines listed are known to activate CXCR2 (8), a chemokine receptor recently implicated in MDSC recruitment (9). The cytokines VEGF, GM-CSF, and TNF are also thought to mediate MDSC chemotaxis into tumor tissue. CCL22 and CCL28 have been likewise implicated in the recruitment of Tregs (10, 11).

Numerous chemokines and other inflammatory mediators have been shown to regulate the trafficking of MDSC into tumor tissue (9, 12, 13). To determine which chemokines/cytokines are responsible for the influx of MDSC into RCC during treatment with VEGF-targeted therapies, CD11b+/Gr-1+ MDSC are isolated from the spleens of tumor-bearing mice undergoing treatment with axitinib. The MDSC are then infected with a small pooled lentiviral shRNA library (DeCode GIPZ, Thermo Scientific) for a select group of G protein-coupled and other receptors known to regulate MDSC trafficking. The library will include shRNAs for TNFR-1 and -2, IL-4R, and whole array of CXCR and CCR chemokine receptors (CXCR1-5, CCR 1-9). Several of these (e.g. CXCR-1, -2, and -4) engage chemokines known to promote MDSC recruitment (9, 12, 13).

Example 4: Pharmacokinetics Studies

In order to evaluate the pharmacokinetic properties of combined therapy with X4P-001 and axitinib, levels of X4P-001 and axitinib in blood, tumor tissue, and spleen are measured 4 hr after dosing. To measure drug levels in blood, spleen, and tumor tissue, blood is collected by ventricular puncture at the time the mice are sacrificed—4 hrs after the day 7 drug dosing. The blood samples as well as the spleen and tumor tissue are then subjected to PK analysis.

Example 5: Clinical Treatment Regimens

X4P-001 at a determined dose from 200 mg to 1200 mg daily is administered orally either once daily or twice daily in divided doses. Patients are instructed about both dosing schedule and requirements relating to food or drink near the time of dosing.

Dosing Schedule. The first daily dose is taken in the morning and the second daily dose approximately 12 hours later using the following guidelines:

Dosing should be at the same times each day 2 hr.
For twice daily dosing, the interval between successive doses should not be <9 hours nor >15 hours. If the interval would be >15 hrs, the dose should be omitted and the usual schedule resumed at the next dose.
Restrictions relating to food. Absorption is impacted by food and patients will be instructed as follows:
For the morning dose
No food or drink (except water) after midnight until the time of dosing
No food or drink (except water) for 2 hours after dosing.
For the second daily dose, if applicable
No food or drink (except water) for 1 hour before dosing
No food or drink (except water) for 2 hours after dosing.

Axitinib is administered consistent with prescribed labeling information. Initial treatment with axitinib is at 5 mg orally BID in addition to X4P-001 at the determined dose level. Administration of axitinib. Axitinib may be taken at the same time as axitinib. Alternatively, since axitinib has been associated with gastrointestinal adverse events and its absorption is not altered by food (see current product label), patients may, with the approval of their clinician, take the axitinib separately, following the same BID dosing schedule guidelines noted.

Dosing of X4P-001 and/or axitinib may be adjusted by the clinician as appropriate. The dose of X4P-001 and/or axitinib may be lowered according to the judgment of the clinician. If a patient receiving X4P-001 in combination with axitinib experiences an adverse event at Grade >2, the dose of X4P-001 and/or axitinib may be lowered according to the judgment of the clinician. If a patient successfully completes the first 4 weeks of treatment, that is, without experiencing any adverse events greater than Grade 2, the daily dose of X4P-001 and/or axitinib may be increased consistent with the judgment of the clinician.

Evaluation of Response to Treatment and Disease Status

Classification of tumor response may be performed according to codified tumor response evaluation, according to the Response Evaluation Criteria in Solid Tumors Group ("RECIST"), as described in Therasse et al. (2000), J. National Cancer Institute, 92:205-216. Radiologic assessment of ccRCC is accomplished by Computed Tomography (CT) with slice thickness ≤5 mm and contrast. CT is performed prior to treatment (baseline) and may be made at intervals during treatment to determine the response.

Key Terminology:

Measurable non-nodal lesions—≥10 mm in longest diameter.

Measurable nodal lesions—≥15 mm in short axis

Nonmeasurable lesions—lesions that are smaller, including those that cannot be measured.

Measurable disease—presence of at least one measurable lesion.

Target Lesions

At baseline, four (4) measureable lesions, two (2) for each individual organ, are identified, documented, and the appropriate diameter of each is recorded. If measurable extra-renal lesions are present, a measurable extra-renal lesion is also identified, documented, and the appropriate diameter is recorded. Lesions are selected based on size, to be representative of disease, and suitable for reproducible repeat measurement. Target lesions may include measurable lymph nodes.

During treatment, each target lesion is assessed for Complete Response, Partial Response, Stable Disease, or Progressive Disease as follows:

Complete Response (CR)
(a) Disappearance of all non-nodal lesions, and
(b) Absence of pathologic lymph nodesa.
Partial Response (PR)
(a) ≥30% decrease from baseline in the SOD of the target lesions
Stable Disease (SD)
(a) Persisting disease that does not meet criteria for either PR or PD Progressive Disease (PD)
a) ≥20% increase in the SOD of the target lesions, compared to the smallest sum, which may be either at baseline or while on treatment; and
(b) an absolute increase of ≥5 mm in the SOD.
Non-Target Lesions All other lesions present at baseline, including pathologic nodes (defined as nodes >10 mm in short axis) should be documented (quantitative measurements are not required) so that they can be classified on follow-up as present, absent, or unequivocal progression.

Complete Response (CR)
(a) Disappearance of all non-target lesions, and
(b) Absence of pathologic lymph nodesa.
Non-CR/Non-PD
Persistence of one or more non-target lesions
Progressive Disease (PD)
Unequivocal progression of existing non-target lesions.

[Note: $^a$=All lymph nodes, whether or not designated target or non-target lesions, have short axis diameter ≤10 mm.]

New Lesions

A new lesion should be unequivocal (e.g., not attributable to variation in technique); includes lesions in a location not scanned at baseline.

Pharmacokinetic Assessments

If desired, pharmacokinetic assessment of blood samples for plasma levels of X4P-001 and axitinib may be conducted. Blood samples are collected as scheduled. Samples are analyzed for X4P-001 concentration using reversed-phase high performance liquid chromatography (RP-HPLC) with MS/MS detection. The validated range of this bioanalytic method is 30 to 3,000 ng/mL in plasma.

Pharmacokinetic assessment of axitinib may be accomplished using techniques such as described in Tortorici et al., (2011) Invest. New Drugs 29:1370-1380, the full disclosure of which is hereby specifically incorporated herein by reference.

Example 6: Formulation Trial Results for X4P-001

This Example summarizes pilot trial results on chosen formulation for each of the 3 dose strengths for X4P-001. The powder blend containing AFT, fillers/diluents, a disintegrant, a glidant and a lubricant was prepared and filled into size 1 hard gelatin capsules on an automated capsule filling machine. The process developed for all 3 formulations showed adequate flowability, acceptable weight variation and content uniformity. All 3 formulations showed more than 90% release after 45 minutes dissolution test. Amber glass bottles, each containing 30 capsules, polyester coils and one desiccant pack, were individually sealed in aluminum foil bags and placed on stability testing under 2 storage conditions (2-8° C. and 25° C./60% RH).

Introduction

A total of 9 formulations (3 for each of the 3 dose strengths for X4P-001) were prepared and manually filled into size 1 hard gelatin capsules. The best capsule formulation of X4P-001 for each dose level was selected from three (3) formulation candidates based on 1-month R&D stability data (Table 3). The chosen formulation for each dose level was scaled-up for blending and capsule filling using V-blender and automated capsule filler, respectively.

The objectives of the pilot trial were: 1) to confirm the stability of the chosen formulations for X4P-001 10 mg, 25 mg and 100 mg capsules using a new lot of X4P-001; and 2) to collect information on scale up and the new process used for making X4P-001 capsules.

Materials and Equipment

List of Materials

X4P-001, lot #2893-A-3P
Microcrystalline Cellulose, NF, Avicel® PH-101, Lot #1155
Dibasic Calcium Phosphate Dihydrate, USP, Emcompress®, Lot #B10E
Croscarmellose Sodium, NF, Ac-Di-Sol®, Lot #T050N
Colloidal Silicon Dioxide, USP, Cab-O-Sil® M-5P, Lot #1J021
Sodium Stearyl Fumarate, NF, PRUV™, Lot #30001902
Sodium Lauryl Sulfate, NF, Lot #12810

Empty Hard Gelatin Capsules, Size 1 White Opaque, Lot #582410
  60 cc Amber Glass Bottles, with a green screw-on cap
  Silica Gel Desiccant Pouches, 0.5 g
  Rayon Coil 12-gram/y
  2×3 3-Spot Humidity Indicator Card, Lot #10018
  Aluminum Foil Bags MIL-PRF-131J
List of Equipment
  2-Qt. V-Blender
  Bonapace In-Cap Capsule Filling Machine
  Pouch Sealer
  Tap Density Tester
  Particle Size Analyzer (Sonic Sifter)
Experimental and Results
Selection of Formulation for the Pilot Trial One formulation (10-E, 25-E and 100-F) was chosen for the pilot X4P-001 trial at each of the 10 mg, 25 mg and 100 mg dose levels. The selection of the formulation was mainly based on the 1-month stability profile of the 3 formulations for each dose under 2 storage conditions (25° C./60% RH and 2-8° C.) (Table 3). None of the formulations were stable under the 40° C./75% RH storage condition.

Only Avicel® serves as a diluent/filler in both 10 mg and 25 mg formulations. To facilitate the capsule filling process on an automated capsule filler, a glidant such as colloidal silicon dioxide (Cab-O-Sil®) was explored for addition to the formulation. The trial on 2 placebo batches confirmed that the Cab-O-Sil® helps to reduce the weight variation of capsules (Table 4). Cab-O-Sil® was also added to the 100 mg formula (100-F) that contains both Avicel® and Emcompress® to ensure adequate flow of the powder blend.

In-Process Testing

A total of 3 formulations (1 for each of the 3 dose strength for X4P-001) were prepared. The powder blend was filled into size 1 hard gelatin capsules on In-Cap Capsule Filling Machine. The weight of the filled capsules showed about 1% in weight variability (RSD) (Table 5).

Initial Testing on Final Products

The average capsule fill weight of all batches was well within 1% of the target. The composite assay test results for batches #1191-10-PP, 1191-25-PP and 1191-100-PP were 98.8%, 99.0% and 99.9% respectively (Table 6).

The blend uniformity of all batches was evaluated using the USP Content Uniformity test. The content uniformity of the powder blend met the required 6% RSD (Table 6).

The dissolution test on 6 capsules from each batch was performed per USP dissolution method. All batches showed more than 99% drug release at 45 minutes (Table 6).

Stability Testing

Twenty (20) amber glass bottles each containing 30 capsules, appropriate amount of polyester coils and one desiccant pack were individually sealed in aluminum foil bags and placed on stability testing under 2 storage conditions (24° C. and 25° C./60% RH) per Pilot Stability Protocol (Table 8). One humidity indicating card was included in each aluminum foil bag for testing the seal of each sample.

Physical Properties of X4P-001 and the Powder Blend

Figure 16:
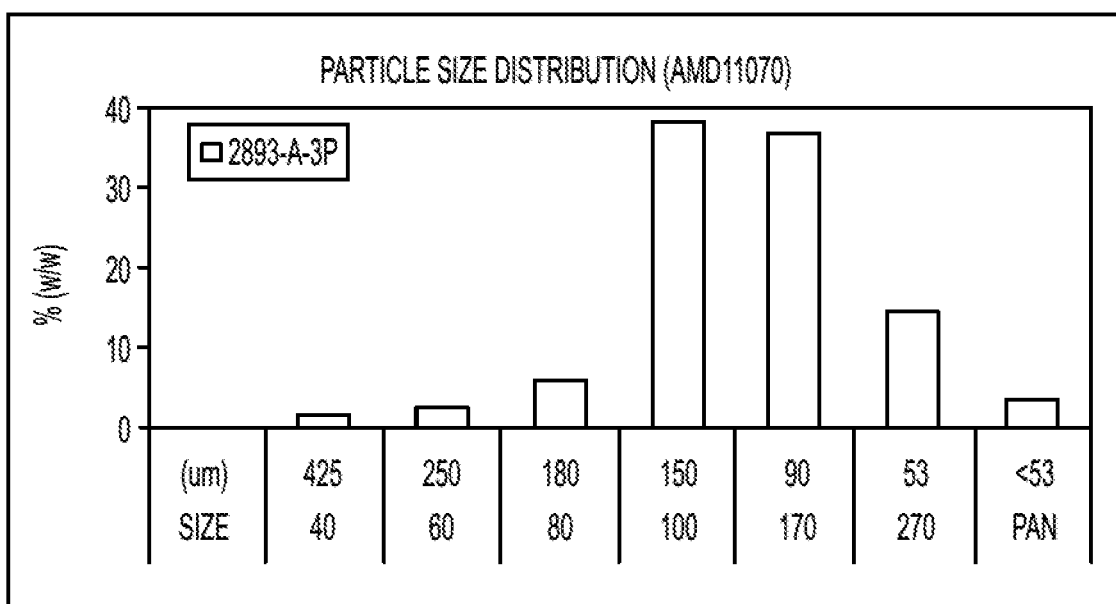
FIG. 16 illustrates particle size distribution of the X4P-001 batch used in developing the 10 mg, 25 mg, and 100 mg capsules.

Particle size distribution of X4P-001 is shown in Table 9 and FIG. 16. The results of bulk density, tap density and Can's Index are summarized in Table 7. The physical properties of the low strength blend for the 10 and 25 mg formulation were comparable to the R&D batches. However, the powder blend of the 100 mg batch showed lower bulk and tap density due to differences in two lots of X4P-001. The new lot is more bulky than the previous lot.

Conclusions

Three (3) pilot stability batches were successfully manufactured for the active pharmaceutical ingredient ("API"), X4P-001. The current process for all three dose levels is recommend for supporting the manufacturing of upcoming clinical batches. As used herein and in the following Tables, "API" refers to X4P-001. "API" is an abbreviation for "active pharmaceutical ingredient" that is commonly used in the art.

TABLE 3

Summary of 1-Month Stability Results on Chosen R&D Batches

| | Batch Information LOT NO. | | | | | |
|---|---|---|---|---|---|---|
| | 1191-10-E | | 1191-25-E | | 1191-100-F | |
| Parameters | 2-8° C. | 25° C./ 60% RH | 2-8° C. | 25° C./ 60% RH | 2-8° C. | 25° C./ 60% RH |
| API (mg) | 10 | | 25 | | 100 | |
| Batch Size (g) | 175 | | 175 | | 250 | |
| Dissolution | | | | | | |
| % at 45 min. | 112 | 110 | 91 | 95 | 99 | 96 |
| Assay @ 1-month | | | | | | |
| % LC | 105.5 | 110.5 | 99.2 | 100.7 | 94.1 | 91.5 |
| Related Substances | | | | | | |
| Tot. % Area | 2.0 | 2.2 | 2.0 | 2.3 | 0.9 | 1.2 |
| Assay @ time zero* | | | | | | |
| % LC | 99.4 | | 100.9 | | 94.0 | |
| Related Substances* | | | | | | |
| Tot. % Area | 0.4 | | 0.7 | | 94.0 | |

*The time zero data were included as reference

TABLE 4

Summary of Weight Variation Results on X4P-001 Capsules from Pilot Trials

| Parameters | Placebo-1 | Placebo-2 | 1191-100-H | 1191-10-P | 1191-25-P | 1191-100-P |
|---|---|---|---|---|---|---|
| Batch Information — PILOT BATCH LOT NO. | | | | | | |
| API (mg) | 0 | 0 | 100 | 10 | 25 | 100 |
| Batch Size (g) | 200 | 200 | 200 | 650 | 650 | 1200 |
| Formulation | | | | | | |
| API % | 0.0 | 0.0 | 37.6 | 6.0 | 14.7 | 37.6 |
| Avicel % | 92.8 | 92.5 | 22.9 | 86.7 | 78.1 | 22.9 |
| Emcomp. % | 0.0 | 0.0 | 31.7 | 0.0 | 0.0 | 31.7 |
| Ac-Di-Sol % | 6.3 | 6.3 | 6.0 | 6.0 | 6.0 | 6.0 |
| Cab-O-Sil % | 0.00 | 0.25 | 0.23 | 0.25 | 0.24 | 0.30 |
| PRUV % | 1.0 | 1.0 | 1.0 | 1.0 | 1.0 | 1.0 |
| SLS % | 0.0 | 0.0 | 0.5 | 0.0 | 0.0 | 0.5 |
| TOTAL % | 100.1 | 100.1 | 99.9 | 100.0 | 100.0 | 100.0 |
| Weight Statistics | | | | | | |
| N | 20 | 20 | 20 | 20 | 20 | 20 |
| MIN | 225.7 | 219.9 | 296.0 | 234.1 | 236.9 | 334.1 |
| MAX | 271.3 | 252.8 | 355.9 | 248.5 | 251.0 | 349.6 |
| MEAN | 250.6 | 244.6 | 339.0 | 241.9 | 245.0 | 341.0 |
| SD | 11.9 | 7.8 | 14.8 | 3.6 | 3.6 | 4.3 |
| Weight Variation | | | | | | |
| RSD | 4.8% | 3.2% | 4.4% | 1.5% | 1.5% | 1.3% |
| Wt. Var. w/o outliers | | | | | | |
| N | 19 | 19 | 18 | N/A | | |
| MEAN | 251.9 | 245.9 | 343.3 | | | |
| RSD | 4.2% | 2.2% | 2.0% | | | |

TABLE 5

Summary of In-Process Weight Check Results on X4P-001 Capsules

| Parameters | 1191-10-P | 1191-25-P | 1191-100-P |
|---|---|---|---|
| Batch Information LOT NO. | | | |
| API (mg) | 10 | 25 | 100 |
| Batch Size (g) | 650 | 650 | 1200 |
| Weight Statistics | | | |
| N | 11 | 10 | 11 |
| MIN | 239.5 | 239.0 | 336.9 |
| MAX | 245.0 | 249.0 | 344.8 |
| MEDIAN | 242.1 | 245.5 | 341.7 |
| MEAN | 242.5 | 245.1 | 341.6 |
| SD | 1.7 | 3.0 | 2.3 |
| Weight Variation | | | |
| RSD | 0.7% | 1.2% | 0.7% |
| Capsule Wt. ** | | | |
| 1 | 241.9 | 244.9 | 339.9 |
| 2 | 244.6 | 245.7 | 341.7 |
| 3 | 245.0 | 249.0 | 336.9 |
| 4 | 241.5 | 245.9 | 344.8 |
| 5 | 242.1 | 247.3 | 343.3 |
| 6 | 242.1 | 239.0 | 342.9 |
| 7 | 240.7 | 242.7 | 341.9 |
| 8 | 244.6 | 245.3 | 344.3 |
| 9 | 242.9 | 242.9 | 341.7 |
| 10 | 242.1 | 248.7 | 338.9 |
| 11 | 239.5 | | 340.8 |

**Average weight of 10 capsule samples, taken every 10 minutes during encapsulation.

TABLE 6

Summary of Time Zero Results on Pilot Stability Batches

| Parameters | 1191-10-PP | 1191-25-PP | 1191-100-PP |
|---|---|---|---|
| Batch Information LOT NO. | | | |
| API (mg) | 10 | 25 | 100 |
| Batch Size (g) | 650 | 650 | 1200 |
| Target Fill Wt. (mg) | 167 | 170 | 266 |
| Wt. Var. Capsules | | | |
| MEAN | 241.9 | 245.0 | 341.0 |
| Fill Wt. Capsules | | | |
| RSD | 1.5% | 1.5% | 1.3% |
| MEAN | 168 | 171 | 267 |
| Content Uniformity | | | |
| MEAN | 96.9% | 95.8% | 99.9% |
| Dissolution | | | |
| RSD | 2.2% | 2.3% | 5.2% |
| % at 45 min. | 99.6% | 100.8% | 99.7% |
| Assay | | | |
| % LC | 98.8% | 99.0% | 99.9% |
| Related Substances | | | |
| Tot. % Area | 1.4% | 1.4% | 1.5% |

TABLE 7

Comparison of Physical Properties of Powder Blends of R&D Batches

| Physical Parameters | Dev. Batches | Pilot Batches |
|---|---|---|
| 10 mg Batches → | 1191-10-E | 1191-10-P |
| Bulk Density (g/cc) | 0.34 | 0.36 |
| Tap Density (g/cc) | 0.53 | 0.51 |
| Carr's Index (%) | 36% | 28% |
| Mean PS (um) | n/a | 50 |
| 25 mg Batches → | 1191-25-E | 1191-25-P |
| Bulk Density (g/cc) | 0.36 | 0.36 |
| Tap Density (g/cc) | 0.55 | 0.52 |
| Carr's Index (%) | 34% | 32% |
| Mean PS (um) | n/a | 54 |
| 100 mg Batches → | 1191-100-F | 1191-100-P |
| Bulk Density (g/cc) | 0.8 | 0.62 |
| Tap Density (g/cc) | 1.08 | 0.84 |
| Carr's Index (%) | 26% | 26% |
| Mean PS (um) | n/a | 85 |

TABLE 8

Pilot Stability Protocol

PACKAGING INFORMATION:

| | |
|---|---|
| | Amber 60 cc glass bottle (sealed in aluminum foil bag) |
| Cap/Closure Type | Green plastic screw-on top |
| Number of Bottles Packaged | 15 bottles from each batch |
| Number of Capsules Per Bottle | 30 capsules (with polyester coils and 1 desiccant pack) |

STORAGE CONDITIONS:

| | Storage Conditions | Time Points | Total Number of Bottles |
|---|---|---|---|
| A | Ambient Temperature | Stability Time Zero | 2 + 1** |
| B | 25° C. + 2° C./60% + 5% RH | 1 M, 3 M | 2 + 2** |
| C | 2° C.-8° C. | 1 M, 3 M | 2 + 2** |
| | Totals | | 11 |

TESTING TO BE COMPLETED AT EACH TIME POINT:

| No. | Test | Method | Performed By | Acceptance Criteria |
|---|---|---|---|---|
| 1. | Appearance | Visual | Analytical Lab | Record results |
| 2. | Content Uniformity (initial time zero only) | HPLC | Analytical Lab | USP Requirements <905> |
| 3. | Assay | HPLC | Analytical Lab | Record results |
| 4. | Dissolution | USP Apparatus 2 | Analytical Lab | Record results |
| 5. | Odor | Olfactory | Formulation | Record results |

**Additional back-up bottles for all conditions.

TABLE 9

Particle Size Distribution

| | |
|---|---|
| Product: | X4P-001 Free Base |
| Lot#: | 2893-A-3P |
| Date: | 10-Jan-03 |
| Sample Wt.: | 5 grams |
| Testing Time: | 5 minutes |

| # Mesh Size | Par. Size (μm) | % Retained |
|---|---|---|
| 40 | 425 | 1.3 |
| 60 | 250 | 2.5 |
| 80 | 180 | 5.8 |
| 100 | 150 | 37.8 |
| 170 | 90 | 36.1 |
| 270 | 53 | 13.8 |
| Pan | <53 | 2.7 |
| Sum: | | 100.0 |

Example 7: Development and Formulation of 200 mg Capsule

This Example describes the development of a 200 mg strength of X4P-001 Capsules and process development activities.

The formulation for X4P-001 Capsules, 100 mg was employed as a baseline for the proposed 200 mg formulation. The goal of the formulation development activities was to obtain a higher dosage form of API with a similar dissolution profile to the 100 mg strength and manufacture the product in a size 1 gelatin capsule.

A feasibility batch was manufactured using a prototype capsule formulation (developed by Metrics) based on the excipients used in the 100 mg CTM batch formulation as shown in Table 10 below. This feasibility batch met all previously established drug product specifications and displayed a drug release similar to the 100 mg strength CTM batch (151(227). The goal of the X4P-001 Capsules, 200 mg formulation development activities was to identify an acceptable capsule formulation to be deployed in Phase 1 clinical studies and advanced into subsequent clinical study phases as appropriate using a scalable formulation and manufacturing process using a size 1 gelatin capsule, consistent with the current strengths (25 mg and 100 mg) of the subject product line.

TABLE 10

Formulation of 200 mg and 100 mg Capsules

| | 200 mg Strength | | 100 mg Strength | |
|---|---|---|---|---|
| INGREDIENTS | Percent Per Capsule (%) | Theoretical Amount Per Capsule (mg) | Percent Per Capsule (%) | Theoretical Amount Per Capsule (mg) |
| X4P-001 Drug Substance | 61.5 | 200.0 | 37.6 | 100.0 |
| Microcrystalline Cellulose, NF/EP (Avicel PH 101) or equivalent | 12.9 | 41.93 | 22.9 | 60.9 |

TABLE 10-continued

Formulation of 200 mg and 100 mg Capsules

| INGREDIENTS | 200 mg Strength Percent Per Capsule (%) | 200 mg Strength Theoretical Amount Per Capsule (mg) | 100 mg Strength Percent Per Capsule (%) | 100 mg Strength Theoretical Amount Per Capsule (mg) |
|---|---|---|---|---|
| Dibasic Calcium Phosphate Dihydrate, USP/NF | 17.8 | 57.85 | 31.7 | 84.30 |
| Croscarmellose Sodium, NF/EP (Ac-Di-Sol) | 6.0 | 19.50 | 6.0 | 16.00 |
| Sodium Lauryl Sulfate, NF/Ph. Eur. | 0.5 | 1.625 | 0.5 | 1.300 |
| Colloidal Silicone Dioxide, NF/Ph. Eur. (Cab-O-Sil M-5P) | 0.3 | 0.9750 | 0.3 | 0.8000 |
| Sodium Stearyl Fumarate, NF (Pruv) | 1.0 | 3.250 | 1.0 | 2.700 |
| Total Capsule Fill | 100.0 | 325.0 | 100.0 | 266.0 |
| Capsules, Empty, Hard Gelatin Size 1 White/White | 1 Capsule | | 1 Capsule | |

Figure 8:
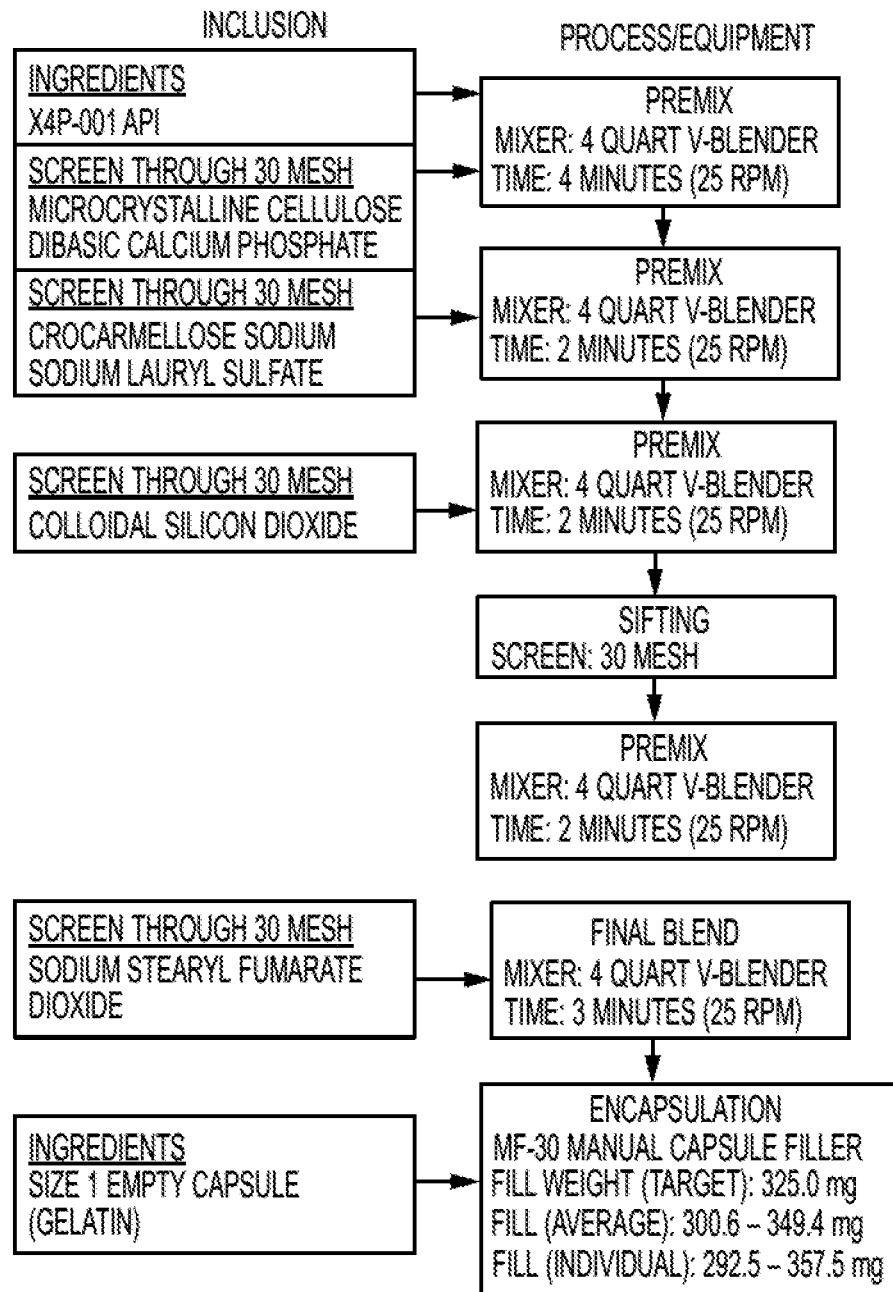
FIG. 8 illustrates a process flow diagram for manufacturing 200 mg X4P-001 Capsules.

One feasibility batch was prepared using the formulation outlined in Table 10 above. Feasibility batch manufacturing equipment included: V-shell blender (4 quart), 30 mesh hand screen, and MF-30 Manual Capsule Filler. The manufacturing process for each batch is described below and depicted in FIG. 8. The batch manufacture process utilized the same process train as the current 100 mg strength.

1. Add the X4P-001 active ingredient to the 4 quart V-Blender.
2. Sift Avicel PH-101 and Dibasic Calcium Phosphate through a 30 mesh hand screen and add to the 4 quart V-blender. Mix for 4 minutes (100 rotations).
3. Sift Croscarmellose Sodium and Sodium Lauryl Sulfate through a 30 mesh hand screen and add to the 4 quart V-Blender. Mix for 2 minutes (50 rotations).
4. Sift Colloidal Silicon Dioxide through a 30 mesh hand screen and add to the 4 quart V-Blender. Mix for 2 minutes (50 rotations).
5. Discharge blended materials from the 4 quart V-Blender and sift through a 30 mesh screen. Transfer screened material back to the 4 quart V-Blender and mix for 2 minutes (50 rotations).
6. Sift Sodium Stearyl Fumarate through a 30 mesh hand screen and add to the 4 quart V-Blender. Mix for 3 minutes (75 rotations).
7. Encapsulate the blended material using an MF-30 Manual Capsule Filler to a target weight of 325.0 mg/capsule.

The completed final blend was encapsulated using an MF-30 Manual Capsule Filler, filled capsule properties are presented in Table 11, below.

TABLE 11

X4P-001 Capsules, 200 mg Capsule Fill Weight

| Capsule Parameter | Batch 15/858-034 (X4P-001 Capsules, 200 mg) |
|---|---|
| Tray 1 Average Weight | 319.1 mg |
| Tray 2 Average Weight | 320.1 mg |
| Tray 3 Average Weight | 327.6 mg |
| Individual Max | 350.6 mg |
| Individual Min | 298.1 mg |
| RSD (%) | 3.5 |

Following completion of the encapsulation activities a single capsule was filled using the MF-30 manual encapsulation to determine the maximum fill weight that could be filled into a size 1 capsule using the remaining finished blend. A fill weight of 425.0 mg was obtained during execution of the activity.

The conclusion of the encapsulation process development effort showed that encapsulation is a viable operation for processing the product.

Analytical Results of X4P-001 Capsules, 200 mg Feasibility Batch.

Figure 9:
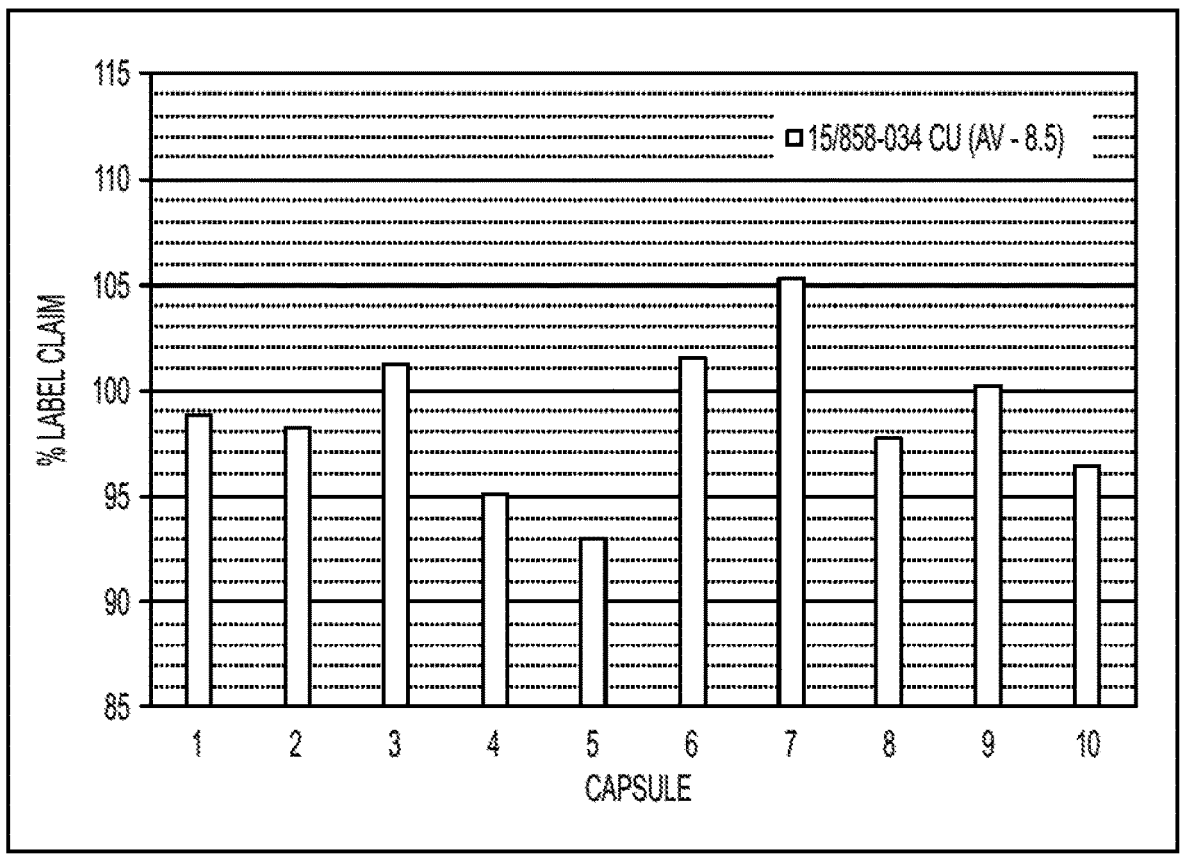
FIG. 9 illustrates measurements of X4P-001 200 mg capsule fills vs. theoretical capsule fill.
Figure 10:
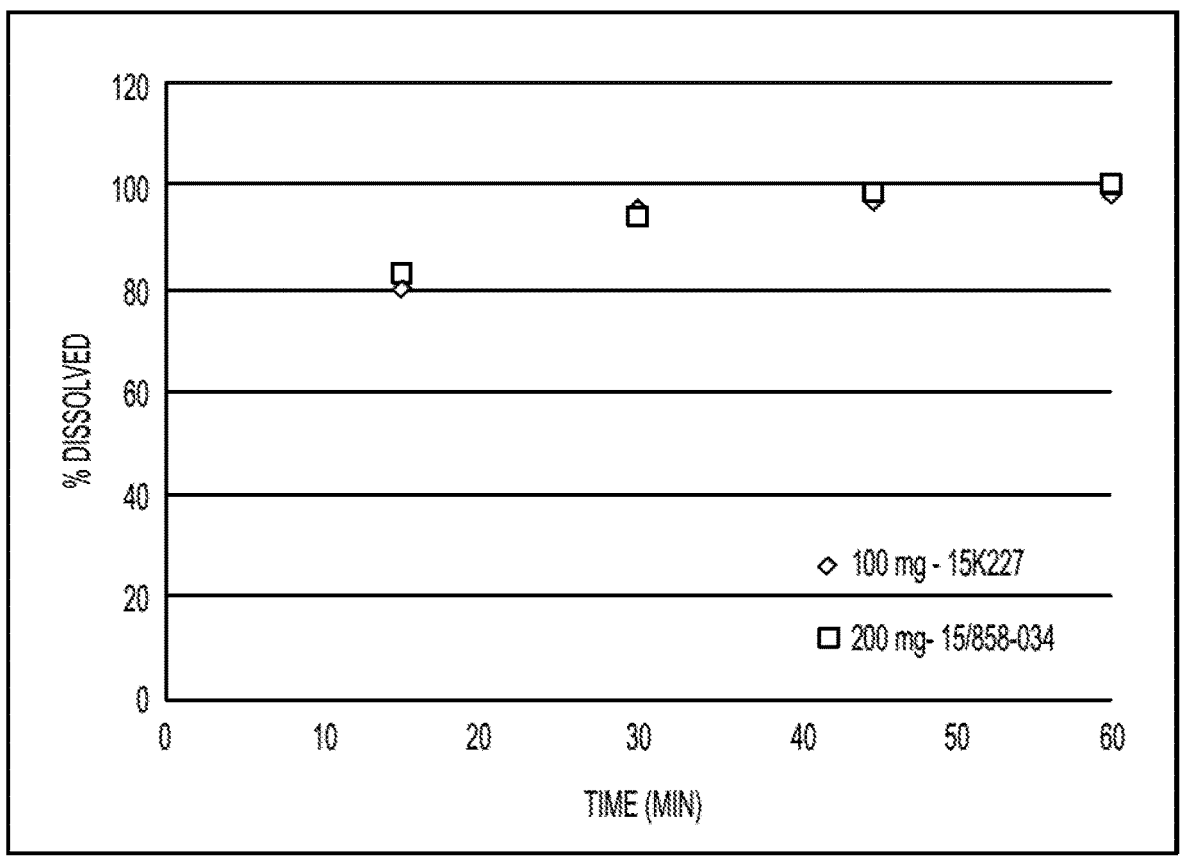
FIG. 10 illustrates the dissolution profile of the developed X4P-001 200 mg capsules vs. the dissolution profile of the X4P-001 100 mg capsules.

Feasibility batch 15/858-034 was tested for Assay/Related Substances, Moisture, Dissolution, and Content Uniformity. Results of this testing are shown in FIGS. 9 and 10. The result of the assay testing was 97.4% of label claim with total impurities of 0.75% and a moisture value of 3.9% w/w.

Comparison of the dissolution profile results of the 200 mg formulation composition compared to the 100 mg formulation CTM batch (151(227) is presented in FIG. 10. The proposed 200 mg formulation compared favorable to the current 100 mg formulation with an f2 similarity factor of 83.

REFERENCES

1. Panka D J, Liu Q, Geissler A K, Mier J W. HDM2 antagonism delays the development of sunitinib resistance in RCC xenografts: Effects of MI-319 on sunitinib-induced p53 activation, SDF-1 induction, and tumor infiltration by CD11b+/Gr-1+ myeloid suppressor cells. Mol Cancer 2013; 12: 17.
2. Shojaei F, Wu X, Malik A K, Zhong C, Baldwin M E, Schanz S, Fuh G, Gerber H P, Ferrara N. Tumor refractoriness to anti-VEGF treatment is mediated by CD11b+ Gr1+ myeloid cells. Nature Biotech 2007; 25: 911-20.
3. Zea A H, Rodriguez P C, Atkins M B, Hernandez C, Signoretti S, Zabaleta J, McDermott D, Quiceno D, Youmans A, O'Neill A, Mier J, Ochoa A C. Arginase-producing myeloid suppressor cells in renal cell carcinoma patients: a mechanism of tumor evasion. Cancer Res 2005; 65: 3044-8.
4. Nagaraj S, Gupta K, Pisarev V. Kinarsky L, Sherman S, Kang L, Herber D L, Schneck J, Gabrilovich D I. Altered recognition of antigen is a mechanism of CD8+ T cell tolerance in cancer. Nat Med 2007; 13: 828-35.
5. Finke J, Ko J Rini B, Rayman P, Ireland J, Cohen P. MDSC as a mechanism of tumor escape from sunitinib mediated anti-angiogenic therapy. Int Immunopharmacol 2011; 11: 856-61.
6. Moskovits N, Kalinkovich A, Bar J, Lapidot T, Oren M. p53 attenuates cancer cell migration and invasion through repression of SDF-1/CXCL12 expression in stromal fibroblasts. Cancer Res 2006; 66: 10671-6.
7. Vanharanta S, Shu W, Brenet F, Hakimi A A, Heguy A, Viale A, Reuter V E, Hsieh J J-D, Scandura J M, Massagué J. Epigenetic expansion of VHL-HIF signal output drives multiorgan metastasis in renal cancer. Nat Med 2013; 19: 50-6.
8. Gale L M, McColl S R. Chemokines: extracellular messengers for all occasions? BioEssays 1999; 21: 17-28.
9. Highfill S L, Cui Y, Giles A J, Smith J P, Zhang H, Morse E, Kaplan R N, Mackall C L. Disruption of CXCR2-mediated MDSC tumor trafficking enhances anti-PD1 efficacy. Sci Transl Med 2014; 6: ra67.
10. Facciabene A, Peng X, Hagemann J S, Balint K, Barchetti A, Wang L-P, Gimotty P A, Gilks C B, Lal P, Zhang L, Coukos G. Tumour hypoxia promotes tolerance and angiogenesis via CCL28 and Treg cells. Nature 2011; 475: 226-230.
11. Montane J, Bischoff L, Soukhatcheva G, Dai D L, Hardenberg G, Levings M K, Orban P C, Kieffer T J, Tan R, Verchere C B. Prevention of murine autoimmune diabetes by CCL22-mediated Treg recruitment to pancreatic islets. J Clin Invest 2011; 121: 3024-8.
12. Acharyya S, Oskarsson T, Vanharanta S, Malladi S, Kim J, Morris P G, Monava-Todorova K, Leversha M, Hogg N, Seshan V E, Norton L, Brogi E, Massague J. A CXCL1 paracrine network links cancer chemoresistance and metastasis. Cell 2012; 150: 165-78.
13. Zhao X, Rong L, Zhao X, Xiao L, Liu X, Deng J, Wu H, Xu X, Erben U, Wu P, Syrbe U, Sieper J, Qin Z. TNF signaling drives myeloid-derived suppressor cell accumulation. J Clin Invest 2012; 122: 4094-4104.
14. Silva J M, Marran K, Parker J S, Silva J, Golding M, Schlabach M R, Elledge S J, Hannon G J, Chang K. Profiling essential genes in human mammary cells by multiplex RNA1 screening. Science 2008; 319: 617-20.
15. Schlabach M R, Luo J, Solimini N L, Hu G, Xu Q, Li M Z, Zhao Z, Smogorzewska A, Sowa M E, Ang X L, Westbrook T F, Liang A C, Chang K, Hackett J A, Harper J W, Hannon G J, Elledge S J. Cancer proliferation gene discovery through functional genomics. Science 2008; 319: 620-24.
16. Shen H B, Gu ZQ, Jian K, Qi J. CXCR4-mediated STAT3 activation is essential for CXCL12-induced invasion in bladder cancer. Tumour Biol 2013; 34: 1839-45.
17. Tu S P, Jin H, Shi J D, Zhu L M, Suo Y, Liu G, Liu A, Wang T C, Yang C S. Curcumin induces the differentiation of myeloid-derived suppressor cells and inhibits their interaction with cancer cells and related tumor growth. Cancer Prev Res 2011; 5: 205-15.
18. Husain Z, Huang Y, Seth P J, Sukhatme V P. Tumor-derived lactate modifies antitumor immune response: Effect on myeloid-derived suppressor cells and NK cells. J Immunol 2013; 191: 1486-95.

We claim:

1. A composition comprising:
   (a) X4P-001, or a pharmaceutically acceptable salt thereof about 37% by weight of the composition;
   (b) microcrystalline cellulose about 23% by weight of the composition;
   (c) dibasic calcium phosphate dihydrate—about 32% by weight of the composition;
   (d) croscarmellose sodium—about 6% by weight of the composition;
   (e) sodium stearyl fumarate—about 1% by weight of the composition;
   (f) colloidal silicon dioxide—about 0.3% by weight of the composition; and
   (g) sodium lauryl sulfate—about 0.5% by weight of the composition.

2. The composition according to claim 1, wherein the X4P-001, or a pharmaceutically acceptable salt thereof, is present in an amount of about 10 mg, about 20 mg, about 25 mg, about 50 mg, about 75 mg, about 100 mg, about 150 mg, about 200 mg, about 250 mg, about 300 mg, about 400 mg, about 450 mg, about 500 mg, about 600 mg, about 700 mg, about 750 mg, about 800 mg, about 900 mg, about 1000 mg, about 1100 mg, or about 1200 mg.

3. A composition comprising:
   (a) X4P-001, or a pharmaceutically acceptable salt thereof—about 14.7% by weight of the composition;
   (b) microcrystalline cellulose—about 78.1% by weight of the composition;
   (c) croscarmellose sodium—about 6.0% by weight of the composition;
   (d) sodium stearyl fumarate—about 1.0% by weight of the composition; and
   (e) colloidal silicon dioxide—about 0.2% by weight of the composition.

4. The composition of claim 3, wherein the composition comprises about 25 mg of X4P-001, or a pharmaceutically acceptable salt thereof.

5. The composition of claim 1, where the composition comprises about 100 mg of X4P-001, or a pharmaceutically acceptable salt thereof.

6. The composition of claim 1, wherein 3, where the composition comprises:
   (a) X4P-001, or a pharmaceutically acceptable salt thereof—about 37.6% by weight of the composition;
   (b) microcrystalline cellulose—about 22.9% by weight of the composition;
   (c) dibasic calcium phosphate dihydrate—about 31.7% by weight of the composition;
   (d) croscarmellose sodium—about 6.0% by weight of the composition;
   (e) sodium stearyl fumarate—about 1.0% by weight of the composition;
   (f) colloidal silicon dioxide—about 0.3% by weight of the composition; and
   (g) sodium lauryl sulfate—about 0.5% by weight of the composition.

7. A composition comprising:
   (a) X4P-001, or a pharmaceutically acceptable salt thereof—about 61.5% by weight of the composition;
   (b) microcrystalline cellulose—about 12.9% by weight of the composition;
   (c) dibasic calcium phosphate dihydrate—about 17.8% by weight of the composition;
   (d) croscarmellose sodium—about 6.0% by weight of the composition;
   (e) sodium stearyl fumarate—about 1.0% by weight of the composition;
   (f) colloidal silicon dioxide—about 0.3% by weight of the composition; and (g) sodium lauryl sulfate—about 0.5% by weight of the composition.

8. The composition of claim 7, wherein the composition comprises about 200 mg of X4P-001, or a pharmaceutically acceptable salt thereof.

9. A unit dosage form comprising the composition of claim 3.

10. The unit dosage form of claim 9, wherein the unit dosage form is in the form of a capsule.

11. A unit dosage form comprising the composition of claim 1.

12. The unit dosage form of claim 11, wherein the unit dosage form is in the form of a capsule.

13. A unit dosage form comprising the composition of claim 7.

14. The unit dosage form of claim 13, wherein the unit dosage form is in the form of a capsule.

* * * * *